US012594023B2

(12) United States Patent (10) Patent No.: US 12,594,023 B2
Park (45) Date of Patent: Apr. 7, 2026

(54) METHOD AND DEVICE FOR PROVIDING ALOPECIA INFORMATION

(71) Applicant: Becon Co., Ltd., Seoul (KR)

(72) Inventor: Min Suk Park, Gyeonggi-do (KR)

(73) Assignee: BECON CO., LTD., Seoul (KR)

( * ) Notice: Subject to any disclaimer, the term of this patent is extended or adjusted under 35 U.S.C. 154(b) by 302 days.

(21) Appl. No.: 18/547,342

(22) PCT Filed: Feb. 18, 2022

(86) PCT No.: PCT/KR2022/002403
§ 371 (c)(1),
(2) Date: Sep. 26, 2023

(87) PCT Pub. No.: WO2022/182067
PCT Pub. Date: Sep. 1, 2022

(65) Prior Publication Data
US 2024/0032856 A1 Feb. 1, 2024

(30) Foreign Application Priority Data

Feb. 23, 2021 (KR) ........................ 10-2021-0024387
Feb. 23, 2021 (KR) ........................ 10-2021-0024388
(Continued)

(51) Int. Cl.
*G06T 7/11* (2017.01)
*A61B 5/00* (2006.01)
(Continued)

(52) U.S. Cl.
CPC ............ *A61B 5/448* (2013.01); *G06T 7/0014* (2013.01); *G06T 7/11* (2017.01); *G16H 30/40* (2018.01);
(Continued)

(58) Field of Classification Search
CPC ................................ A61B 5/448; G16H 30/40
See application file for complete search history.

(56) References Cited

U.S. PATENT DOCUMENTS 9,355,304 B2 5/2016 Do et al.
10,573,026 B2 * 2/2020 Kasprzak ............... A61B 5/448
(Continued)

FOREIGN PATENT DOCUMENTS

KR 10-2004-0048668 A 6/2004
KR 20150113699 A 10/2015
(Continued)

OTHER PUBLICATIONS

International Search Report for corresponding International Application No. PCT/KR2022/002403 mailed May 30, 2022.
(Continued)

*Primary Examiner* — Edward Park
(74) *Attorney, Agent, or Firm* — Chrisman Gallo Tochtrop LLC

(57) ABSTRACT

According to an aspect of the present disclosure, there is provided a method of providing hair loss state information, the method comprising: obtaining a head image of a user; extracting a plurality of feature points from the head image, wherein the plurality of feature points include a first group of feature points and a second group of feature points; extracting a plurality of boundary points corresponding to boundaries of a hair and a forehead of the user from the head image; selecting a matching boundary point corresponding to the first group of feature points from among the plurality of boundary points; obtaining a top-face portion calculation value determined based on a distance between the first group of feature points and a matching boundary point corresponding to the first group of feature points with respect to a first axis on the head image; obtaining a middle-bottom-face portion calculation value determined based on a distance (Continued)

USER TERMINAL

1000 between the first group of feature points and the second group of feature points with respect to the first axis; and providing hair loss state information of the user based on a ratio of the top-face portion calculation value and the middle-bottom-face portion calculation value.

10 Claims, 63 Drawing Sheets

(30)          Foreign Application Priority Data

Mar. 26, 2021   (KR) ........................ 10-2021-0039223
May 24, 2021   (KR) ........................ 10-2021-0066242

(51)  Int. Cl.
    *G06T 7/00*          (2017.01)
    *G16H 30/40*        (2018.01)
(52)  U.S. Cl.
    CPC ............... *G06T 2207/20084* (2013.01); *G06T 2207/30088* (2013.01)

(56)                    References Cited

U.S. PATENT DOCUMENTS

2015/0310262 A1    10/2015  Do et al.
2020/0383631 A1*   12/2020  Canfield ................ A61B 5/446

FOREIGN PATENT DOCUMENTS

| | | |
|---|---|---|
| KR | 10-1571241 A | 11/2015 |
| KR | 20150122441 A | 11/2015 |
| KR | 20170019823 A | 2/2017 |
| KR | 20170088174 A | 8/2017 |
| KR | 20190051256 A | 5/2019 |
| KR | 10-2019-0123067 A | 10/2019 |
| KR | 10-2019-0135598 A | 12/2019 |
| KR | 20200110871 A | 9/2020 |
| KR | 20210051839 A | 5/2021 |
| KR | 10-2272468 A | 6/2021 |

OTHER PUBLICATIONS

Written Opinion for corresponding International Application No. PCT/KR2022/002403 dated May 30, 2022.

* cited by examiner

1000

1000

600
POWER SUPPLY UNIT

200
IMAGE CAPTURE UNIT

400
USER INPUT UNIT

CONTROLLER

300
STORAGE

500
OUTPUT UNIT

700
COMMUNICATION UNIT

100

(a)

(b)

BP

FIG. 14
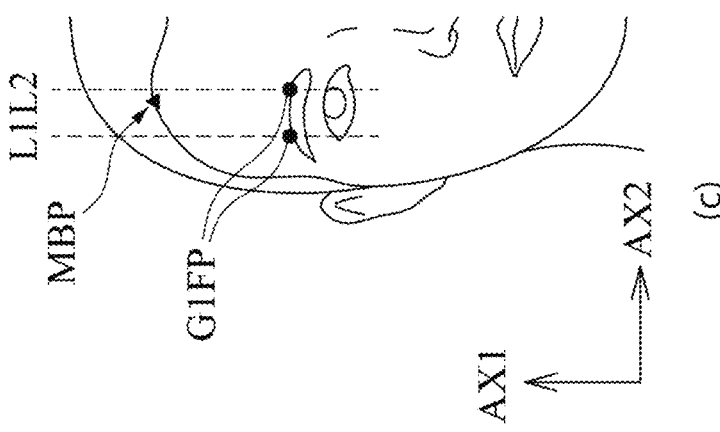
(c)
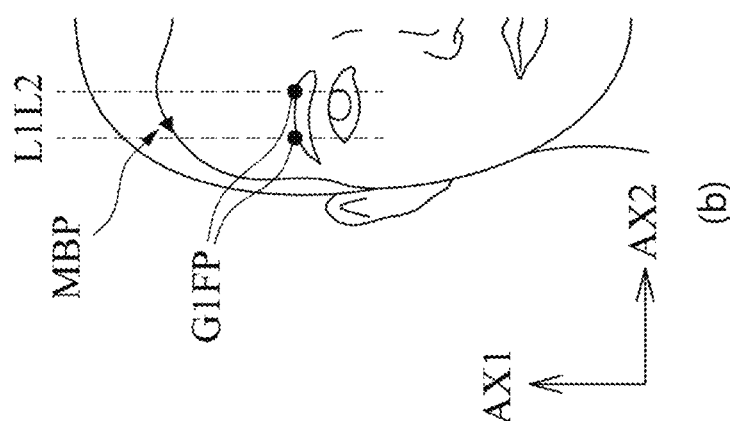
(b)
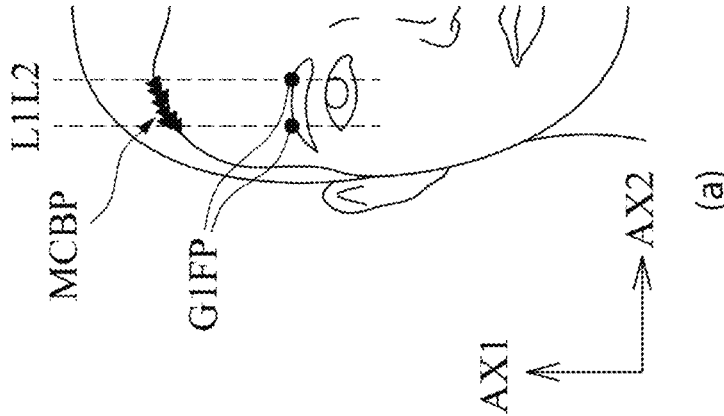
(a)

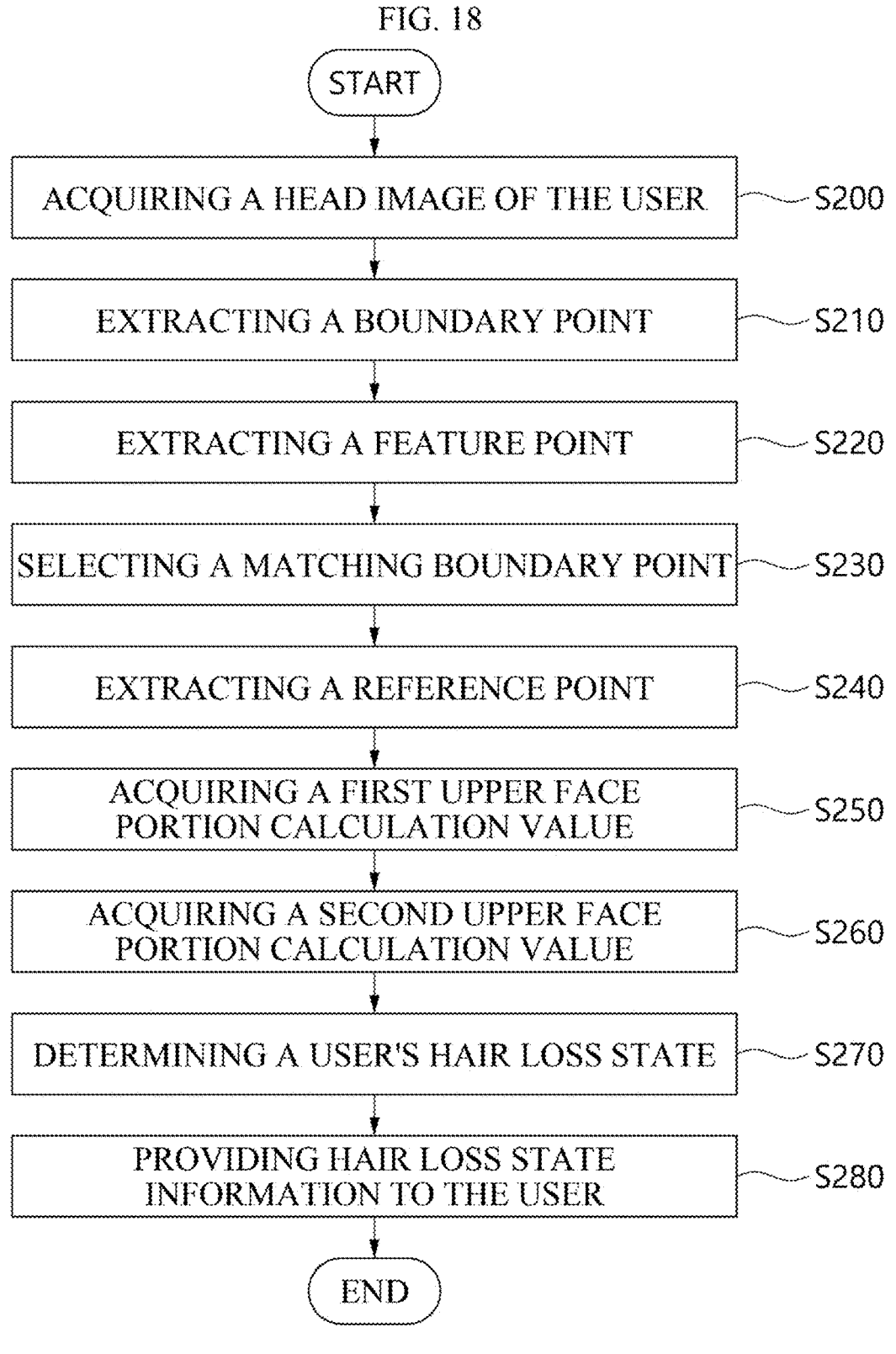

START

ACQUIRING A HEAD IMAGE OF THE USER — S200

EXTRACTING A BOUNDARY POINT — S210

EXTRACTING A FEATURE POINT — S220

SELECTING A MATCHING BOUNDARY POINT — S230

EXTRACTING A REFERENCE POINT — S240

ACQUIRING A FIRST UPPER FACE PORTION CALCULATION VALUE — S250

ACQUIRING A SECOND UPPER FACE PORTION CALCULATION VALUE — S260

DETERMINING A USER'S HAIR LOSS STATE — S270

PROVIDING HAIR LOSS STATE INFORMATION TO THE USER — S280

END

FIG. 32
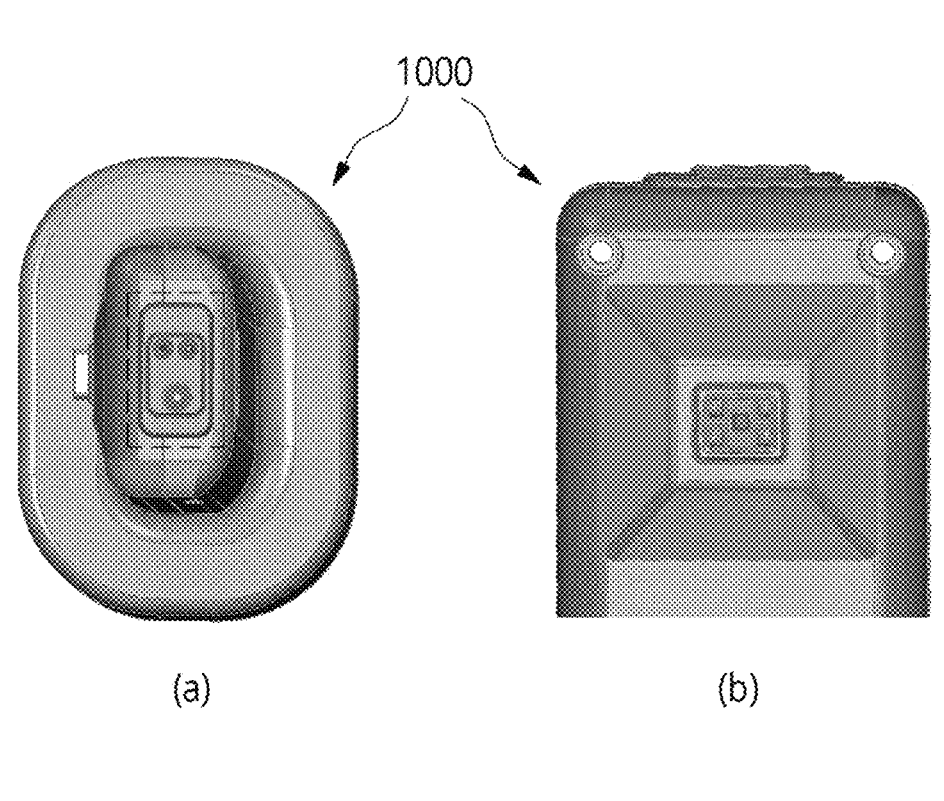
(a)                                    (b)
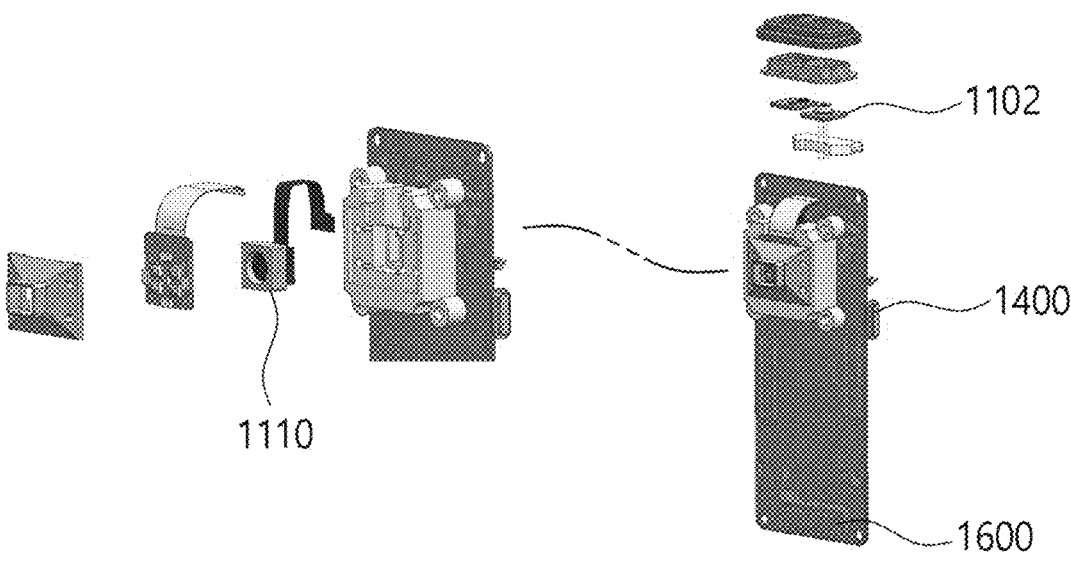
(c)

S1100

(a)                                        (b)

SCALP IMAGE

TRAINED NEURAL
NETWORK MODEL

PORE REGION INFORMATION

FIG. 39

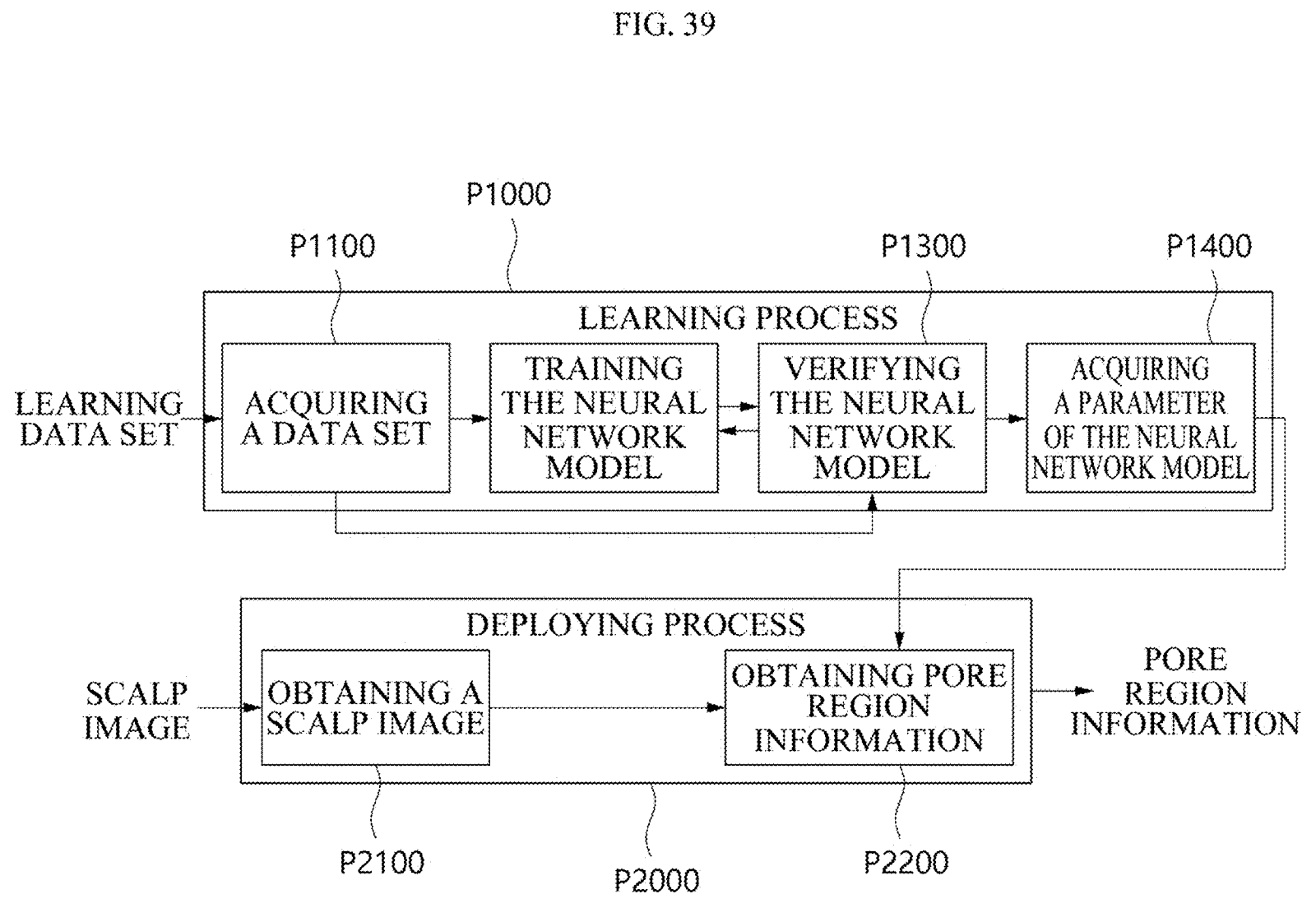

LEARNING PROCESS   P1000

P1100    LEARNING DATA SET  → ACQUIRING A DATA SET

P1300   TRAINING THE NEURAL NETWORK MODEL

VERIFYING THE NEURAL NETWORK MODEL

P1400   ACQUIRING A PARAMETER OF THE NEURAL NETWORK MODEL

DEPLOYING PROCESS   P2000

P2100   SCALP IMAGE →　OBTAINING A SCALP IMAGE

P2200   OBTAINING PORE REGION INFORMATION → PORE REGION INFORMATION

FIG. 44

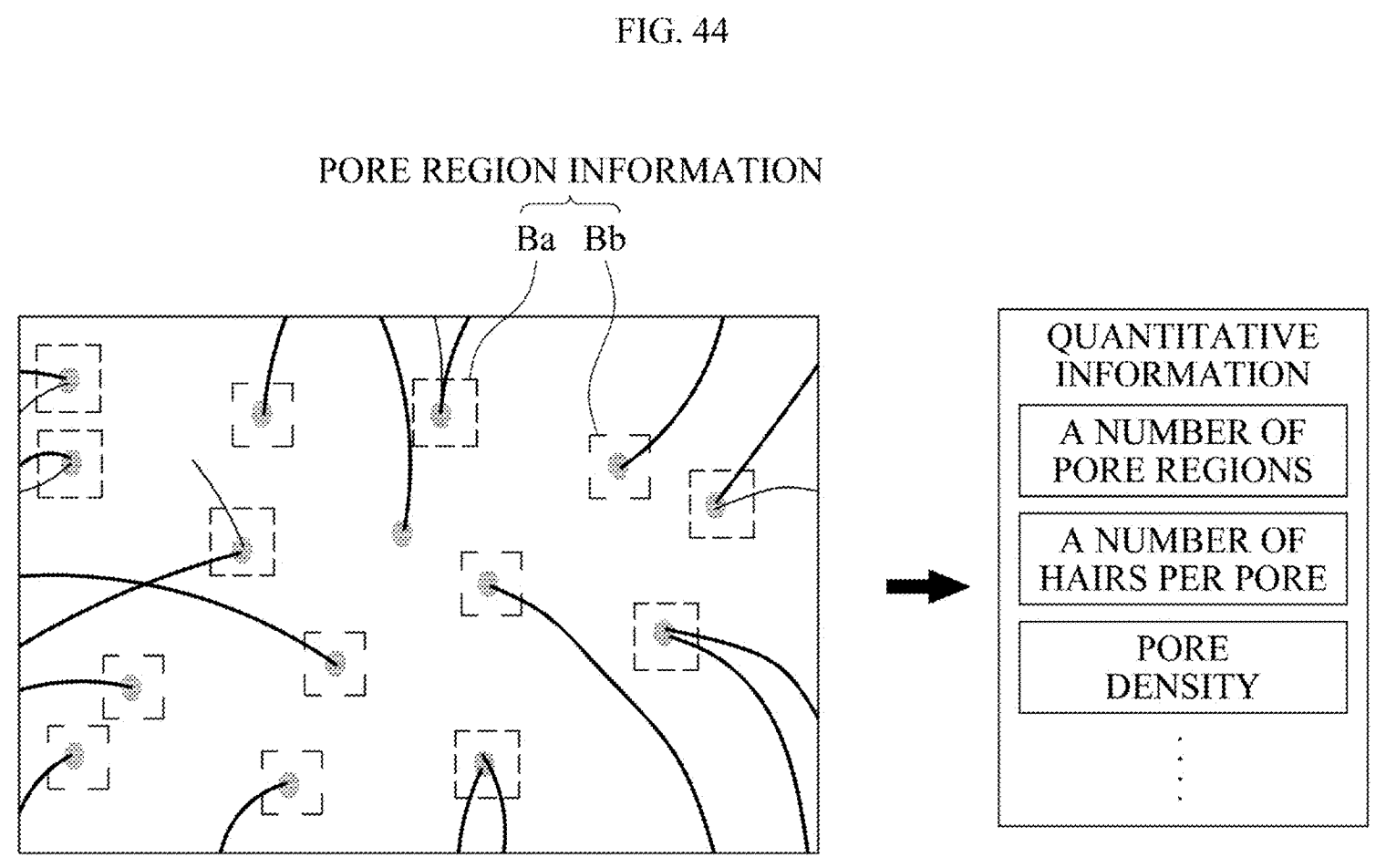

QUANTITATIVE INFORMATION

A NUMBER OF PORE REGIONS

A NUMBER OF HAIRS PER PORE

PORE DENSITY

. . . .

PORE REGION INFORMATION

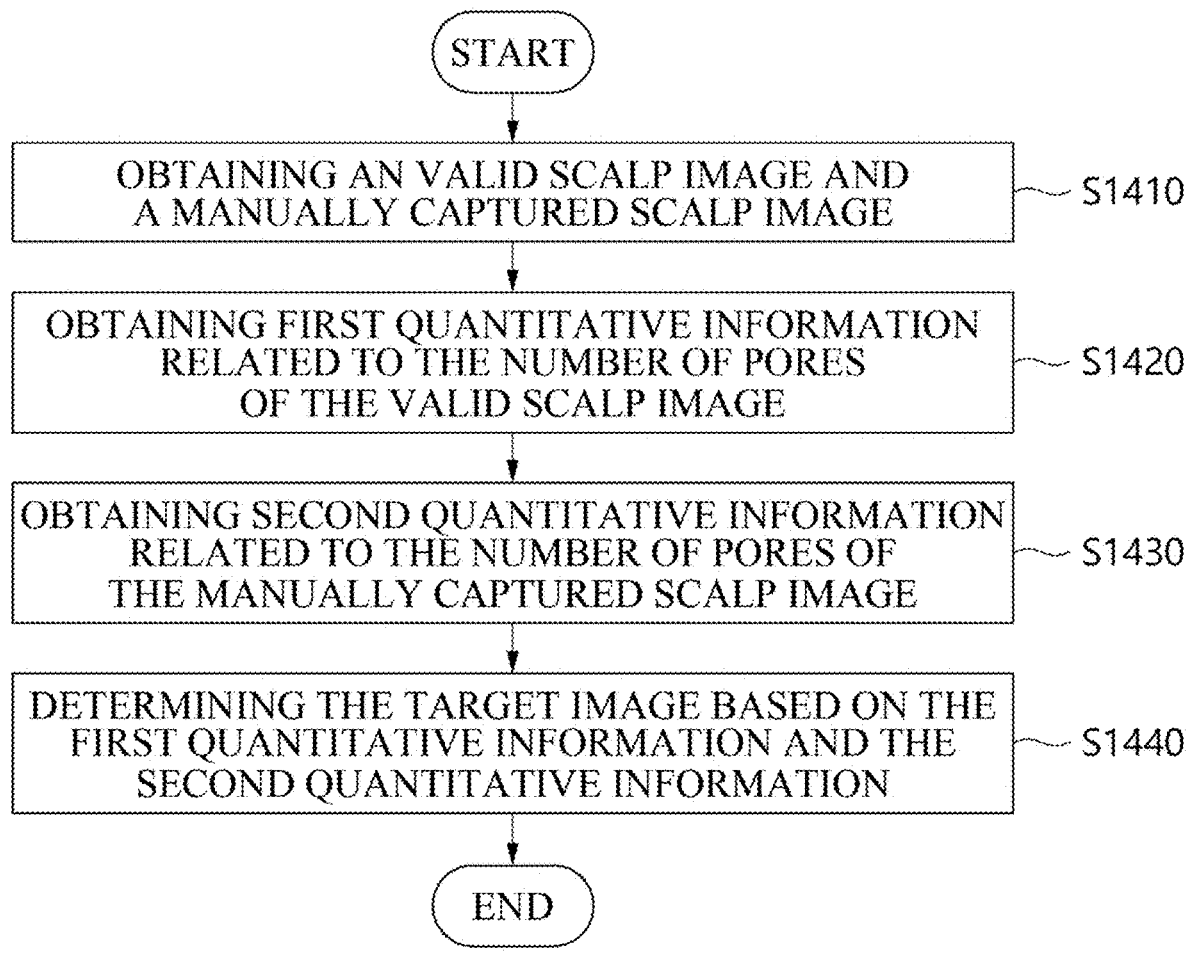

S1400

START

OBTAINING AN VALID SCALP IMAGE AND
A MANUALLY CAPTURED SCALP IMAGE ~ S1410

OBTAINING FIRST QUANTITATIVE INFORMATION
RELATED TO THE NUMBER OF PORES
OF THE VALID SCALP IMAGE ~ S1420

OBTAINING SECOND QUANTITATIVE INFORMATION
RELATED TO THE NUMBER OF PORES OF
THE MANUALLY CAPTURED SCALP IMAGE ~ S1430

DETERMINING THE TARGET IMAGE BASED ON THE
FIRST QUANTITATIVE INFORMATION AND THE
SECOND QUANTITATIVE INFORMATION ~ S1440

END

TARGET IMAGE

TRAINED NEURAL
NETWORK MODEL

INITIAL PORE REGION INFORMATION

INITIAL PORE REGION INFORMATION

POST PROCESSING

FINAL PORE REGION INFORMATION

FIG. 54

FIG. 57
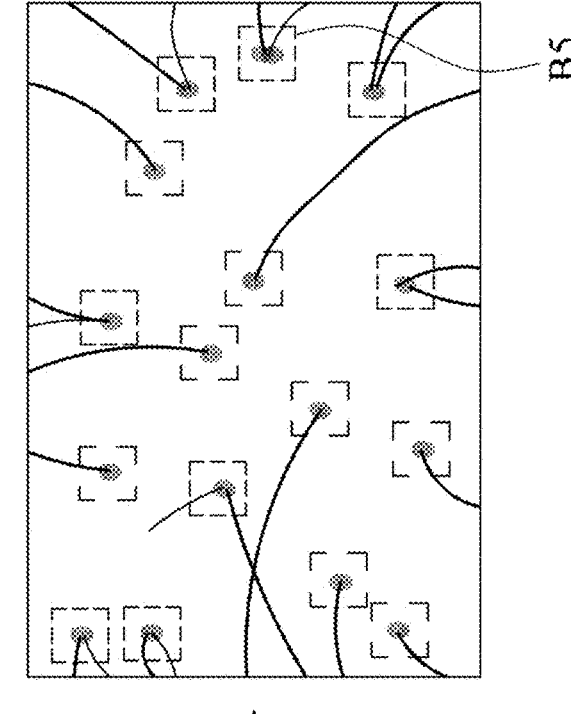
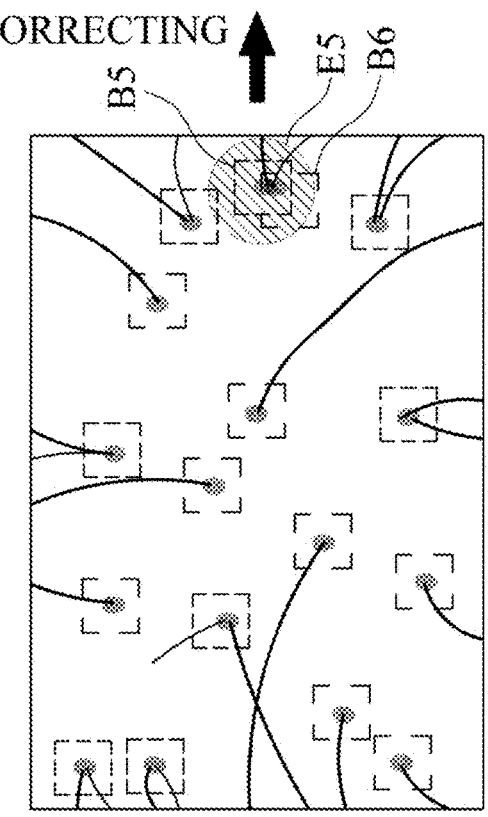
CORRECTING

FIG. 61

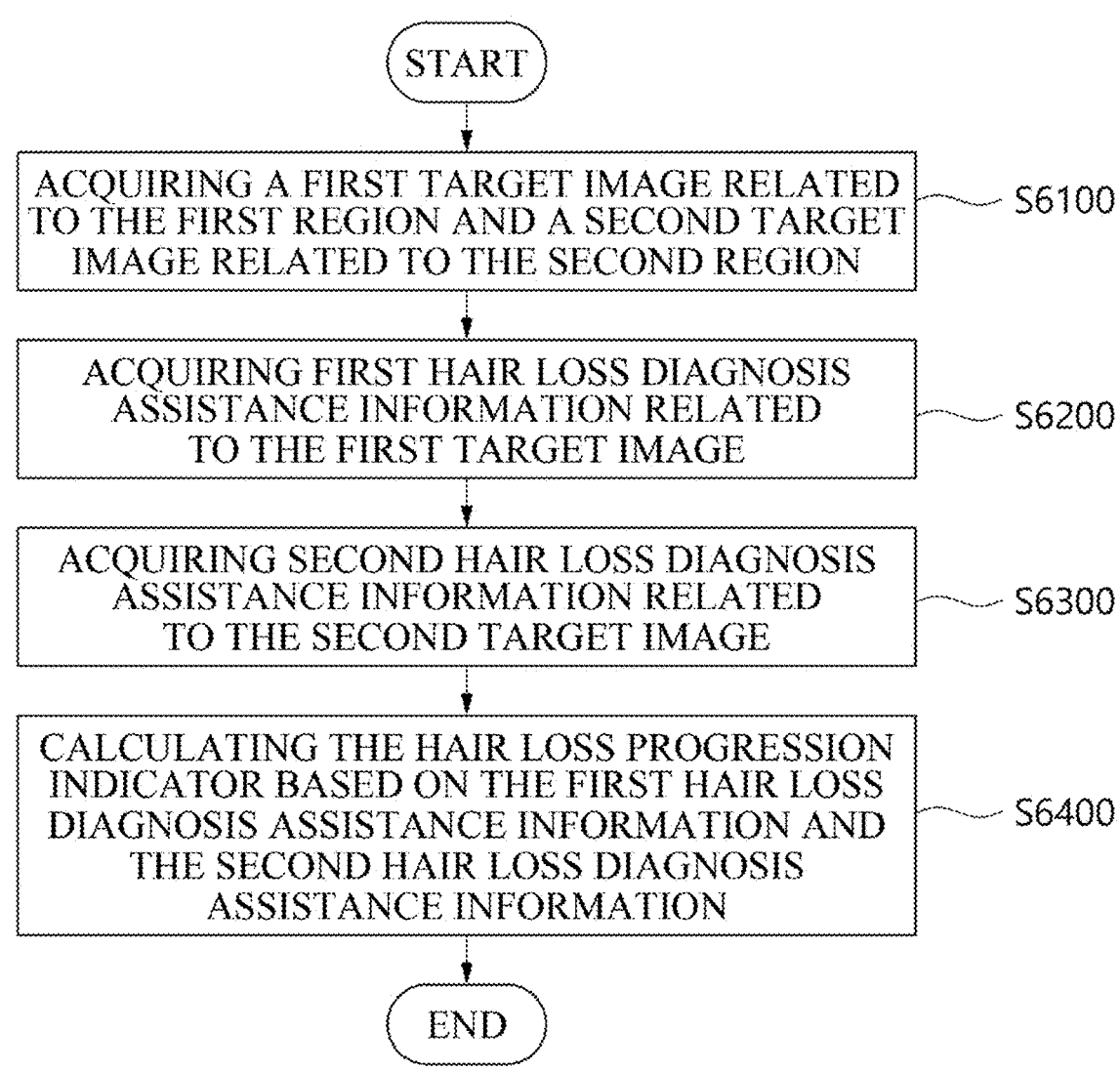

START

ACQUIRING A FIRST TARGET IMAGE RELATED TO THE FIRST REGION AND A SECOND TARGET IMAGE RELATED TO THE SECOND REGION — S6100

ACQUIRING FIRST HAIR LOSS DIAGNOSIS ASSISTANCE INFORMATION RELATED TO THE FIRST TARGET IMAGE — S6200

ACQUIRING SECOND HAIR LOSS DIAGNOSIS ASSISTANCE INFORMATION RELATED TO THE SECOND TARGET IMAGE — S6300

CALCULATING THE HAIR LOSS PROGRESSION INDICATOR BASED ON THE FIRST HAIR LOSS DIAGNOSIS ASSISTANCE INFORMATION AND THE SECOND HAIR LOSS DIAGNOSIS ASSISTANCE INFORMATION — S6400

END

FIG. 62
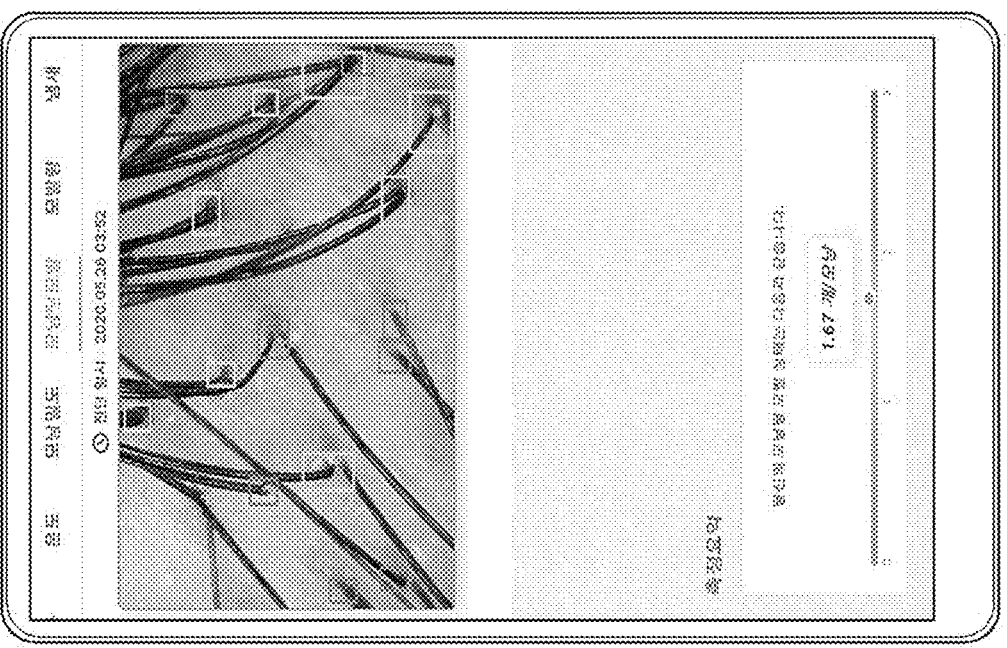

METHOD AND DEVICE FOR PROVIDING ALOPECIA INFORMATION

CROSS-REFERENCE TO RELATED APPLICATIONS

This application is a national stage entry of International Application No. PCT/KR2022/002403 filed on Feb. 18, 2022, which claims the benefit of priority to Korean Application Nos. KR10-2021-0024387, filed Feb. 23, 2021, KR10-2021-0024388 filed on Feb. 23, 2021, KR10-2021-0039223 filed on Mar. 26, 2021 and KR10-2021-0066242 filed on May 24, 2021, the entire disclosures of which are hereby incorporated herein by reference.

BACKGROUND

1. Field of the Invention

The present application relates to a method for providing hair loss state information of a user, an apparatus for providing hair loss state information, and a method for selecting a scalp image for calculating hair loss diagnosis assistance information.

2. Discussion of Related Art

Hair loss refers to a state in which hair is not normally present at a region where it is to be present, and generally, hair loss refers to deterioration of hair in the scalp. Hair loss is a disease with a high prevalence, and when it occurs, it can cause problems such as psychologically negative effects on individuals, such as stress, lack of confidence, social avoidance, and depression, and can even lead to mental illness in severe cases. Due to the negative effects of the hair loss phenomenon, hair loss is recognized as a serious social problem, and accordingly, a market related to hair loss is steadily growing.

In order to diagnose and manage hair loss states and, if necessary, treat hair loss, it is essential to accurately determine how much hair loss has been progressed from an individual's head image.

However, the conventional method of determining hair loss states has been achieved by a method in which an individual visit a hospital or clinic directly and is observed by a naked eye. In this case, there is an inconvenience that a hospital or clinic must be directly visited for counseling or diagnosing for hair loss treatment, and there is a limitation in that it is difficult to obtain an objective determination result compared to a normal person regarding the current hair loss progress state.

Accordingly, there is a need for developing a method for easily determining and diagnosing hair loss states without a person visiting a local site.

Meanwhile, due to the improvement of the image segmentation technology, it is possible to segment an image to calculate a diagnosis assistance indicator related to various diseases, and the image analysis field has recently been attracting attention.

In particular, the technology of analyzing a scalp image to calculate assistance information for diagnosing hair loss has attracted attention. In the present technology, it is required to derive more accurate and objective hair loss diagnosis assistance information from a scalp image.

However, in the conventional scalp image analysis method, to calculate hair loss diagnosis assistance information, a scalp image to be analyzed was selected manually using a complex image filtering process or depending on the operator's vision. Accordingly, the conventional scalp image analysis method has a limitation in that it has to be confirmed whether each of a plurality of scalp images is suitable for an analysis criterion, and accordingly, the data amount increases and a data processing speed limitation exists.

In addition, in order to provide information on a scalp state through the analysis of a scalp image, a scalp image with a clear quality is required. However, in general, when a scalp image is photographed using a camera, since the camera is closely attached to a very close distance of the scalp, it is highly likely that an image that is not clear, for example, an image with a blurred focus is obtained. Therefore, it is an object of selecting a scalp image with a good quality from among a plurality of scalp images.

Accordingly, there is a need for developing a scalp image analysis system, a scalp image analysis device, and a scalp image analysis method that may select a scalp image to be analyzed as a scalp image with a high quality, and may accurately calculate information on a scalp.

SUMMARY OF THE INVENTION

An object of the present invention is to provide a method for providing hair loss state information and a device for providing hair loss state information.

An object of the present invention is to provide a scalp image analysis method, a scalp image analysis device, and a scalp image analysis system for providing hair loss diagnosis assistance information.

The present invention is not limited to the above-described objects, and those technical objects which are not mentioned will be clearly understood by those skilled in the art from the present specification and the accompanying drawings.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which:

FIG. 14 is a diagram for describing a method of selecting a matching boundary point according to another embodiment.

FIG. 18 is a flowchart for describing a method of determining a hair loss state of a user according to another embodiment.

FIG. 32 is a diagram illustrating an external structure and an internal structure of a scalp measuring device 1000 according to an embodiment of the present application.

FIG. 39 is a flowchart illustrating a process for acquiring pore region information according to an embodiment of the present application.

FIG. 44 is a diagram illustrating an aspect of acquiring quantitative information related to a pore region according to an embodiment of the present application.

FIG. 46 is a flowchart illustrating a method of selecting a target image according to another embodiment of the present application.

FIGS. 54 to 57 are diagrams illustrating an aspect of post processing according to an embodiment of the present application.

FIG. 61 is a flowchart of a method of calculating a hair loss progression indicator according to an embodiment of the present application.

FIG. 62 is a diagram illustrating an aspect of outputting hair loss diagnosis assistance information to a user according to an embodiment of the present application.

DETAILED DESCRIPTION OF EXEMPLARY EMBODIMENTS

Figure 1:
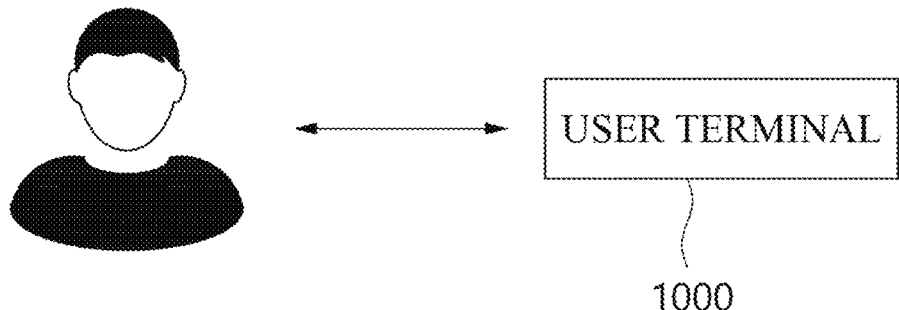
FIG. 1 is a diagram for describing a method of providing hair loss state information according to an embodiment.

The above-described objects, features, and advantages of the present application will become more apparent from the following detailed description related to the accompanying drawings. However, the present application may have various modifications and various embodiments, and specific embodiments will be described below in detail.

In the specification, like reference numerals generally indicate like elements. In addition, like elements within the same spirit ranges shown in the drawings of each embodiment will be described using like reference numerals, and redundant descriptions thereof will be omitted.

When it is determined that a detailed description of a known function or configuration related to the present application may unnecessarily obscure the subject matter of the present application, the detailed description thereof will be omitted. In addition, the numbers (e.g., first, second, and the like) used in the description process of the present specification are merely identifying symbols for distinguishing one element from another.

In addition, the suffix words "module" and "unit" for components used in the following embodiments are given or used interchangeably only in consideration of ease of writing the specification, and do not have a distinguishing meaning or role by itself.

In the following embodiments, the singular expression includes the plural expression unless the context clearly dictates otherwise.

In the following embodiments, the terms "include" or "have" mean that a feature or component described in the specification exists, and do not preclude the possibility that one or more other features or components are added.

In the drawings, for convenience of description, the elements may be exaggerated or reduced in size. For example, the size and thickness of each component shown in the drawings are arbitrarily illustrated for convenience of description, and the present invention is not necessarily limited to the illustrated case.

When some embodiments may be implemented differently, the order of a specific process may be performed differently from the order described. For example, two consecutively described processes may be performed substantially at the same time or may proceed in an order opposite to the order described.

In the following embodiments, when a component is connected, the case includes not only the case where the components are directly connected but also the case where the components are indirectly connected by intervening components there between.

For example, when a component is electrically connected, the case includes not only the case where the components are directly electrically connected but also the case where the components are indirectly electrically connected by intervening components there between.

According to an embodiment of the present application, there is provided a method of providing hair loss state information, the method comprising: obtaining a head image of a user; extracting a plurality of feature points from the head image, wherein the plurality of feature points include a first group of feature points and a second group of feature points; extracting a plurality of boundary points corresponding to a boundary line of a hair and a forehead of the user from the head image; selecting a matching boundary point corresponding to the first group of feature points from among the plurality of boundary points; obtaining a upper face portion calculation value determined based on a distance between the first group of feature points and a matching boundary point corresponding to the first group of feature points with respect to a first axis on the head image; obtaining a middle lower face portion calculation value determined based on a distance between the first group of feature points and the second group of feature points with respect to the first axis; and providing hair loss state information of the user based on a ratio of the upper face portion calculation value and the middle lower face portion calculation value.

According to an embodiment of the present application, the plurality of boundary points may be extracted based on a probability value corresponding to a boundary line of a hair and a forehead of the user, and the selecting of the matching boundary point may include: setting a matching area between a first straight line and a second straight line extending in a first axis direction and a second axis direction, respectively, from a first point and a second point corresponding to the first group of feature points; and selecting at least one of matching candidate boundary points having a probability value greater than or equal to a predetermined threshold value from among a plurality of boundary points included in the matching area as the matching boundary point, wherein the first point and the second point may be points separated from the first group of feature points by a first distance and a second distance in a second axis direction orthogonal to the first axis, respectively.

According to an embodiment of the present application, the matching boundary point may be a point located farthest in a first direction of the first axis from the first group of feature points among the matching candidate boundary points.

According to an embodiment of the present application, the upper face portion calculation value may include a upper face portion area value of the head image set based on the first group of feature points and the matching boundary point, and the middle lower face portion calculation value may include a middle lower face portion area value of the head image set based on the first group of feature points and the second group of feature points.

According to an embodiment of the present application, the selecting of the matching boundary point may include: selecting a plurality of feature points including at least a first feature point and a second feature point from among the first group of feature points; and selecting a first matching boundary point and a second matching boundary point corresponding to the first feature point and the second feature point, respectively, wherein the providing of the hair loss state information may include: extracting a first reference point corresponding to the first feature point and a second reference point corresponding to the second feature point from the head image, wherein the first reference point and the second reference point are points separated from the first feature point and the second feature point by a distance of a predetermined ratio of the middle lower face portion calculation value in a first direction of the first axis, respectively; obtaining a first upper face portion area value determined based on the first feature point, the second feature point, the first matching boundary point, and the second matching boundary point; calculating a second upper face portion area value based on the first feature point, the second feature point, the first reference point, and the second reference point; and providing hair According to an embodiment of the present application, the providing of the hair loss state information of the user may include providing information on a treatment area in which the user's treatment is required in the image, and the treatment area may be determined based on a difference between the first upper face portion area value and the second upper face portion area value.

According to an embodiment of the present application, the first upper face portion area value and the second upper face portion area value may be calculated based on a reference horizontal length and a vertical length of the user's face, and the reference horizontal length may be determined based on an aspect ratio of the user's face and a preset standard face length.

According to an embodiment of the present application, the providing of the hair loss state information of the user may include obtaining information on a hair treatment amount input from the user or a third party and outputting a forehead area after the user's treatment according to the hair treatment amount.

According to an embodiment of the present application, the plurality of boundary points may be obtained using a neural network model, and the neural network model may be trained to obtain a plurality of reference boundary points corresponding to the boundary lines of the hair and the forehead based on a training head image including at least a portion of boundaries of the hair and the forehead.

According to an embodiment of the present application, the neural network model may include a first portion for obtaining a region of interest including the hair and the forehead based on the training head image and a second portion for obtaining the plurality of reference boundary points based on the region of interest.

According to an embodiment of the present application, a program stored in a computer-readable recording medium for executing a method of providing hair loss state information, the method including: obtaining a head image of a user; extracting a plurality of feature points from the head image, wherein the plurality of feature points include a first group of feature points and a second group of feature points; extracting a plurality of boundary points corresponding to the boundary lines of the hair and the forehead of the user from the head image;

According to an embodiment of the present application, selecting a matching boundary point corresponding to the feature point of the first group from among the plurality of boundary points; obtaining a upper face portion calculation value determined based on a distance between the feature point of the first group and the matching boundary point based on a first axis on the head image; obtaining a middle lower face portion calculation value determined based on a distance between the feature point of the first group and the feature point of the second group based on the first axis; and providing hair loss state information of the user based on a ratio of the upper face portion calculation value and the middle lower face portion calculation value.

Hereinafter, a hair loss state information providing apparatus, a hair loss state information providing system, and a method of providing hair loss state information of the present application will be described with reference to the drawings.

Figure 2:
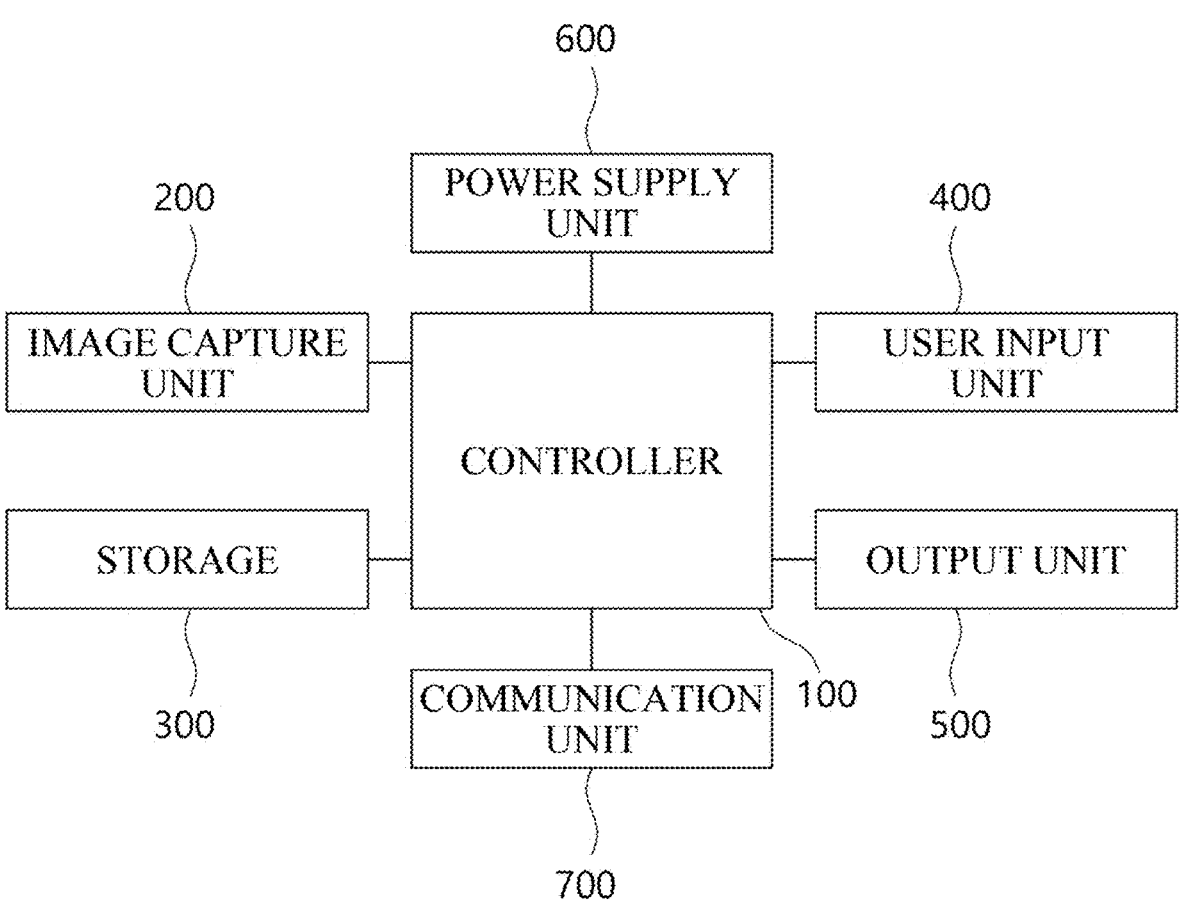
FIG. 2 is a diagram for describing a configuration of a user terminal.

FIG. 1 is a diagram for describing a method of providing hair loss state information according to an embodiment, and FIG. 2 is a diagram for describing a configuration of a user terminal.

Referring to FIG. 1, a method of providing hair loss state information according to an embodiment may be performed through a user terminal 1000. Referring to FIG. 2, the user terminal 1000 may include a controller 100, an image capture unit 200, a storage 300, a user input unit 400, an output unit 500, a power supply unit 600, and a communication unit 700. In this case, the user terminal 1000 may include a portable information communication device, for example, a smartphone, a tablet, and the like.

The image capture unit 200 is a digital camera and may include an image sensor and an image processing unit. An image sensor is a device that converts an optical image into an electrical signal, and may be composed of a chip in which a plurality of photo diodes are directly incorporated. For example, the image sensor may include a charge coupled device (CCD), a complementary metal oxide semiconductor (CMOS), or the like. Meanwhile, the image processor may generate image information by image-processing the captured result.

The storage 300 is a storage means for storing data readable by a microprocessor, and may include a hard disk drive (HDD), a solid state disk (SSD), a silicon disk drive (SDD), a read-only memory (ROM), a random access memory (RAM), a CD-ROM, a magnetic tape, a floppy disk, and an optical data storage device. The storage 300 may store data received in the user terminal 1000.

The user input unit 400 receives a user input to the user terminal 1000. The received input may be transmitted to the controller 100. According to an embodiment, the user input unit 400 may receive a user input through a touch display. In addition, the user input unit 400 may refer to a user interface screen in which a command is input from a user.

The output unit 500 outputs various types of information according to a control command of the controller 100. According to an embodiment, the output unit 500 may output information through a display panel. More specifically, the output unit 500 may output information related to a hair loss state of the user through the display panel. However, the output unit 500 is not limited to the display panel, and may include various means capable of outputting information such as a speaker.

The power supply 600 may include a battery, and the battery may be embedded in the user terminal 1000 or may be provided to be detachable from the outside. The power supply 600 may supply power required by each component of the user terminal 1000.

The communication unit 700 may include a wireless communication module and/or a wired communication module. Here, the wireless communication module may include a Wi-Fi communication module, a cellular communication module, or the like.

The controller 100 may include at least one processor. In this case, each processor may execute at least one instruction stored in the memory, thereby executing a predetermined operation. Specifically, the controller 100 may control the overall operation of the components included in the user terminal 1000. In other words, the user terminal 1000 may be controlled or operated by the controller 100.

Meanwhile, although not shown in FIG. 2, the user terminal 1000 may include various sensors. For example, the user terminal 1000 may include a gyro sensor, a temperature sensor, a motion sensor, a touch sensor, a proximity sensor, or the like.

According to an embodiment of the present application, the user may be provided with information about a hair loss state of the user, for example, whether or not a hair loss progresses, a degree of hair loss progresses, a hair loss type, a hair transplantation simulation, or the like through the user terminal 1000. For example, the user may capture his or her head image through the image capture unit 200 provided in the user terminal 1000, and then receive information about the hair loss state of the user through the output unit 500.

As a more specific example, the user terminal 1000 may acquire the user's head image captured through the image capture unit 200, and then acquire information related to the hair loss state of the user using a pre-trained neural network model, and provide the information to the user through the output unit 500. A more detailed method of acquiring information related to the hair loss state of the user by the user terminal 1000 will be described below.

Figure 3:
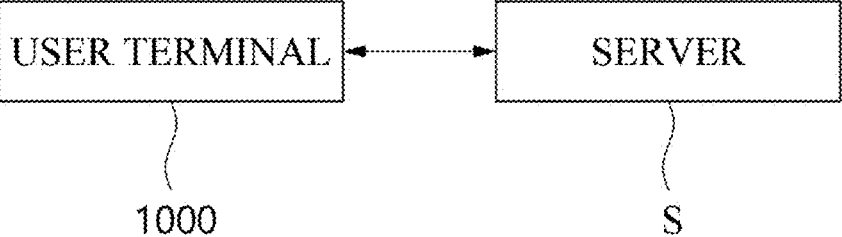
FIG. 3 is a diagram for describing a system for providing hair loss state information according to an embodiment.

FIG. 3 is a diagram for describing a hair loss state information providing Referring to FIG. 3, the hair loss state information providing system may include a user terminal 1000 and a server S.

According to an embodiment, the server S may perform learning of a neural network model for outputting hair loss state information of a user based on a user's head image. The user terminal 1000 may receive information on the trained neural network model from the server S. In this case, the user terminal 1000 may perform a series of operations for providing hair loss state information of the user using the trained neural network model received from the server S. More specifically, the user terminal 1000 may acquire a user's head image and generate information on a hair loss state of the user based on the acquired head image. In addition, the user terminal 1000 may provide information on a hair loss state of the user to the user.

According to another embodiment, the aforementioned series of operations for determining hair loss state information of the user may be performed by the server S. That is, the server S may acquire a user's head image from the user terminal 1000. Thereafter, the server S may determine a hair loss state of the user from the head image using the trained neural network model. In addition, the server S may transmit a result of determining the hair loss state of the user to the user terminal 1000. In this case, the user terminal 1000 may provide the result of determining the hair loss state of the user to the user.

Meanwhile, the user terminal 1000 described above with reference to FIG. 3 may be a diagnosis device. In this case, the series of operations performed by the user terminal 1000 may be performed in the same manner as or correspondingly to the diagnosis device.

For example, the diagnosis device may receive information on the trained neural network model from the server S. In this case, the diagnosis device may perform a series of operations for providing hair loss state information of the user using the trained neural network model received from the server S.

As another example, the diagnosis device may transmit the user's head image to the server S. Thereafter, the server S may determine the hair loss state of the user from the head image using the trained neural network model and transmit the result to the diagnosis device.

Meanwhile, the diagnosis device may be, for example, a scalp state measuring device used in a hospital, a clinic, or the like. Alternatively, the diagnosis device may be a device used to diagnose a hair loss state of a patient in a hospital, a clinic, or the like, but is not limited thereto, and may include various known medical instruments or devices.

Hereinafter, operations performed in the user terminal 1000 are described for convenience of description, but operations corresponding to or the same may be performed in the diagnosis device according to an implementation example.

The user terminal 1000 may utilize a user's head image to determine a hair loss state of the user. Hereinafter, a method of acquiring a head image by the user terminal 1000 will be described, and the acquired head image will be described in detail with reference to the drawings.

The user terminal 1000 may acquire the user's head image through the image capture unit 200 of FIG. 2.

When the user photographs his or her head through the image capture unit 200, the user terminal 1000 may display a photographing guide through the output unit 500. The photographing guide may relate to a contour line of a person's head or face, but is not limited thereto, and may include various known forms of photographing guides.

When the user photographs the head based on the photographing guide, if the head is positioned satisfying a predetermined criterion in the photographing guide, the controller 100 of the terminal may activate the photographing button to allow the user to photograph and store the head.

In this case, the predetermined criterion may be determined based on whether the user's head is located intact in the photographing guide. Preferably, the predetermined criterion may be determined based on whether the entire face including the user's hair is located in the photographing guide. As another example, the predetermined criterion may relate to whether a specific portion of the user's head, for example, a boundary portion of the hair and the forehead, is located in the photographing guide.

Meanwhile, as described above, the user terminal 1000 may include a gyro sensor. In this case, the predetermined criterion may be related to the degree of inclination of the user More specifically, the controller 100 of the user terminal 1000 may acquire the tilting information of the user terminal 1000 through the gyro sensor. Thereafter, the controller 100 may control the image capture unit 200 to capture the head image based on the tilting information. For example, the controller 100 may allow the image capture unit 200 to capture a head image only when the degree of tilting of the user terminal 1000 is equal to or less than a predetermined level.

Figure 4:
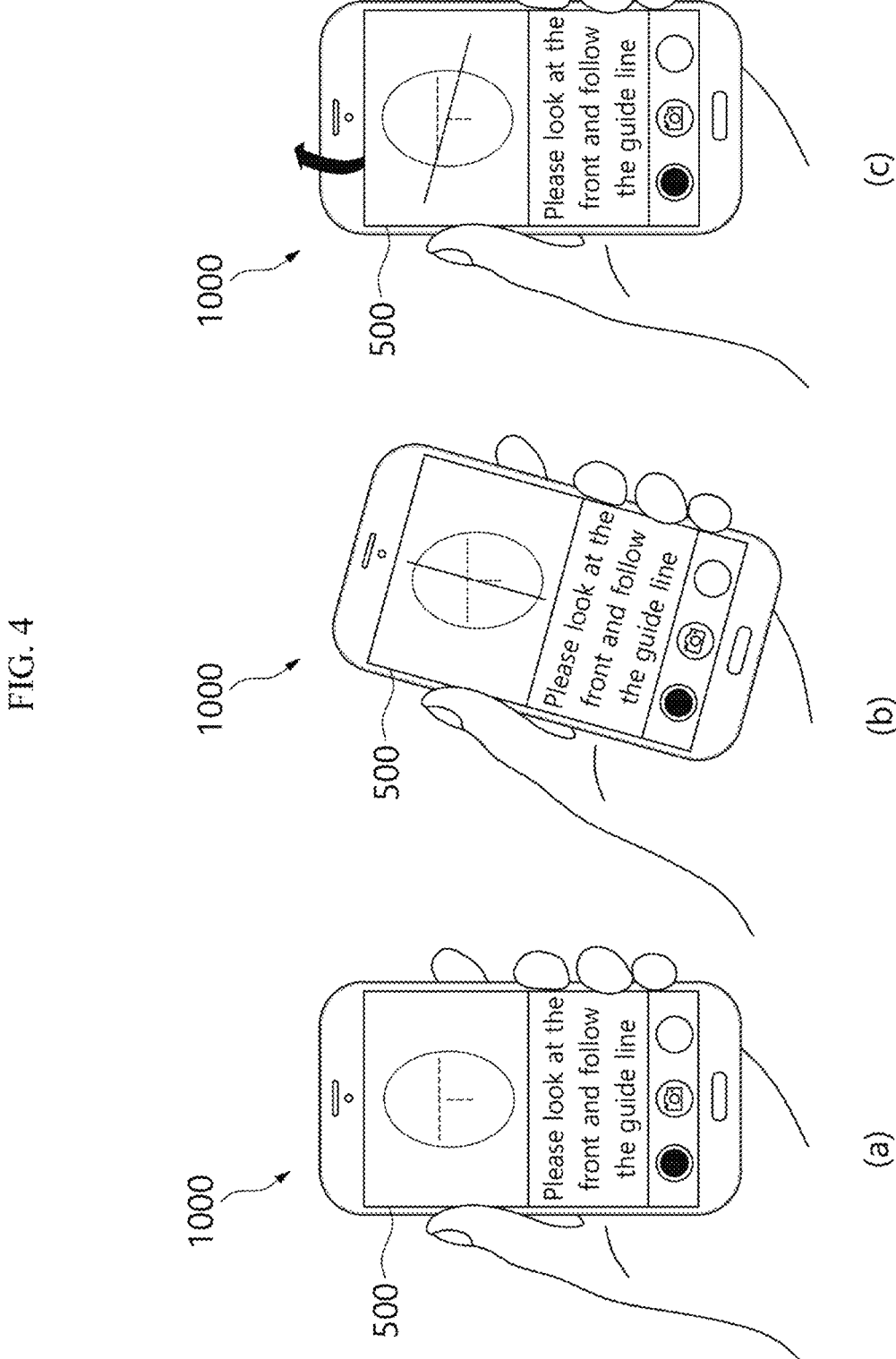
FIG. 4 is a diagram for exemplarily describing an operation of photographing a user's head through an image capture unit.

FIG. 4 is a diagram for exemplarily describing an operation of photographing a user's head through an image capture unit. Referring to FIG. 4, the user terminal 1000 may output a photographing guide message through the output unit 500.

FIG. 4A is a diagram illustrating a case in which the degree of tilting left and right or front and back of the user terminal 1000 satisfies a predetermined criterion. On the other hand, FIG. 4B is a diagram illustrating a case where the user terminal 1000 is inclined to the left and right, and FIG. 4C is a diagram illustrating a case where the user terminal 1000 is inclined to the front and back.

As shown in FIG. 4A, when the degree of tilting of the user terminal 1000 satisfies a predetermined criterion, the controller 100 of the user terminal 1000 may activate a photographing button of the image capture unit 200. However, when the user terminal 1000 is inclined left and right or front and back as shown in FIG. 4B or FIG. 4C, the user terminal 1000 may activate the photographing button after deactivating the photographing button of the image capture unit 200 and activate the photographing button when the degree of inclination of the terminal is equal to or less than a predetermined level.

Figure 5:
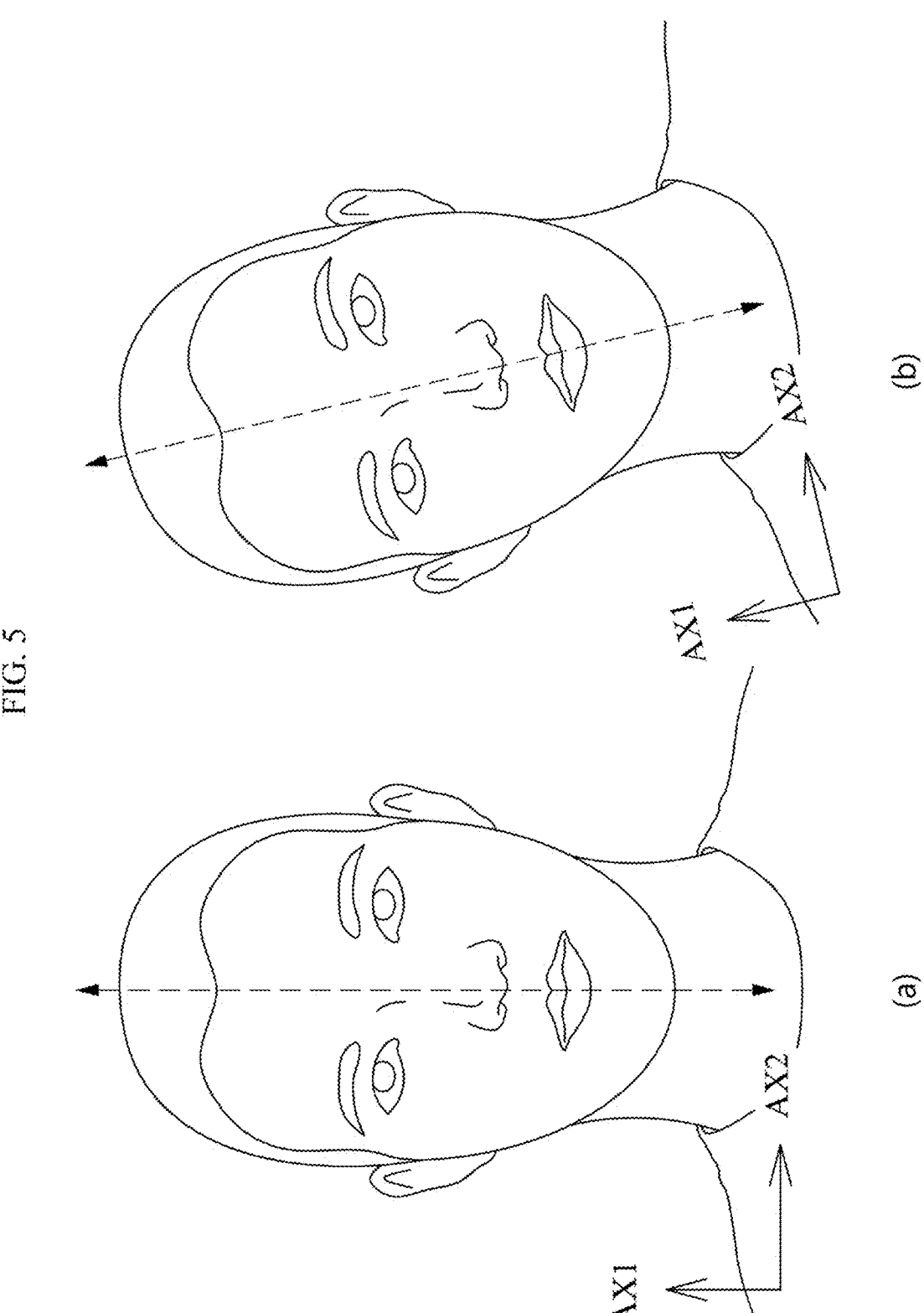
FIG. 5 is a diagram illustrating a user's head image acquired through an image capture unit.

FIG. 5 is a diagram illustrating a user's head image acquired through an image capture unit. The head image acquired by the image capture unit 400 may be transmitted to the Referring to FIG. 5, the head image may be an image in which all or a portion of the user's head is captured.

For example, when the head image is an image in which all of the user's head is captured, the head image may be an image including all of the user's face including hair. Alternatively, the head image may be an image including all the outline of hair, forehead, and face. Alternatively, the head image may be an image including all major portions of the face.

As another example, when the head image is an image captured by a part of the user's head, the head image may be an image captured by at least the user's hair and forehead.

Alternatively, the head image may be an image in which at least a part of the user's hair and at least a part of the forehead are captured. Alternatively, the head image may be an image including at least one of a main portion constituting the user's face. In this case, the main portion may be a body organ such as an eye, a nose, a mouth, an ear, or a specific portion of the face such as a forehead, a middle rice, a ball, a jaw, or the like.

As another example, the head image may be an image related to a front surface, a left side surface, or a right side surface of the user's head. In this case, the image related to the front surface of the user's head may be a facial image of the user including at least one of the eye, the nose, and the mouth of the user. The image related to the left side surface and the right side surface of the user's head may be a side image of the user's head including at least a part of the user's forehead.

The head image may be an image in which the subject does not move, or may be a video in which the subject moves. In this case, when the head image is a video, the video may include a plurality of images in which the front surface, the left side surface, and/or the right side surface of the user's head are captured. Alternatively, the video may mean a video in which the user's hair and the boundary area of the forehead are all captured.

Meanwhile, a first axis AX1 and a second axis AX2 for indicating a specific coordinate may be defined on the head image.

According to an embodiment, the first axis AX1 and the second axis AX2 may mean a y-axis and an x-axis on the image, respectively. For example, the head image may be an image captured in a state in which the user's head is not inclined as shown in FIG. 5(a). In this case, the first axis AX1 may correspond to the y-axis on the image. In addition, the second axis AX2 may correspond to the x-axis on the image. In this case, the second axis AX2 may be an axis orthogonal to the first axis AX1.

According to another embodiment, the first axis AX1 and the second axis AX2 may be defined corresponding to a degree to which the user's head is inclined on the head image. For example, the head image may be an image captured in a state in which the user's head is inclined left and right as shown in FIG. 5(b). When it is determined that the user's head is inclined by an angle a with respect to the y-axis in the head image as shown in FIG. 5(b), the first axis AX1 may be defined as an axis inclined by a with respect to the y-axis, and the second axis AX2 may be defined as an axis inclined by a with respect to the x-axis.

The head image may be divided into a plurality of regions. According to an embodiment, the head image may be divided into two regions. For example, the head image may be divided into an upper region and a lower region of the face. Alternatively, the head image may be divided into a forehead region and a lower region of the face. Alternatively, the head image may be divided into a upper face portion and a middle-lower face portion. However, embodiments of the present application are not limited thereto, and the Hereinafter, for convenience of description, two regions on the head image are defined as upper face portion and middle-lower face portion, respectively, and then explained.

In this case, the criterion for dividing the head image into two regions may be determined based on the user's eyebrows. For example, the upper face portion may mean an upper portion based on the eyebrow, and the middle-lower face portion may mean a lower portion of the eyebrow.

According to another embodiment, the head image may be divided into three regions. For example, the head image may be divided into an upper region, a middle region, and a lower region. Alternatively, the head image may be divided into a forehead region, a nose region, and a lip region. Alternatively, the head image may be divided into upper face portions, middle face portions, and lower face portions. However, the embodiment of the present application is not limited thereto, and the head image may be classified by various terms that may divide one region into three regions. Hereinafter, for convenience of description, three regions on the head image are defined as upper face portions, middle face portions, and lower face portions, respectively, and then explained.

In this case, the criterion for dividing the head image into three areas may be determined based on the user's eyebrows and lips. For example, the upper face portion may mean a region of an upper portion of the eyebrows, the middle face portion may mean a region from a lower portion of the eyebrows to an upper portion of the lip, and the lower face portion may mean a region from a lower portion of the lip, but is not limited thereto.

Figure 6:
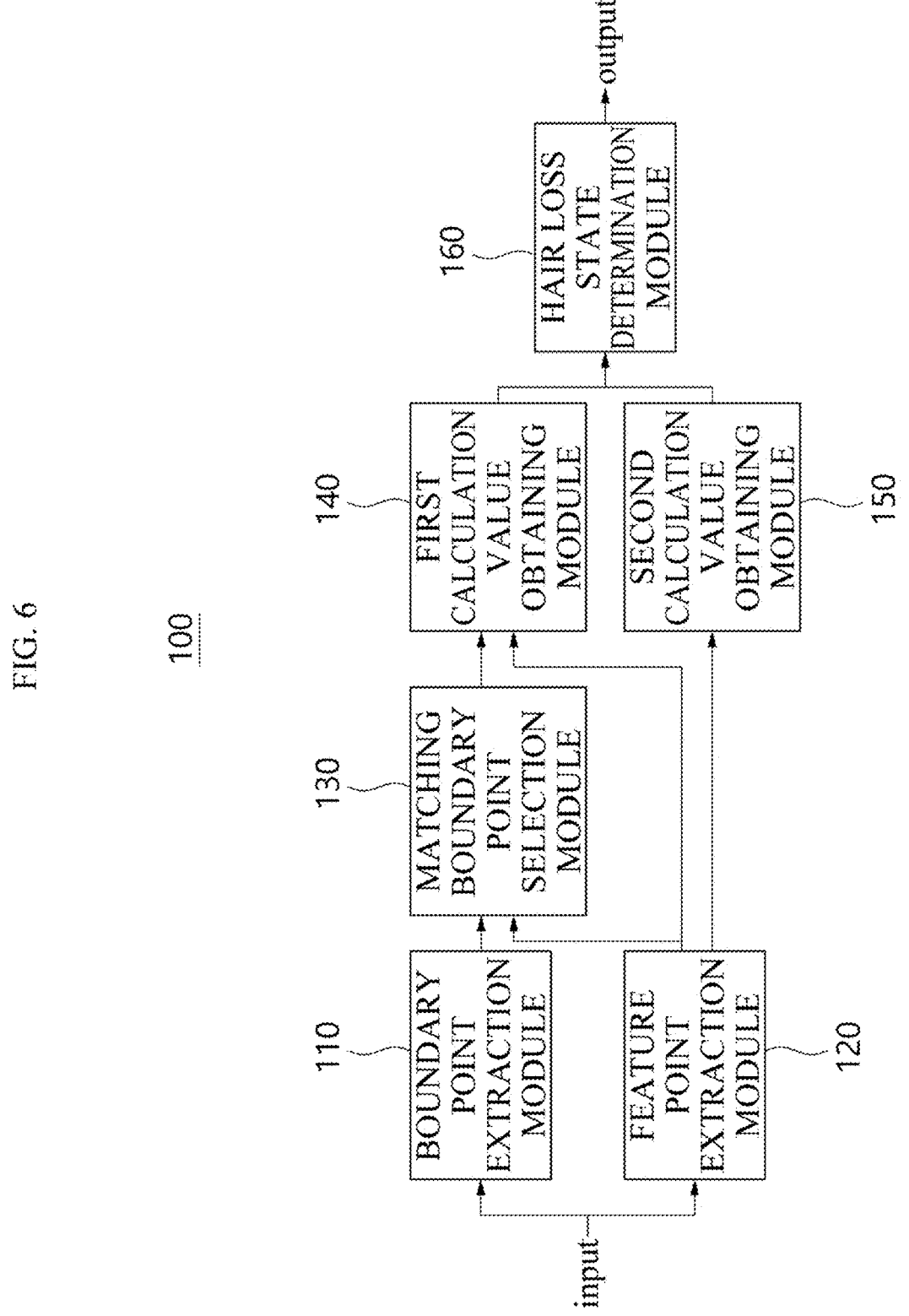
FIG. 6 is a diagram for describing a module included in a controller of a user terminal described with reference to FIGS. 1 to 3 and an operation thereof.

FIG. 6 is a diagram for describing a module included in the controller of the user terminal described with reference to FIG. 1 to 3 and an operation thereof.

The controller 100 may determine the hair loss state of the user based on the user's head image acquired by the image capture unit 200 of the user terminal 1000. More specifically, the controller 100 may receive the user's head image described with reference to FIGS. 4 and 5 and determine the user's hair loss based on the received image. Hereinafter, a function performed by each module included in the controller 100 in determining the hair loss state of the user will be described.

Referring to FIG. 6, the controller 100 may include a boundary point extraction module 110, a feature point extraction module 120, a matching boundary point selection module 130, a first calculation value obtaining module 140, a second calculation value obtaining module 150, and a user hair loss state determination module 160.

The boundary point extraction module 110 may extract the boundary point BP from the head image. In addition, the feature point extraction module 120 may extract the feature point FP from the head image. The matching boundary point selection module 130 may select a matching boundary point MBP from the boundary point BP based on the feature point FP.

The first calculation value obtaining module 140 may obtain the first calculation value based on the feature point FP and the matching boundary point MBP. In addition, the second calculation value obtaining module 150 may obtain the second calculation value based on the feature point FP. The user hair loss state determination module 160 may perform a determination on the user's hair loss state, for example, whether hair loss progresses, hair loss progresses, hair loss types, etc., based on the first calculated value and the second calculated value.

Meanwhile, the modules shown in FIG. 6 are sub-components of the controller 100, and may be integrated and performed through one or a plurality of processors according to an embodiment. Hereinafter, operations of each module included in the controller 100 will be described in detail with reference to the drawings.

Figure 7:
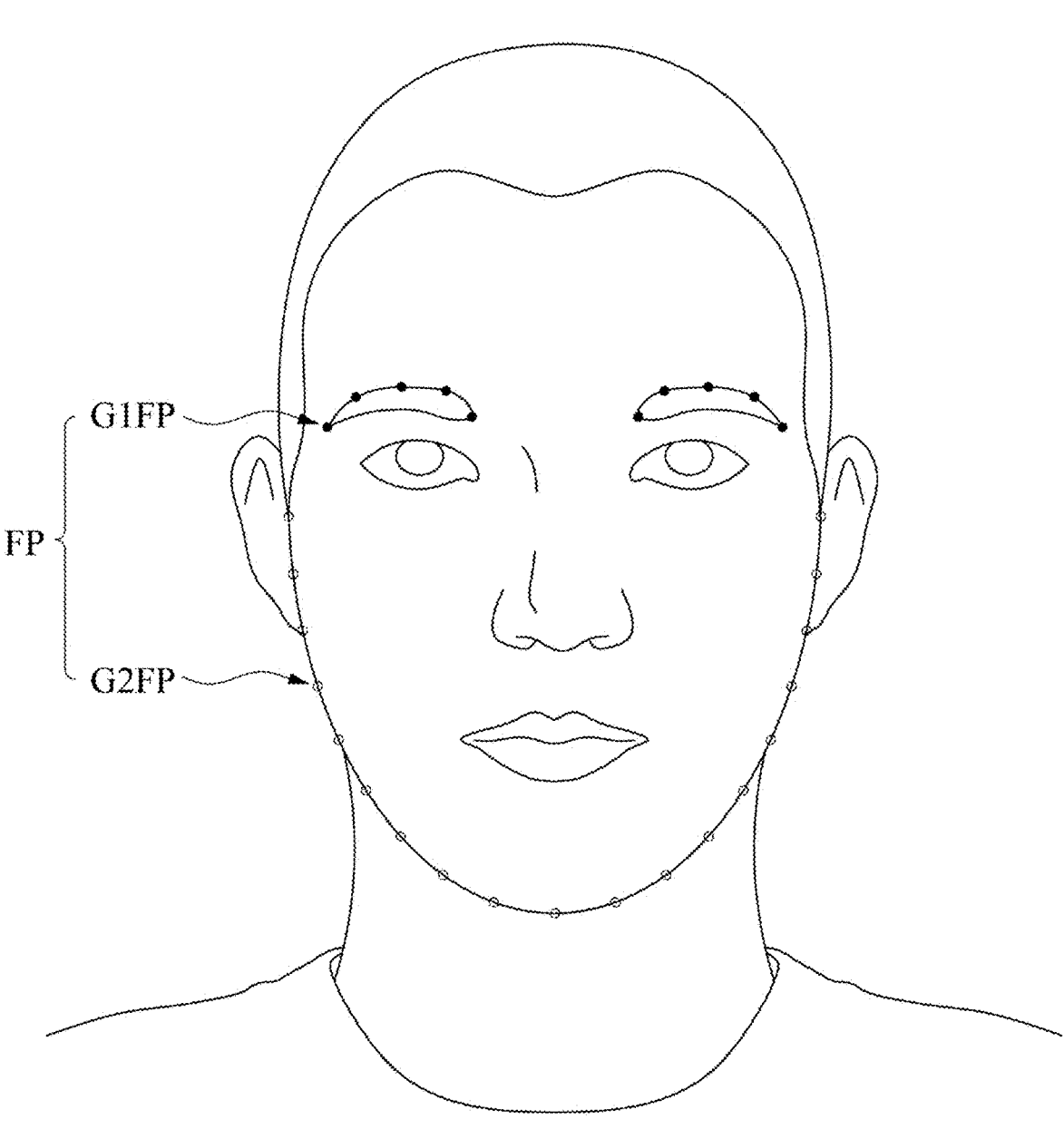
FIG. 7 is a diagram for describing a feature point extracted from a head image.

FIG. 7 is a diagram for describing a feature point extracted from a head image. Hereinafter, a method of extracting a feature point FP from a head image will be understood with reference to FIG. 7.

The feature point FP may represent a landmark related to a major portion of a face. Here, the major portion of the face may include a body organ (e.g., eyes, eyebrows, nose, mouth, ears, and the like) constituting the face or a specific portion of the face (e.g., forehead, rice, balls, jaws, contours of the face, and the like).

Referring to FIG. 6, the feature points FP may be classified into a feature point of a first group G1FP and a feature point of a second group G2FP. In this case, the feature point of the first group G1FP and the feature point of the second group G2FP may each include one or more feature points.

For example, the feature point of the first group G1FP may represent a landmark related to a major portion of the face located above a predetermined point, position, or portion in the longitudinal direction of the face. In addition, the feature point of the second group G2FP may represent a landmark related to a major portion of the face located below a predetermined point, position, or portion in the longitudinal direction of the face. Meanwhile, the feature point of the second group G2FP may be located at a lower than the feature point of the first group G1FP in the longitudinal direction of the face on the head image.

As another example, the feature point of the first group G1FP may represent a landmark corresponding to a first major portion of the face, and the feature point of the second group G2FP may represent a landmark corresponding to a second major portion of the face. In this case, the first major portion and the second major portion of the face may be different from each other. For example, the feature point of the first group G1FP may represent a landmark corresponding to eyebrows, and the feature point of the second group G2FP may represent a landmark corresponding to a contour line (e.g., a jaw line) of the face. Alternatively, the first major portion and the second major portion of the face may be the same as each other. For example, the feature point of the first group G1FP may represent a landmark corresponding to a left eyebrow of the face, and the feature point of the second group G2FP may represent a landmark corresponding to a right eyebrow of the face.

The feature point extraction module 120 may extract a plurality of feature points FP from a head image captured through the image capture unit 200. More specifically, the feature point extraction module 120 may extract the feature point FP from the head image using a preset algorithm. Here, the algorithm may mean a computer algorithm that automatically detects a landmark corresponding to a major portion of the face from the face image, but is not limited thereto, and may include various known face detection algorithms.

According to an embodiment, the user terminal 1000 may store software related to the above-described algorithm. In this case, the user terminal 1000 may extract the feature point FP from the head image according to the stored algorithm.

According to another embodiment, the software related to the above-described algorithm may be stored in the server S. In this case, the user terminal 1000 may extract the feature point FP from the head image by a method of transmitting and receiving data in real time through the server S.

Figure 8:
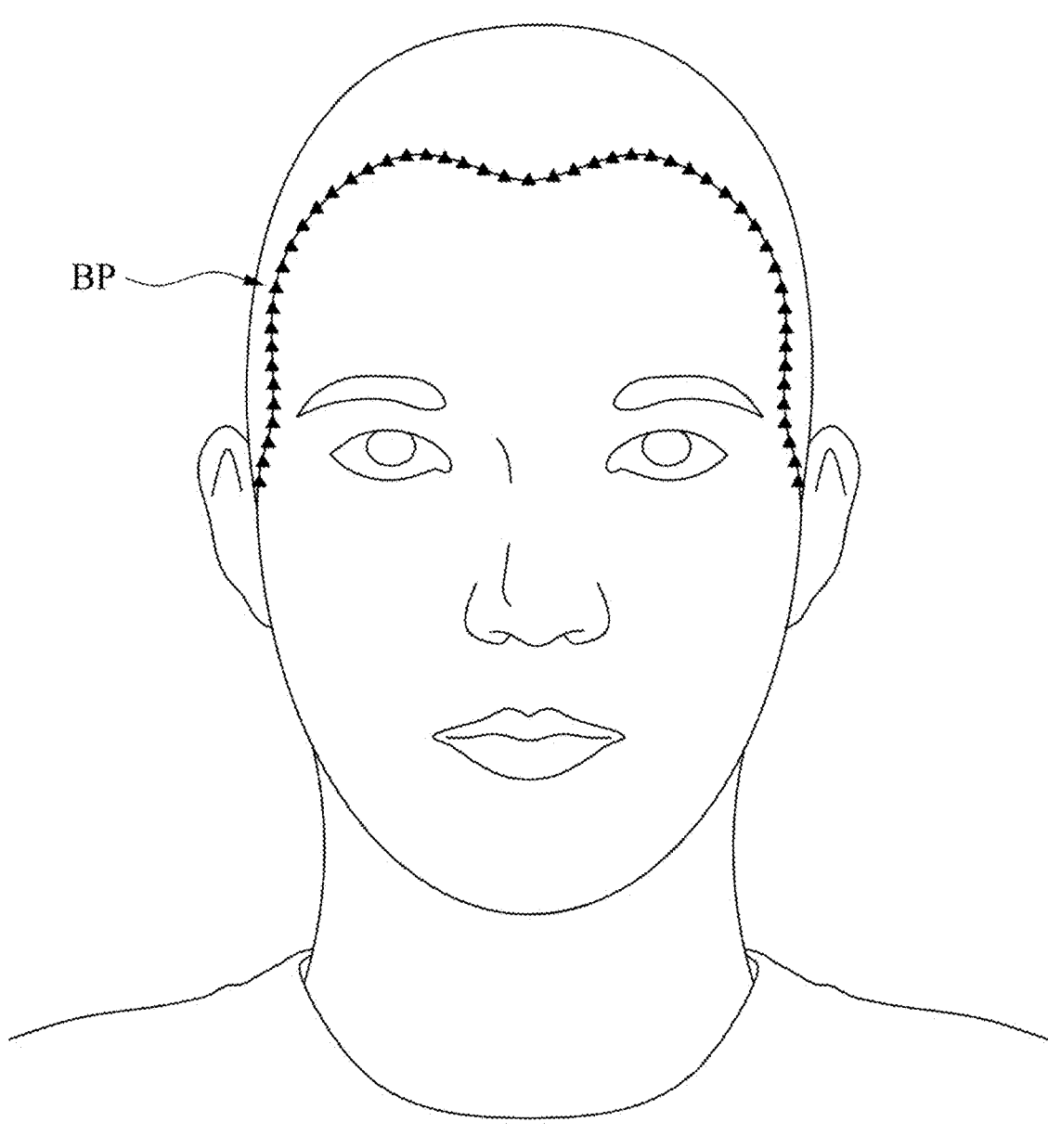
FIGS. 8 and 9 are diagrams for describing a boundary point extracted from a head image.
Figure 9:
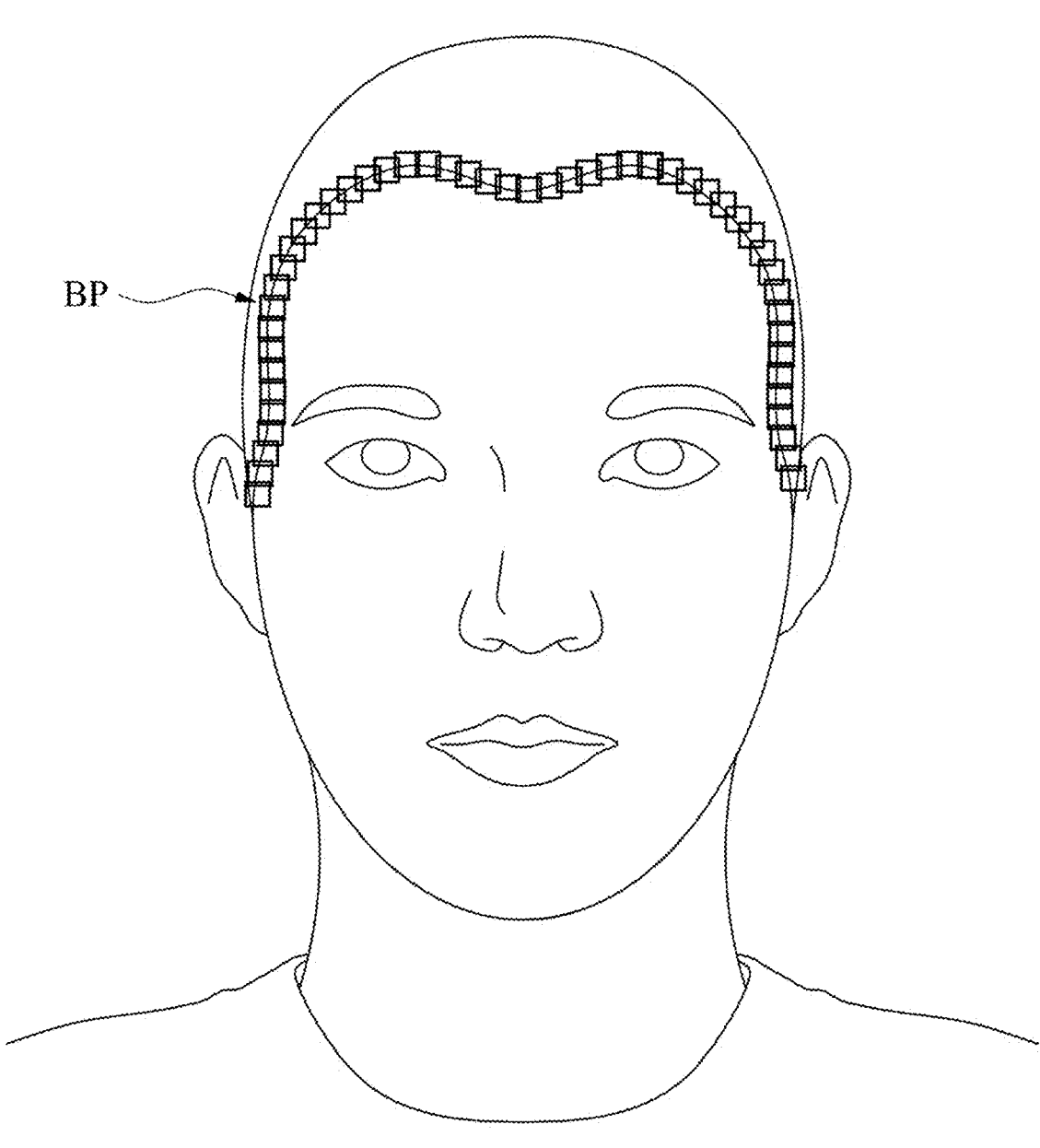

FIGS. 8 and 9 are diagrams for describing a boundary point extracted from the head image. Hereinafter, a method of extracting a plurality of boundary points BP from the head image will be understood with reference to FIGS. 8 and 9.

Referring to FIG. 8, the boundary point BP may be a point included in a boundary region of a hair and a forehead. Alternatively, the boundary point BP may be a plurality of points corresponding to a boundary line of the hair and the forehead. More specifically, the boundary point BP may mean a pixel having a probability value of being a boundary point of the hair and the forehead among a plurality of pixels constituting the user's head image equal to or greater than a predetermined reference. According to an embodiment, the probability of corresponding to the boundary point of the hair and the forehead may be determined by a pre-trained neural network model.

According to an embodiment, the boundary point BP may be extracted based on a pixel corresponding to a boundary of the hair and the forehead as shown in FIG. 8. In this case, the boundary point BP may be extracted based on a segmentation image for a region including the hair and the forehead.

According to another embodiment, the boundary point BP may be extracted based on a region corresponding to a boundary of the hair and the forehead as shown in FIG. 9. In this case, one or more bounding boxes corresponding to the boundary region may be obtained in the region including the hair and the forehead. Then, the boundary point extraction module 110 may extract a point of a preset position in the obtained bounding box as the boundary point. In this case, the preset position may be any one of an intermediate point or a corner of the bounding box.

Figure 10:
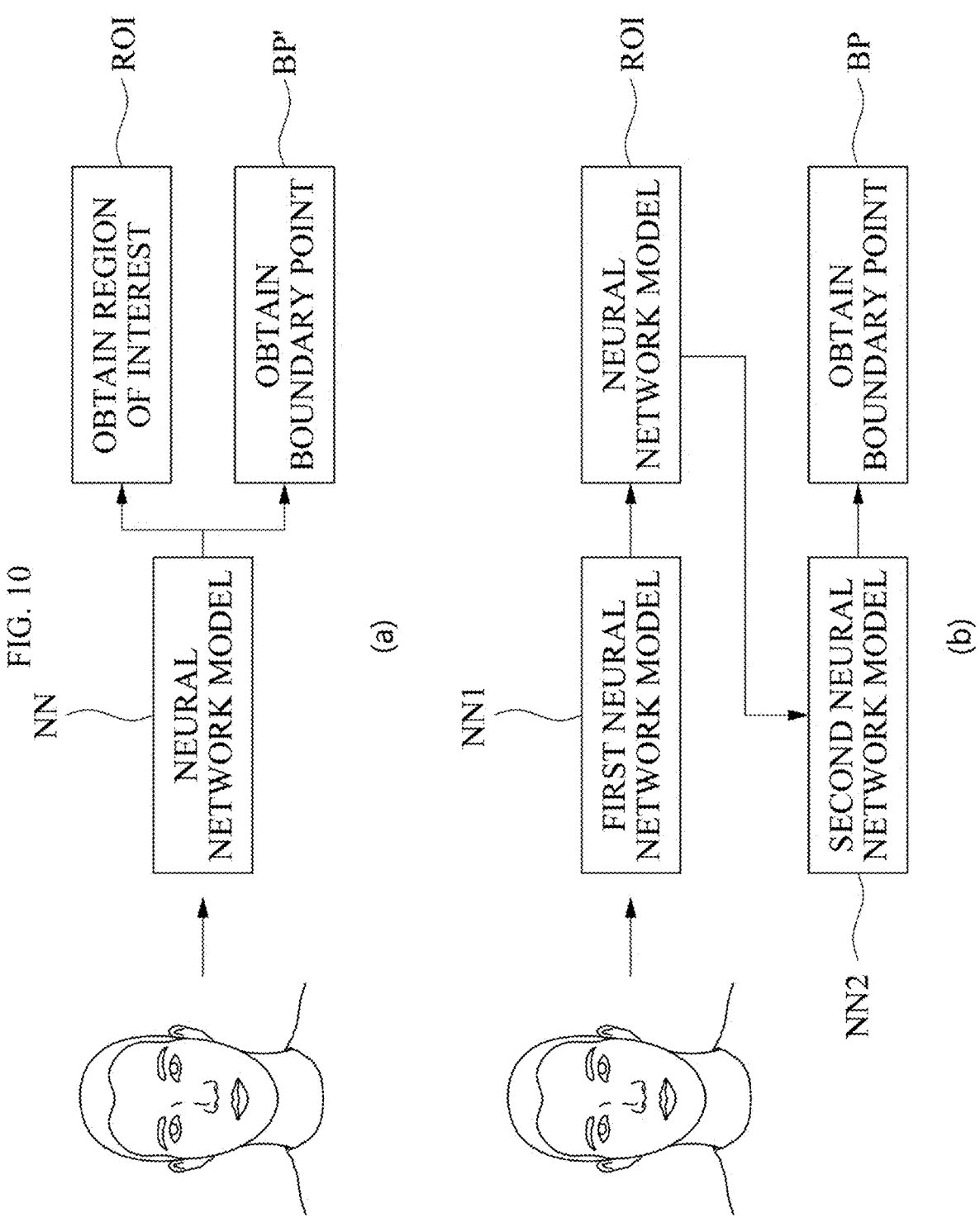
FIG. 10 is a diagram illustrating an embodiment of a structure of a neural network for obtaining a boundary point from a head image.

FIG. 10 illustrates an embodiment of a structure of a neural network for obtaining a boundary point from a head image. Hereinafter, a method of extracting a boundary point BP from a head image through a pre-trained artificial neural network will be described with reference to FIG. 10.

Referring to FIG. 10, the boundary point extraction module 110 may extract the boundary point BP from the head image through a pre-trained neural network model.

Referring to (a) of FIG. 10, according to an embodiment, the boundary point extraction module 110 may extract a plurality of boundary points BP from the head image using one neural network model NN. The neural network model NN may be trained to obtain a region of interest ROI and a boundary point BP' by receiving the head image. In this case, the region of interest ROI may mean a region including a boundary of the hair and the forehead and at least a portion of the hair and the forehead around the boundary.

The neural network model NN may be trained using training data including the head image and labeling data. In this case, the labeling data may include a first labeling value corresponding to the region of interest ROI. In addition, the labeling data may include a second labeling value corresponding to the boundary point.

Specifically, the neural network model NN may obtain an output value after receiving the head image. Then, the neural network model NN may be trained by a method of updating the neural network model NN based on an error value calculated by taking into account a difference between the output value In this case, the output value may include a first output value corresponding to the first labeling value and a second output value corresponding to the second labeling value.

The boundary point extraction module 110 may obtain the region of interest (ROI) and the boundary point (BP') by using the neural network model NN. Then, the boundary point extraction module 110 may finally extract only a point located within the region of interest ROI among the obtained boundary points BP' as the boundary points BP.

Specifically, the boundary point BP' obtained through the neural network model NN may include both a boundary point located within the region of interest ROI and a boundary point located outside the region of interest ROI. In this case, the boundary point BP that the boundary point extraction module 110 finally extracts may mean only a point located within the region of interest ROI among the boundary points BP' obtained through the neural network model NN.

Referring to FIG. 10(*b*), according to another embodiment, the boundary point extraction module 110 may extract a plurality of boundary points BP from a head image by using a plurality of neural network models, for example, two neural network models NN1 and NN2. The first neural network model NN1 may be trained to obtain a region of interest (ROI) by receiving a head image. In addition, the second neural network model NN2 may be trained to obtain a boundary point BP by receiving an ROI. At this time, the region of interest ROI is as described above with reference to FIG. 10(*a*).

The first neural network model NN1 and the second neural network model NN2 may mean separate neural network models independently, but are not limited thereto, and may be physically or logically separated from one neural network model. That is, a first portion of the neural network model may be trained to obtain a region of interest (ROI) from the head image, and a second portion may be trained to obtain a boundary point (BP) from the region of interest (ROI).

The first neural network model NN1 may be trained using learning data including a head image and labeling data. In this case, the labeling data may include a labeling value corresponding to a boundary between hair and forehead and a region including at least a portion of hair and forehead around the boundary. Specifically, the first neural network model NN1 may obtain an output value after receiving the head image. Then, the first neural network model NN1 may be trained as a method of updating the first neural network model NN1 based on an error value calculated by considering a difference between an output value and labeling data.

The second neural network model NN2 may be trained using learning data including images and labeling data regarding the region of interest (ROI). In this case, the labeling data may include a labeling value corresponding to a boundary point between the hair and the forehead. Specifically, the second neural network model NN2 may obtain an output value after receiving an image about the region of interest ROI. Then, the second neural network model NN2 may be learned by updating the second neural network model NN2 based on an error value calculated by considering a difference between the output value and the labeling data.

In other words, the boundary point extraction module 110 may obtain the region of interest (ROI) from the head image using the first neural network model NN1, and obtain the boundary point BP from the region of interest (ROI) using the second neural network model NN2. For example, the boundary point extraction module 110 may obtain the boundary point BP by using the second neural network model NN2, using the region of interest ROI obtained through the first neural network model NN1 as input data. As another example, the boundary point extraction module 110 may obtain the boundary point BP by using the boundary between the hair and the forehead and the region of interest ROI including at least a portion of the hair and the forehead around the boundary between the hair and the forehead as input data through the second neural network model NN2.

Meanwhile, the neural network model may be at least one of a convolutional neural network (CNN), a recursive neural network (RNN), a deep bellief network (DBN), a long short-term memory (LSTM), a gated recurrent neural network (GRU), and a variant and combination thereof.

Figure 11:
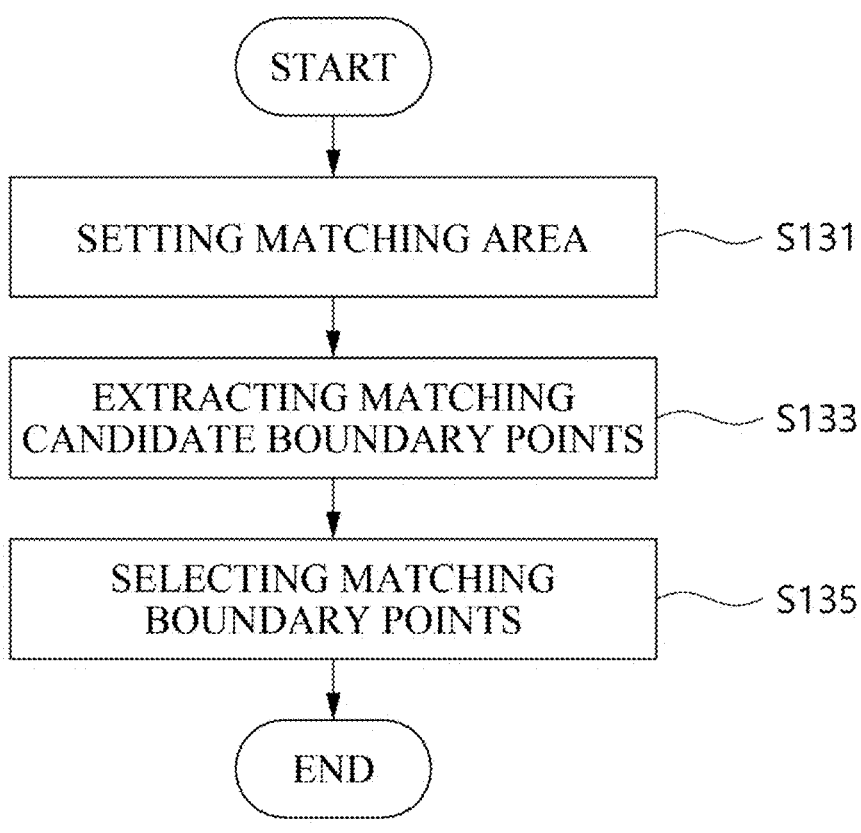
FIG. 11 is a diagram for describing a method of selecting a matching boundary point from a head image.

FIG. 11 is a diagram for describing a method of selecting a matching boundary point from a head image. Hereinafter, a method of selecting a matching boundary point MBP from among a plurality of boundary points BP based on a plurality of feature points FP extracted from a head image will be described with reference to FIG. 11.

Referring to FIG. 11, the matching boundary point selection module 130 may select a matching boundary point MBP through a setting matching area S131, a extracting matching candidate boundary points S133, and a selecting matching boundary points S135. Hereinafter, each step performed by the matching boundary point selection module 130 will be described in more detail with reference to the drawings.

The matching boundary point MBP may mean at least one of a plurality of boundary points BP extracted from the boundary point extraction module 110. For example, the matching boundary point MBP may refer to a boundary point corresponding to a feature point FP among a plurality of boundary points BP extracted from the boundary point extraction module 110. Alternatively, the matching boundary point MBP may mean a boundary point corresponding to the feature point of the first group G1FP among the plurality of boundary points BP.

Figure 12:
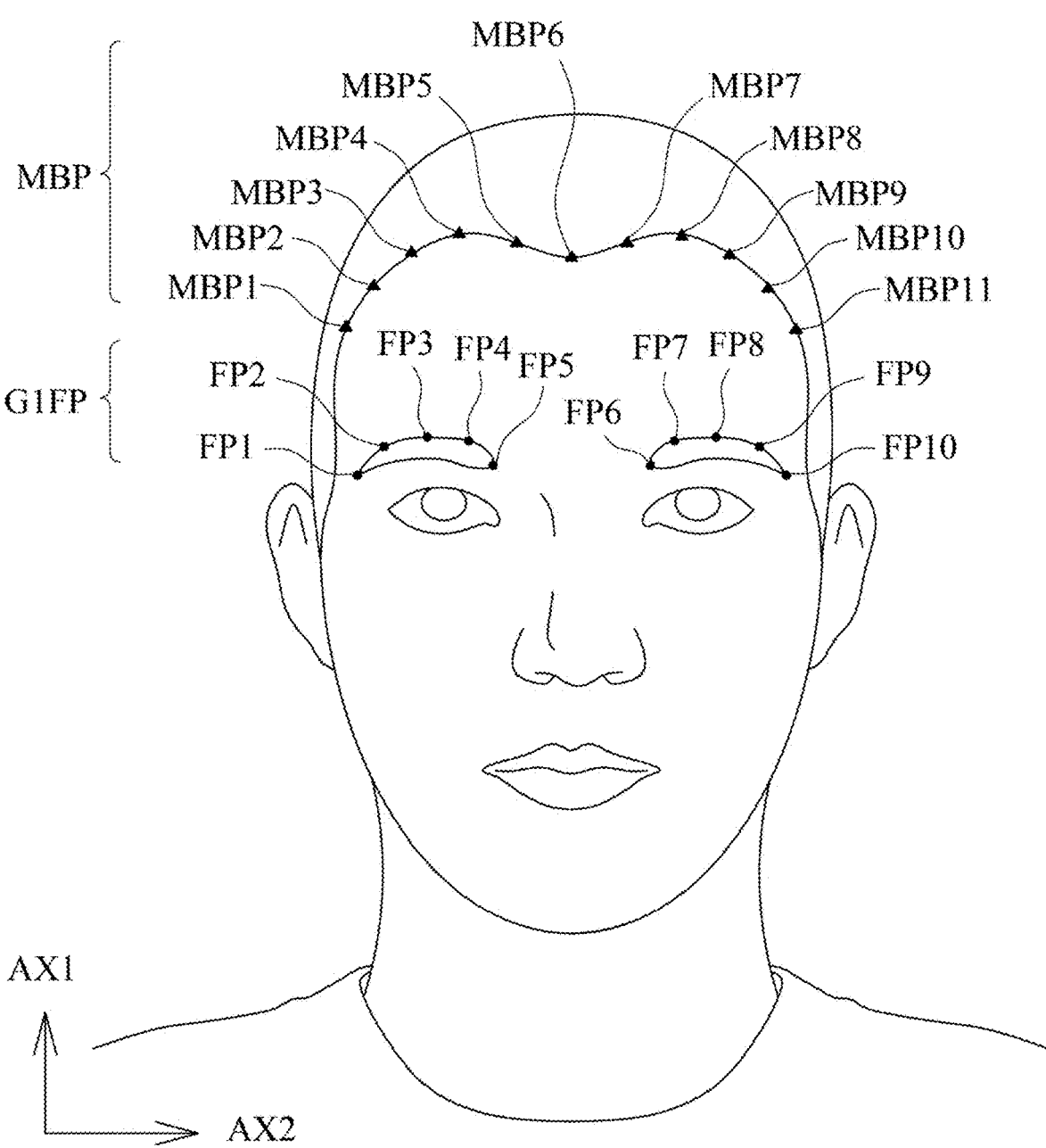
FIG. 12 is a diagram illustrating a feature point of a first group and a matching boundary point corresponding thereto according to an embodiment.

FIG. 12 is a diagram illustrating a feature point of a first group and a matching boundary point corresponding thereto, according to an embodiment. The feature point of the first group G1FP and the matching boundary point MBP shown in FIG. 12 are according to an embodiment, and the number and location of the feature point of the first group G1FP and the matching boundary point MBP may be different from those shown in FIG. 12.

For example, in FIG. 12, the first feature point FP1 to the tenth feature point FP10 are feature points of the first group G1FP, and the first matching boundary point MBP1 to the eleventh matching boundary point MBP11 are matching boundary points MBP. In this case, the matching boundary point MBP may be selected as a boundary point corresponding to at least one feature point among the plurality of feature points FP. Alternatively, the matching boundary point MBP may be selected as a boundary point corresponding to one or more of the feature points of the first group G1FP.

According to an embodiment, the matching boundary point MBP may be selected as a boundary point corresponding to any one feature point among the feature points of the first group G1FP. For example, referring to FIG. 12, the matching boundary point MBP may be selected based on one feature point among the first feature point FP1 to the tenth feature point FP10 corresponding to the feature point of the first group G1FP. For example, the first matching boundary point MBP1 may be a boundary point corresponding to the first feature point FP1 among the plurality of boundary points BP, and the second matching boundary point MBP2 may be a boundary point corresponding to the second feature point FP2 among the plurality of boundary points BP.

According to another embodiment, the matching boundary point MBP may be selected as a boundary point corresponding to two or more of the feature points of the first group G1FP. More specifically, the matching boundary point MBP may be selected as a matching boundary point having a boundary point corresponding to two neighboring points among the feature points of the first group G1FPs. For example, referring to FIG. 12, the matching boundary point MBP may be selected based on a plurality of feature points from among the first feature point FP1 to the tenth feature point FP10 corresponding to the feature point of the first group G1FP. For example, the sixth matching boundary point MBP6 may be selected based on the fifth feature point FP5 and the sixth feature point FP6. More specifically, the sixth matching boundary point MBP6 may be a boundary point corresponding to an x-coordinate of a mid-point between the fifth feature point FP5 and the sixth feature point FP6.

The matching boundary point MBP may be a boundary point corresponding to a characteristic portion of the face among the plurality of boundary points BP. In this case, the characteristic portion of the face may mean a portion corresponding to a characteristic point among the boundaries between the hair and the forehead. For example, a characteristic portion of the face may mean a portion corresponding to a middle portion of the forehead or a portion corresponding to a specific portion of the eyebrow of the boundary between the hair and the forehead. Referring to FIG. 12, the matching boundary point corresponding to the center portion of the forehead may be the sixth matching boundary point MBP6, and the matching boundary point corresponding to a specific portion of the eyebrow among the boundaries of the forehead may be the fourth matching boundary point MBP4 or the seventh matching boundary point MBP7.

According to an embodiment, the user hair loss state determination module 160 of FIG. 6 may determine the user's hair loss state based on the matching boundary point obtained by the matching boundary point selection module 130. More specifically, the matching boundary point selection module 130 may select a matching boundary point MBP corresponding to one or more feature points satisfying a predetermined criterion among the plurality of feature points FP, and the user hair loss state determination module 160 may determine the user's hair loss state based on the selected matching boundary point MBP.

For example, referring to FIG. 12, the matching boundary point selection module 130 may select a matching boundary point MBP (e.g., a fourth matching boundary point MBP4, a sixth matching boundary point MBP6, or an eighth matching boundary point MBP8) corresponding to one or more feature points (e.g., a third feature point FP3, a fifth feature point FP5, a sixth feature point FP6, or an eighth feature point FP8) satisfying a predetermined criterion among the feature points of the first group G1FP, and the user hair loss state determination module 160 may determine the hair loss state of the user based on the selected matching boundary point.

According to another embodiment, the user hair loss state determination module 160 may determine the user's hair loss state based on one or more boundary points satisfying a predetermined criterion among the matching boundary points obtained by the matching boundary point selection module 130. More specifically, the matching boundary point selection module 130 may select matching boundary points MBP corresponding to the feature point FP, and the user hair loss state determination module 160 may determine the user's hair loss state based on one or more matching boundary points MBP satisfying a predetermined criterion among the selected matching boundary points MBP.

For example, referring to FIG. 12, the matching boundary point selection module 130 may select a plurality of matching boundary points corresponding to the feature point of the first group G1FP, for example, the first matching boundary point MBP1 to the eleventh matching boundary point MBP11, and the user hair loss state determination module 160 may determine the user's hair loss state based on a matching boundary point MBP satisfying a predetermined criterion among the selected matching boundary points MBP, for example, a fourth matching boundary point MBP4, a sixth matching boundary point MBP6, or an eighth matching boundary point MBP8.

Referring to FIG. 11, in the setting matching area S131, the matching boundary point selection module 130 may set a matching area. As described below, the matching region may be used as a reference region for selecting the matching boundary point MBP among the plurality of boundary points BP.

Figure 13:
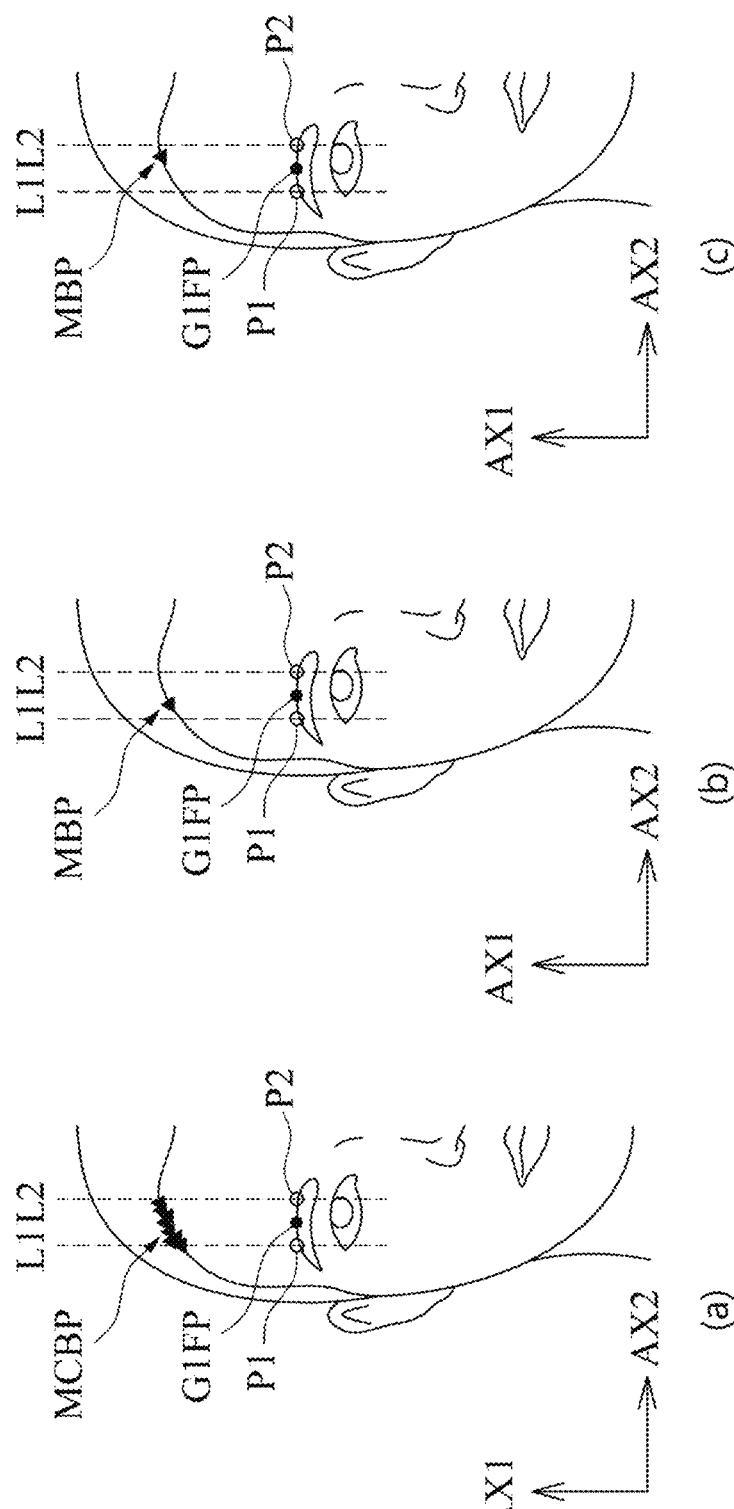
FIG. 13 is a diagram for describing a method of selecting a matching boundary point according to an embodiment.

The matching region may be set based on a single feature point or a plurality of feature points. FIG. 13 is a diagram for describing a method of selecting a matching boundary point according to an embodiment. Referring to FIG. 13, the matching region may be set based on a single feature point.

According to an embodiment, the matching region may be set as a region between a first straight line L1 and a second straight line L2 extending in a first direction AX1 on the head image from two points P1 and P2 determined based on one feature point of the first group G1FP. In this case, the first point P1 may be a point from the feature point of the first group G1FP to be spaced apart by a first distance in a second direction AX2 on the head image, and the second point P2 may be a point from the feature point of the first group G1FP to be spaced apart by a second distance in the second direction AX2.

According to an embodiment, the first point P1 may be a point from the feature point of the first group G1FP to be spaced apart by a first distance in a first direction AX2 of the second axis AX2, and the second point P2 may be a point from the feature point of the first group G1FP to be spaced apart by a second distance in a second direction AX2. In this case, the first direction may be a negative direction of the corresponding axis, and the second direction may be a positive direction of the corresponding axis. In addition, the first distance and the second distance may be the same or different from each other.

According to another embodiment, the first point P1 and the second point P2 may be a point from the feature point of the first group G1FP to be spaced apart by a first distance and a second distance in the same direction AX2 of the second axis AX2. In this case, the first distance and the second distance are set to different values.

The second axis AX2 may be set as an axis perpendicular to the first axis AX1. According to an embodiment, the first axis AX1 may refer to the y-axis of the head image, and the second axis AX2 may refer to the x-axis of the head image, but the present invention is not limited thereto. For example, when it is determined that the user's head is inclined by an angle a with respect to the y-axis of the image in the acquired head image, the first axis AX1 and the second axis AX2 may be set as an axis inclined by a with respect to the y-axis and the x-axis of the head image, respectively.

FIG. 14 is a diagram for describing a method of selecting a matching boundary point according to another embodiment. Referring to FIG. 14, the matching region may be set based on a plurality of feature points.

According to an embodiment, the matching region may be set as a region between a first straight line L1 and a second straight line L2 extending in a first direction AX1 on the head image from a plurality of first group feature points G1FP. Specifically, the matching region may be set as a region between a first straight line L1 and a second straight line L2 extending in a first direction AX1 on the head image from each of the first feature points G1FP and the second feature point constituting the feature point of the first group G1FP. In this case, the plurality of first group feature points G1FP may mean two feature points FP neighboring each other among the first group feature points G1FP.

Meanwhile, the definitions of the first axis AX1 and the second axis AX2 shown in FIG. 14 are the same as the definitions of the first axis AX2 and the second axis AX2 described above with reference to FIG. 13.

Referring back to FIG. 11, in the extracting matching candidate boundary points S133, the matching boundary point selection module 130 may extract the matching candidate boundary point. More specifically, the matching boundary point selection module 130 may extract at least one of boundary points located within the matching area among the plurality of boundary points BP as a matching candidate boundary point MCBP.

Here, the matching candidate boundary point MCBP may refer to at least one boundary point located within the matching area among the plurality of boundary points BP. According to an embodiment, the matching candidate boundary point MCBP may mean at least one boundary point satisfying a predetermined criterion among a plurality of boundary points BP located in the matching area. For example, the matching candidate boundary point MCBP may mean a boundary point having a probability value corresponding to a boundary line between a hair and a forehead among a plurality of boundary points BP located in a matching area that is equal to or greater than a predetermined threshold value.

Referring to FIG. 13(a), the matching candidate boundary point MCBP may be a boundary point corresponding to a single feature point of the first group G1FP. According to an embodiment, the matching candidate boundary point MCBP may be a boundary point located in a region between the first straight line L1 and the second straight line L2 extending in the first axis AX1 direction on the head image from two points P1 and P2 determined based on a feature point of the first group G1FP. Here, the first point P1 and the second point P2 are the same as those described above in the setting matching area S131. According to another embodiment, the matching candidate boundary point MCBP may be a boundary point having a probability value corresponding to a boundary line between the hair and the forehead among boundary points located in regions between the first straight line L1 and the second straight line L2 extending from two points P1 and P2 determined based on one feature point of the first group G1FP toward the first axis AX1 on the head image, respectively, that is equal to or greater than a predetermined threshold value.

Referring to FIG. 14(a), the matching candidate boundary point MCBP may be a boundary point corresponding to a plurality of first group feature points G1FP. According to an embodiment, the matching candidate boundary point MCBP may be a boundary point located in a region between the first straight line L1 and the second straight line L2 extending from the plurality of first group feature points G1FP toward the first axis AX1 on the head image, respectively. In this case, the plurality of first group feature points G1FP may mean two neighboring feature points FP among the first group feature points G1FP. According to another embodiment, the matching candidate boundary point MCBP may be a boundary point having a probability value corresponding to a boundary line of hair and forehead among boundary points located in a region between the first straight line L1 and the second straight line L2 extending from the plurality of first group feature points G1FP toward the first axis AX1 on the head image, respectively, that is equal to or greater than a predetermined threshold value.

Referring back to FIG. 11, in the selecting matching boundary points S135, the matching boundary point selection module 130 may select a specific matching boundary point MBP from among the matching candidate boundary points. More specifically, the matching boundary point selection module 130 may select a matching boundary point MBP corresponding to the feature point of the first group G1FP. Alternatively, the matching boundary point selection module 130 may select at least one matching boundary point MBP satisfying a predetermined criterion from among the matching candidate boundary points MCBP included in the matching area.

The matching boundary point selection module 130 may select a boundary point having a representative value satisfying a predetermined criterion from among the matching candidate boundary points MCBP as the matching boundary point MBP. In this case, the representative value may include a probability value corresponding to the boundary point corresponding to a boundary line between the hair and the forehead, a first axis AX1 and/or a second axis AX2 coordinate value on the head image of the corresponding boundary point, and the like.

According to an embodiment, the matching boundary point selection module 130 may select a boundary point having a highest probability value corresponding to a boundary line between the hair and the forehead from among the matching candidate boundary points MCBP in the matching area as the matching boundary point MBP. Referring to FIGS. 13B and 14B, the matching boundary point selection module 130 may select a boundary point having a highest probability value corresponding to a boundary line between the hair and the forehead from among the matching candidate boundary points MCBP shown in each drawing as the matching boundary point MBP.

According to another embodiment, the matching boundary point selection module 130 may select a boundary point having a highest first axis AX1 coordinate value on the head image from among the matching candidate boundary points MCBP in the matching area as the matching boundary point MBP. Referring to FIGS. 13C and 14C, the matching boundary point selection module 130 may select a boundary point having a highest first axis AX1 coordinate value on the head image from among the matching candidate boundary points MCBP shown in FIGS. 13A and 14A as the matching boundary point MBP.

According to still another embodiment, the matching boundary point selection module 130 may select a boundary point having a highest first axis AX1 coordinate value on the head image from among the matching candidate boundary points MCBP having a probability value corresponding to a boundary line between the hair and the forehead equal to or greater than a predetermined criterion in the matching area as the matching boundary point MBP. Referring to FIGS. 13C and 14C, the matching boundary point selection module 130 may select a boundary point having a highest first axis AX1 coordinate value on the head image from among the matching candidate boundary points MCBP having a probability value corresponding to a boundary line between the hair and the forehead equal to or greater than a predetermined criterion shown in each drawing as the matching boundary point MBP.

According to still another embodiment, although not shown in the drawings, the matching boundary point selection module 130 may select a boundary point corresponding to a second axis AX2 coordinate value of a feature point FP serving as a reference of the matching area selection from among the matching candidate boundary points MCBP in the matching area as the matching boundary point MBP. Alternatively, the matching boundary point selection module 130 may select a boundary point corresponding to a second axis AX2 coordinate value of a feature point FP serving as a reference of the matching area selection from among the matching candidate boundary points MCBP having a probability value corresponding to a boundary line between the hair and the forehead equal to or greater than a predetermined criterion as the matching boundary point MBP.

More specifically, the matching boundary point selection module (130) may select, as the matching boundary point MBP, a boundary point having a second axis AX2 coordinate value closest to the coordinate value of the second axis AX2 of a single feature point of the first group G1FP, which is a reference for the matching region selection, among the matching candidate boundary points MCBP in the matching region.

Alternatively, the matching boundary point selection module 130 may select, as the matching boundary point MBP, a boundary point having a second axis AX2 coordinate value closest to a median value of a second axis AX2 coordinate value of two neighboring feature points FP, which are a reference of the matching region selection, among the matching candidate boundary points MCBP in the matching region.

As described above, the user terminal may select the matching boundary point MBP according to various criteria and determine the hair loss state of the user based on the selected matching boundary point MBP. In the above-described embodiments, when the boundary point having the highest first axis AX1 coordinate value on the head image is selected as the matching boundary point MBP, the matching boundary point MBP corresponding to a portion where the degree of hair loss progresses is more severe on the head image may be selected, and thus an effect of more conservatively determining the hair loss state of the user may be provided.

The matching boundary point MBP may be selected based on the feature point FP as described above, and the controller 100 may determine the hair loss state of the user using at least one of the selected matching boundary points MBP.

Meanwhile, in some cases, there may be a case where the matching boundary point MBP necessary to determine the hair loss state of the user is omitted or insufficient. In this case, the coordinates of the omitted matching boundary point may be determined based on at least one of the pre-selected matching boundary points MBP. Hereinafter, a method of defining the omitted matching boundary point based on at least one of the pre-selected matching boundary points MBP will be described.

According to an additional embodiment, at least a portion of the matching boundary point MBP may be defined based on the pre-selected matching boundary point MBP. For example, when there is a missing matching boundary point in the right region of the forehead based on the center of the head image, the missing matching boundary point may be defined based on the matching boundary point MBP corresponding to the left region of the forehead among the pre-selected matching boundary points MBP.

Referring to FIG. 12, assuming that the eighth matching boundary point MBP8 is omitted in the right region of the forehead based on the center of the head image, the missing eighth matching boundary point MBP8 may be defined based on the fourth matching boundary point MBP4 corresponding to the left region of the forehead among the pre-selected matching boundary points MBP. In other words, the eighth matching boundary point MBP8 may be defined by the coordinates of the fourth matching boundary point MBP4. More specifically, the first axis AX1 coordinate of the eighth matching boundary point MBP8 may be defined as the first axis AX1 coordinate of the fourth matching boundary point MBP4. Also, the second axis AX2 coordinate of the eighth matching boundary point MBP8 may correspond to the second axis AX2 coordinate of the seventh feature point FP7. In this case, the seventh feature point FP7 may be a feature point corresponding to the fourth feature point FP4 which is a basis for the selection of the fourth matching boundary point MBP4.

Meanwhile, although the case where the missing matching boundary point corresponds to the right region of the forehead based on the center of the head image has been described above, even when there is a missing matching boundary point in the left region of the forehead, the aforementioned method can be applied in the same manner. Based on the previously selected matching boundary point MBP corresponding to the right region of the forehead, the missing matching boundary point can be defined.

As another example, when the center matching boundary point corresponding to the center of the second axis AX2 of the head image is missing, the missing center matching boundary point may be defined by a matching boundary point MBP corresponding to one region of the left or right eyebrows among the pre-selected matching boundary points MBP. Referring to FIG. 12, assuming that the sixth matching boundary point MBP6 corresponding to the center of the second axis AX2 of the head image among the boundary points of the hair and the forehead is missing, the first axis AX1 coordinate of the sixth matching boundary point MBP6 may be determined as the first axis AX1 coordinate of the fourth matching boundary point MBP4 corresponding to one region of the left eyebrow among the pre-selected matching boundary points. In this case, the matching boundary point MBP corresponding to one region of the left or right eyebrows may be the same as or correspond to the matching boundary point MBP described above with reference to FIG. 13.

Meanwhile, the second axis AX2 coordinate of the missing sixth matching boundary point MBP6 may be determined based on the second axis AX2 coordinate of the first feature point corresponding to one region of the left eyebrow and the second feature point corresponding to one region of the right eyebrow. For example, the second axis AX2 coordinate of the missing sixth matching boundary point MBP6 may be determined as the intermediate coordinate of the second axis AX2 coordinate of the first feature point and the second axis AX2 coordinate of the second feature point. In this case, one region of the left eyebrow and one region of the right eyebrow may be symmetrical with respect to the first axis AX1 on the head image.

As still another example, the first axis AX1 coordinate of the matching boundary point MBP may be determined by the first axis AX1 coordinate of another matching boundary point MBP that mutually symmetrical within an error range with respect to the first axis AX1 at the center of the head image. More specifically, assuming that the first matching boundary point and the second matching boundary point are mutually symmetrical within the error range with respect to the first axis AX1 at the center of the head image, when the first axis AX1 coordinate of the first matching boundary point is greater than the first axis AX1 coordinate of the second matching boundary point, the first axis AX1 coordinate of the second matching boundary point may be determined as the first axis AX1 coordinate of the first matching boundary point. Referring to FIG. 12, the fourth matching boundary point MBP4 and the eighth matching boundary point MBP8 are mutually symmetrical within the error range with respect to the first axis AX1 on the head image. In this case, when the first axis AX1 coordinate of the fourth matching boundary point MBP4 is greater than the first axis AX1 coordinate of the eighth matching boundary point MBP8, the first axis AX1 coordinate of the eighth matching boundary point MBP8 may be determined as the first axis AX1 coordinate of the fourth matching boundary point MBP4.

Hereinbefore, various embodiments of extracting a boundary point, a feature point, and a matching boundary point from a head image of a user were described. According to an embodiment of the present application, the user terminal may provide the user's hair loss state information based on the extracted boundary point, the feature point, and/or the matching boundary point.

Figure 15:
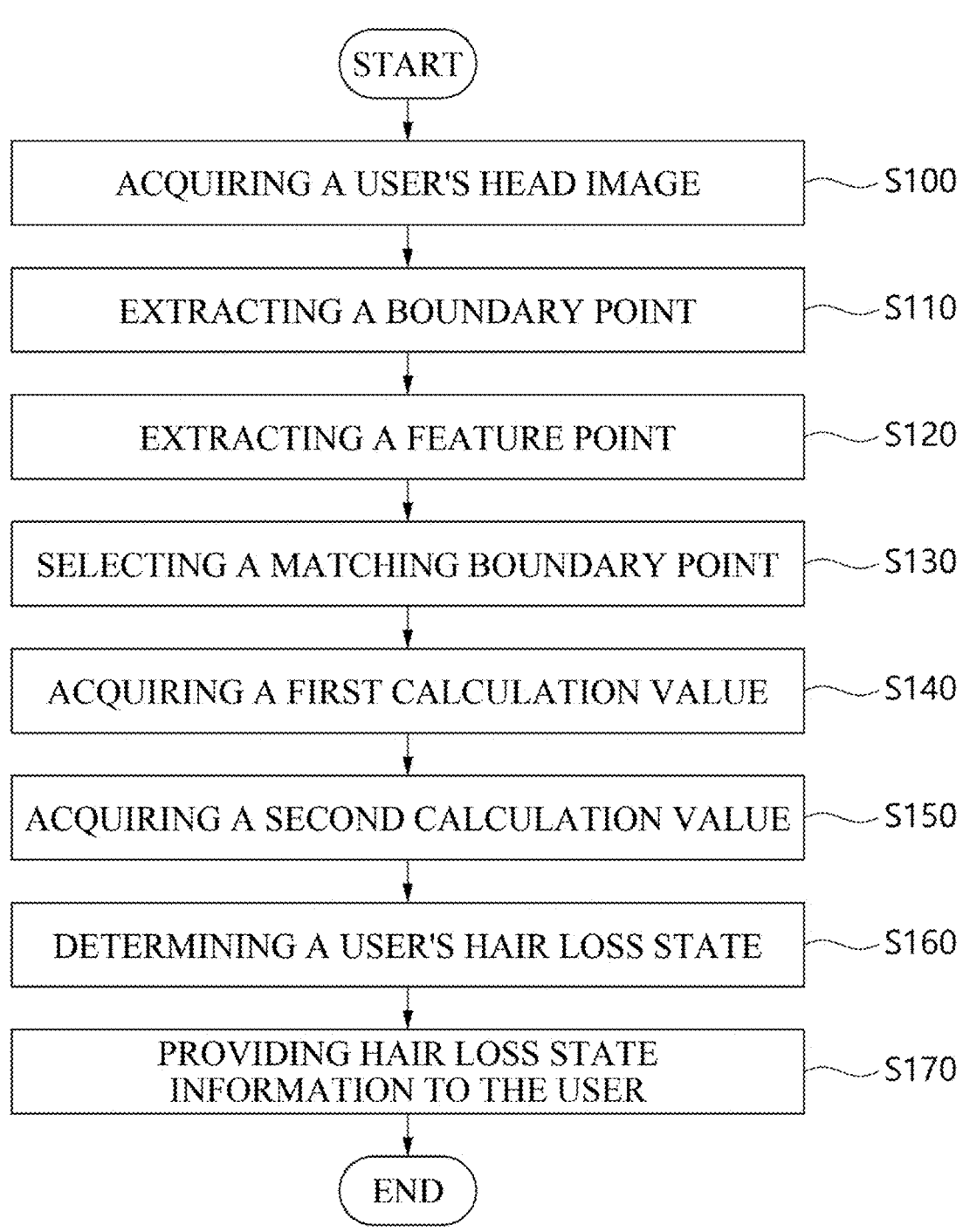
FIG. 15 is a diagram for describing a process for providing hair loss state information according to an embodiment.

FIG. 15 is a diagram for describing a process of providing hair loss state information according to an embodiment.

Referring to FIG. 15, the process for providing hair loss state information according to an embodiment may include acquiring a user's head image (S100), extracting a boundary point and a feature point from the acquired head image (S110), S120, selecting a matching boundary point of the head image (S130), acquiring a first calculation value and a second calculation value of the head image (S140, S150), determining a user's hair loss state based on the first calculation value and the second calculation value (S160), and providing hair loss state information to the user based on a result of the user's hair loss state determination (S170). Meanwhile, the flowchart of FIG. 15 is exemplary, and some orders of each step shown in FIG. 15 may be changed.

Referring to FIG. 15, the controller 100 of FIG. 2 may extract a boundary point BP from a head image through the boundary point extraction step S110. Specifically, the controller 100 may acquire a user's head image from the image capture unit 200 and extract a boundary point BP based on the acquired image. In addition, the controller 100 may extract the feature point FP from the head image through the feature point extraction step S120. Specifically, the controller 100 may acquire a user's head image from the image capture unit 200 and extract a feature point FP based on the acquired image.

In addition, the controller 100 may select the matching boundary point MBP based on the boundary point BP and the feature point FP of the head image through the matching boundary point selection step S130. Specifically, the controller 100 may select one or more matching boundary points MBP corresponding to the feature point FP from among the plurality of boundary points BP. The method of extracting a plurality of boundary points BP and a plurality of feature points FP from the head image and the method of selecting the matching boundary points MBP have been described above, and thus detailed descriptions thereof will be omitted.

According to an embodiment, the controller 100 of FIG. 2 may calculate calculated values according to a preset reference from the head image and may diagnose the hair loss state of the user based on the calculated values. In step S140 of obtaining the first calculated value of FIG. 15, the controller 100 may obtain a first calculated value of the head image. According to an embodiment, the first calculated value acquisition may be performed by the first calculation value acquisition module 140 of the controller 100. The first calculation value obtaining module 140 may obtain the first calculation value based on the feature point FP and the matching boundary point MBP. Here, the first calculation value may mean a calculation value related to the above-described upper face portion.

For example, the first calculated value may be determined based on a distance between the feature point FP and the matching boundary point MBP. For example, the first calculation value may be determined based on a distance between the feature point FP and the matching boundary point MBP determined based on the first axis AX1 or a distance between the feature point FP and the matching boundary point MBP determined based on the second axis AX2. In other words, the first calculated value may mean a distance value between a first axis AX1 coordinate of the feature point FP and a first axis AX1 coordinate of the matching boundary point MBP corresponding to the feature point.

As another example, the first calculated value may be determined based on an area calculated by at least one feature point FP and at least one matching boundary point MBP. For example, the first calculation value may mean an area value calculated by a plurality of feature points FP and a plurality of matching boundary points MBP respectively corresponding to the plurality of feature points FP.

Figure 16:
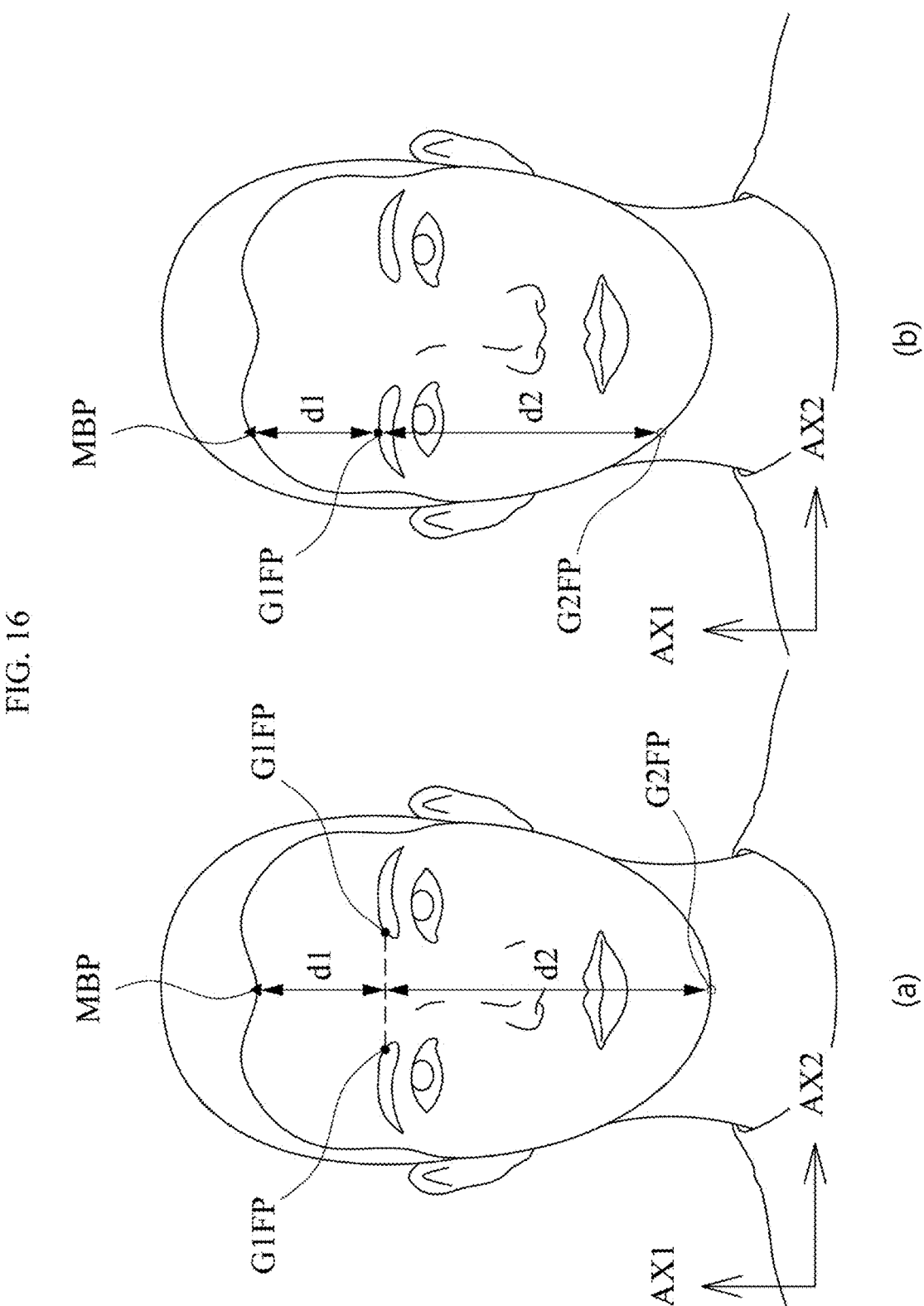
FIG. 16 is a diagram for exemplarily describing a method of obtaining a first calculation value and a second calculation value based on a head image.

FIG. 16 is a diagram for exemplarily describing a method of obtaining a first calculated value and a second calculated value based on a head image. Hereinafter, a method of obtaining a first calculation value will be described in detail with reference to FIG. 16.

Referring to FIG. 16, the first calculation value may include an upper face portion calculation value determined based on a distance between a feature point of the first group G1FP and a matching boundary point MBP corresponding to the feature point of the first group G1FP based on a first axis AX1 on the head image. In this case, the upper face portion calculation value may include a length of the upper face portion d1, or may include an area value of the upper face portion. In other words, the first calculation value may mean a length of the upper face portion d1 determined based on a preset area of the face. In this case, FIG. 16(a) is a diagram exemplarily illustrating a length of the upper face portion d1 obtained based on a center area of the face.

Referring to FIG. 16(a), the first calculation value may mean a length of the upper face portion d1 obtained based on the center area of the face. Here, the length of the upper face portion d1 obtained based on the center area of the face may mean a length in a direction of the first axis AX1 at the center of the upper face portion. In this case, the length of the upper face portion d1 may be determined based on a center portion of the face based on a second axis AX2 on the head image. According to an embodiment, the first calculation value may be calculated based on a single feature point of first group G1FP and a single matching boundary point MBP selected based on the feature point of first group G1FP. According to another embodiment, the first calculation value may be calculated based on a plurality feature point of first group G1FP and a single matching boundary point MBP selected based on the plurality feature point of first group G1FP.

For example, the single matching boundary point MBP may be selected based on a first feature point corresponding to one area of the left eyebrow and a second feature point corresponding to one area of the right eyebrow. In this case, the one area of the left eyebrow and the one area of the right eyebrow may be symmetrical based on the first axis AX1 on the head image. As a more specific example, the matching boundary point MBP may be selected to correspond to a midpoint of a feature point located at the rightmost side of the left eyebrow and a feature point located at the leftmost side of the right eyebrow among the feature point of the first group G1FP. In this case, the first calculation value d1 may be determined based on a difference between a coordinate value of the midpoint and a coordinate value of the matching boundary point MBP based on the first axis AX1 on the head image. That is, the first calculation value d1 may be determined based on a difference between a coordinate value of the first axis AX1 of the midpoint and a coordinate value of the first axis AX1 of the matching boundary point MBP.

According to another embodiment, the first calculation value d1 may be calculated based on a plurality of matching boundary points MBP selected based on each of a plurality feature point of first group G1FP and a plurality feature point of first group G1FP.

FIG. 16(b) is a diagram exemplarily illustrating a length of the upper face portion d1 obtained based on an area above the eyebrow. Referring to FIG. 16(b), the first calculation value d1 may mean a length of the upper face portion d1 obtained relative to a region above the eyebrows. In this case, the first calculation value may be calculated by the feature point G1FP of at least one first group and the at least one matching boundary point MBP selected based on the at least one first group, and since the same as or corresponds to the description of FIG. 16(a), a redundant description thereof will be omitted.

For example, the first calculation value d1 may be calculated based on the feature point of the first group G1FP located in a region of the left or right eyebrows and the matching boundary point MBP selected corresponding thereto. In a more specific example, the first calculation value d1 may be determined by a difference between a coordinate value of the feature point of the first group G1FP and a coordinate value of the matching boundary point MBP on the first axis AX1 of the head image. That is, the first calculation value d1 may be determined by a difference between a coordinate value of the first axis AX1 of the feature point of the first group G1FP and a coordinate value of the first axis AX1 of the matching boundary point MBP.

Meanwhile, various embodiments of the case where the first calculation value d1 indicates a length are described with reference to FIGS. 16(a) and 16(b), but the present disclosure is not limited thereto, and the first calculation value d1 may be a value related to an area or a width calculated by the at least one feature point FP and the at least one matching boundary point MBP. For example, although not shown in the drawings, the first calculation value may be an area value calculated by the at least one feature point FP and the at least one matching boundary point MBP. Specifically, the first calculation value may mean an area value of the upper face portion calculated using a coordinate of the at least one feature point FP and a coordinate of the at least one matching boundary point MBP. As another example, although not shown in the drawings, the first calculation value may be a width value calculated by the at least one feature point FP and the at least one matching boundary point MBP. Specifically, the first calculation value may mean a width determined by a coordinate of a second axis AX2 of the at least one feature point FP and a coordinate of the second axis AX2 of the at least one matching boundary point MBP, for example, a distance value in a direction of the second axis AX2 of the head image.

In step S150 of obtaining the second calculation value of FIG. 15, the controller 100 may obtain a second calculation value for the head image. According to an embodiment, the second calculation value obtaining may be performed by the second calculation value obtaining module 150 of the controller 100. The second calculation value obtaining module 140 may obtain the second calculation value based on the feature point FP. Here, the second calculation value may mean a calculation value related to the above-described middle eye surface part.

For example, the second calculation value may be determined based on a distance between the plurality of feature points FP. Alternatively, the second calculation value may be determined based on a distance between the feature point of the first group G1FP and the feature point of the second group G2FP. For example, the second calculation value may be determined based on a distance between the feature point of the first group G1FP and the feature point of the second group G2FP determined based on the first axis AX1 or a distance between the feature point of the first group G1FP and the feature point of the second group G2FP determined based on the second axis AX2. In a more specific example, the second calculation value As another example, the second calculation value may be determined based on an area calculated by at least a plurality of feature points FP. For example, the second calculation value may mean an area value calculated by a feature point G1FP of a plurality of first groups and a feature point G2FP of a plurality of second groups corresponding to each of the feature points G1FP of the plurality of first groups.

Hereinafter, a method of obtaining a second calculated value will be described in detail with reference to FIG. 16. Referring to FIG. 16, the second calculation value may include a middle-lower face portion calculation value determined based on a distance between a feature point of a first group G1FP and a feature point of a second group G2FP corresponding to the a feature point of a first group G1FP based on a first axis AX1 on the head image. In this case, the calculated value of the middle-lower face portion may include a length of the middle-lower face portion d2, or may include an area value of the middle-lower face portion.

Referring to FIG. 16(a), the second calculation value may mean a length of the middle-lower face portion d2 calculated based on the center region of the face. Here, the length of the middle-lower face portion d2 calculated based on the center region of the face may mean a length in the first axial direction at the center of the middle-lower face portion. In this case, the length of the middle-lower face portion d2 may be determined based on a center portion of the face based on the second axis AX2 on the head image.

According to an embodiment, the second calculation value may be calculated based on a single feature point of first group G1FP and a single feature point of second group G2FP selected based on the single first group of feature points. Alternatively, the second calculation value may be calculated based on a single feature point of second group G2FP and a single feature point of first group G1FP selected based on the feature point of second group G2FP.

According to another embodiment, the second calculation value may be calculated based on a plurality of first groups of feature points G1FP and a single second group of feature points G2FP selected based on the first group of feature points. Alternatively, the second calculation value may be calculated based on the plurality of second groups of feature points G2FP and the single first groups of feature points G1FP selected based on the plurality of second groups of feature points.

For example, the feature point of the second group G2FP may be selected based on the feature point of the first group G1FP corresponding to the area of the left eyebrow and the feature point of the first group G1FP corresponding to the area of the right eyebrow. In this case, one region of the left eyebrow and one region of the right eyebrow may be symmetrical with respect to the first axis AX1 on the head image. As a more specific example, the feature point of the second group G2FP may be selected to correspond to a feature point located at the rightmost side of the left eyebrow and a feature point located at the leftmost side of the right eyebrow among the feature points of the first group G1FP. In this case, the second calculated value d2 may be determined by a difference between a coordinate value of the intermediate point and a coordinate value of the feature point of the second group G2FP based on the first axis AX1 on the head image. That is, the second calculated value d2 may be determined by a difference between the first axis AX1 coordinate value of the intermediate point and the first axis AX1 coordinate value of the feature point of the second group G2FP.

According to another embodiment, the second calculation value d2 may be calculated based on a plurality of feature points of the first group G1FP and a plurality of feature points of the second group G2FP selected based on each of the plurality of feature points of the first group G1FP.

FIG. 16(b) is a diagram illustrating a length of the upper face portion d2 obtained based on a region below the eyebrow. Referring to FIG. 16(b), the second calculation value d2 may mean a length of the middle face portion d2 obtained based on the region below the eyebrow. In this case, the second calculation value may be calculated by at least one feature point of the first group G1FP and at least one feature point of the second group G2FP selected based on the at least one feature point of the first group G1FP, and since the second calculation value is the same as or corresponds to the description of FIG. 16(a), redundant descriptions will be omitted.

For example, the second calculation value d2 may be calculated based on the feature point of the first group G1FP located in a region of the left or right eyebrows and the feature point of the second group G2FP selected corresponding to the first group. In a more specific example, the second calculation value d2 may be determined by a difference between a coordinate value of the feature point of the first group G1FP and a coordinate value of the feature point of the second group G2FP based on a first axis AX1 on the head image. That is, the second calculation value d2 may be determined by a difference between a coordinate value of a first axis AX1 of the feature point of the first group G1FP and a coordinate value of a first axis AX1 of the feature point of the second group G2FP.

Meanwhile, various embodiments of the case where the second calculation value d2 represents a length are described with reference to FIGS. 16(a) and 16(b), but the present disclosure is not limited thereto, and the second calculation value d2 may be a value related to an area or a width calculated by at least one feature point FP, for example, the feature point of the first group G1FP and the feature point of the second group G2FP.

For example, although not shown in the drawings, the second calculation value may be an area value calculated by a plurality of feature points FP. Specifically, the second calculation value may mean an area value of the middle-lower face portion calculated using coordinates of the feature point of the first group G1FP and the feature point of the second group G2FP.

As another example, although not shown in the drawings, the second calculation value may be a width value calculated by a plurality of feature points FP, for example, the feature point of the first group G1FP and the feature point of the second group G2FP. Specifically, the second calculation value may mean a width determined by coordinates of a second axis AX2 of the feature point of the first group G1FP and coordinates of a second axis AX2 of the feature point of the second group G2FP, for example, a distance value in a direction of the second axis AX2 on the head image.

Meanwhile, the first calculation value and the second calculation value may be calculated by considering an angle at which a user's head is inclined in the head image. Specifically, when the user's head is inclined in the head image as shown in FIG. 5(b), the reference axis of the image or the image itself may be corrected and then the first calculation value or the second calculation value may be calculated. For example, when the user's head is inclined by an angle a based on a y-axis in the head image, the first calculation value and the second calculation value may be calculated by defining the first axis AX1 and the second axis AX2 on the head image as an axis inclined by a based on the y-axis and the x-axis of the image, respectively. Another example is that, based on the degree of inclination of the head image, the head image itself can be adjusted. After adjusting, the first calculation value and the second calculation value can be determined based on the corrected head image.

Meanwhile, as described above, the first calculation value and the second calculation value may be obtained based on a preset area of the face. In this case, with regard to the preset area of the face, the preset area of the face is illustrated as a center area of the face and a brow above/below the brow of the face in FIGS. 16(a) and 16(b), but the present invention is not limited thereto. Although not shown in the drawings, a preset area of the face may mean various areas related to a major portion of the face.

In addition, in FIG. 16(a), the first calculated value d1 and the second calculated value d2 are illustrated as being obtained based on the center region of the face, and in FIG. 16(b), the first calculated value d1 and the second calculated value d2 are illustrated as being obtained based on the upper/lower region of the eyebrows of the face, but the present invention is not limited thereto. For example, the first calculated value d1 may be obtained based on a center region of the face, and the second calculated value d2 may be obtained based on a region under the eyebrow of the face. As another example, the first calculated value d1 may be obtained based on the area on the eyebrow of the face, and the second calculated value d2 may be obtained based on the center area of the face. In addition, although not shown in the drawings, the first calculation value d1 and the second calculation value d2 may be obtained based on different preset areas of the face.

Referring back to FIG. 15, the controller 100 may determine the hair loss state of the user through the user hair loss state determination step S160. More specifically, the user hair loss state determination module 160 of the controller 100 may determine the user's hair loss state based on the first calculated value and the second calculated value. More specifically, the user hair loss state determination module 160 may determine the hair loss state of the user based on a ratio of the first calculated value (e.g., the upper face portion calculated value) and the second calculated value (e.g., the middle-lower face portion calculated value).

According to an embodiment, the user hair loss state determination module 160 may determine by comparing a ratio of the first calculated value and the second calculated value with a predetermined ratio. For example, the user hair loss state determination module 160 may determine that the user's hair loss state is normal when the ratio of the first calculated value and the second calculated value is compared with a predetermined ratio and satisfies the first criterion. As another example, the user hair loss state determination module 160 may compare a ratio between the first calculated value and the second calculated value with a predetermined ratio and determine that the user hair loss state is in progress when the first criterion is not satisfied.

As a more specific example, when the ratio of the first calculated value to the second calculated value is equal to or greater than a predetermined ratio, the user hair loss state determination module 160 may determine that the user hair loss state is in progress. Alternatively, when the ratio of the first calculated value to the second calculated value is less than a predetermined ratio, the user hair loss state determination module 160 may determine that the user hair loss state is normal. In this case, the predetermined ratio may mean a ratio between each part or region constituting the face. Alternatively, the predetermined ratio may mean a predetermined ratio such that each part or region constituting the face is felt stable and balanced.

Figure 17:
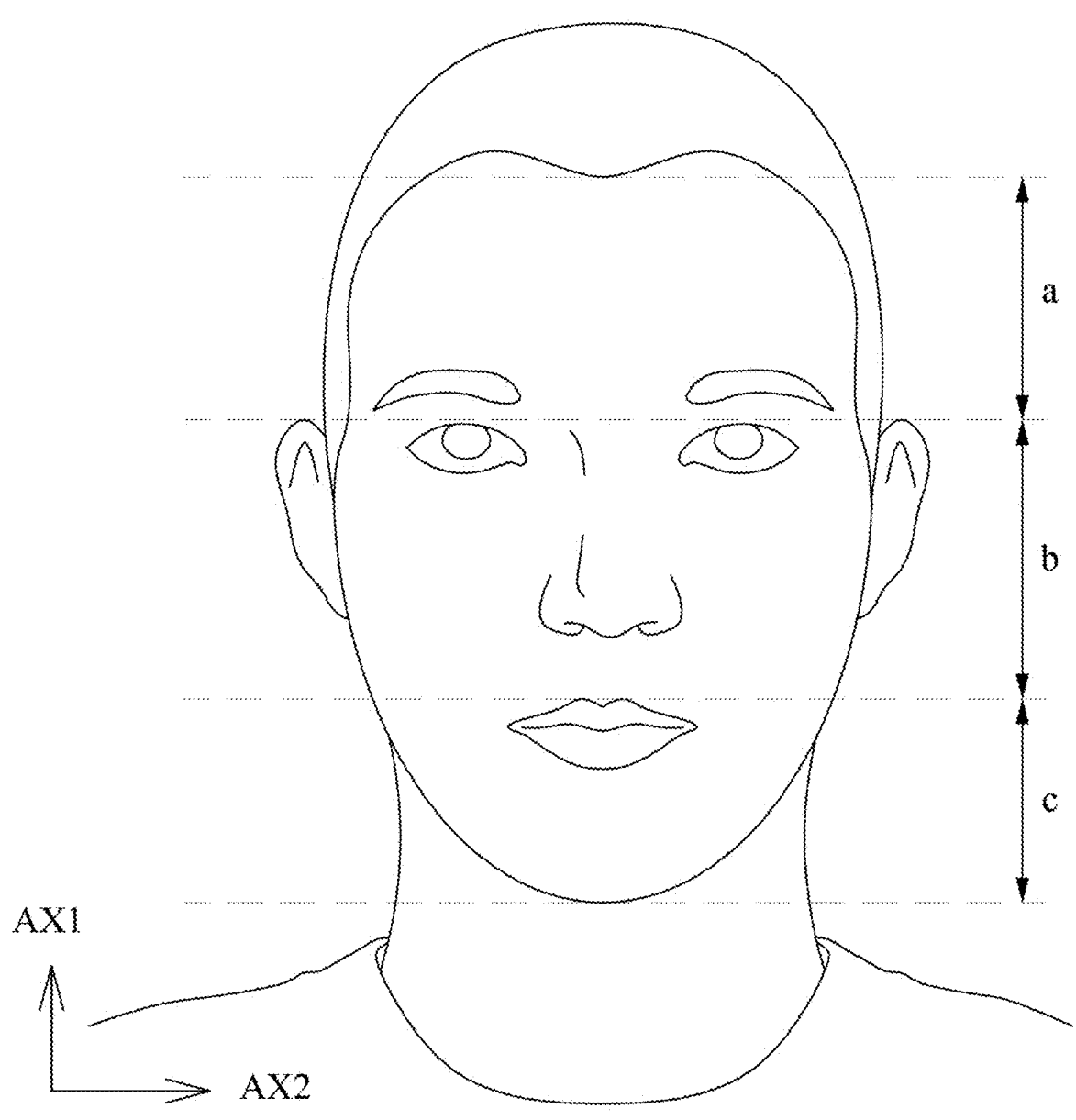
FIG. 17 is a diagram for exemplarily describing a reference ratio used when determining a hair loss state of a user.

FIG. 17 is a diagram for exemplarily describing a reference ratio used when determining a hair loss state of a user. Referring to FIG. 17, the predetermined ratio may include a ratio between a length of the upper face portion (a), a length of the middle face portion (b), and a length of the lower face portion (c). Alternatively, the predetermined ratio may include a ratio between a length of the upper face portion (a) and a length of the middle-lower face portion (b+c). More specifically, the predetermined ratio may include a ratio between a length (a) of a hair and a brow from a boundary line of a forehead and a length (b+c) of a brow from a lower portion of the brow to a chin end. In this case, the length of the upper face portion (a), the length of the middle face portion (b), and the length of the lower face portion (c) may mean a length determined based on the first axis AX1 on the head image.

Meanwhile, the predetermined ratio may be changed by the user's selection. That is, the predetermined ratio may be determined based on a ratio ideally considered by the user. For example, the predetermined ratio may be determined as a ratio based on a sample head image preferred by the user or ideally considered by the user. Accordingly, the user hair loss state determination module 160 may determine the hair loss state of the user based on the ratio reflecting the user's taste.

FIG. 18 is a flowchart illustrating a method for determining a hair loss state of a user according to another embodiment.

Referring to FIG. 18, a process for determining a hair loss state of a user according to another embodiment may include acquiring a head image of the user (S200), extracting a boundary point and a feature point from the acquired head image (S210, S220), selecting a matching boundary point of the head image (S230), extracting a reference point from the head image (S240), acquiring a first upper face portion calculation value and a second upper face portion calculation value of the head image (S250, S260), determining the hair loss state of the user based on the first upper face portion calculation value and the second upper face portion calculation value (S270), and providing hair loss state information to the user based on a result of determining the hair loss state (S280). Meanwhile, the flowchart of FIG. 18 is exemplary, and some orders of each of the steps shown in FIG. 18 may be changed.

Meanwhile, the user's head image acquiring step S200 to the matching boundary point selecting step S230 of FIG. 18 may be performed in the same manner as or corresponding to the user's head image acquiring step S100 to the matching boundary point selecting step S130 of FIG. 15.

According to another embodiment, the controller 100 may determine the hair loss state of the user by comparing the upper face portion calculation value with a reference value. The reference value may mean a value that is a reference for determining the hair loss state of the user. More specifically, the upper face portion calculation value may be a value corresponding to a current forehead region of the user acquired from the head image, and in this case, the reference value may be a value that is a reference for determining whether the upper face portion calculation value is larger or smaller than when the hair loss state of the user is normal. In this case, the reference value may be determined based on a predetermined ratio.

That is, the controller 100 may determine whether the hair loss state of the user is normal or in progress by comparing the upper face portion calculation value acquired from the head image with the reference value. For example, the controller 100 may determine the hair loss state of the user based on whether the calculated value of the upper face portion is greater than or less than the reference value. As another example, the controller 100 may determine the hair loss state of the user based on whether the calculated value of the upper face portion falls within a predetermined ratio of the reference value. Hereinafter, for convenience of description, the upper face portion calculation value is defined as a first upper face portion calculation value and the reference value as a second upper face portion calculation value.

The controller 100 may acquire the first upper face portion calculation value based on the feature point FP and the matching boundary point MBP corresponding thereto through the first upper face portion calculation value acquisition step S250. A detailed embodiment of the present disclosure corresponds to the first calculation value acquisition method described above with reference to FIGS. 15 and 16, and a redundant description thereof will be omitted.

The controller 100 may acquire the second upper face portion calculation value based on the feature point FP and the reference point RP corresponding thereto through the second upper face portion calculation value acquisition step S260. Alternatively, the controller 100 may acquire the second upper face portion calculation value based on the middle lower face portion calculation value calculated based on the plurality of feature points FP and the predetermined ratio through the second upper face portion calculation value acquisition step S260.

Meanwhile, the second upper face portion calculation value may be determined based on a distance between the feature point FP determined based on the first axis AX1 on the head image and the reference point RP corresponding thereto. Alternatively, the second upper face portion calculation value may be determined based on a distance between a coordinate of the feature point FP and a coordinate of the reference point RP corresponding thereto. For example, the second upper face portion calculation value may mean a distance value between a coordinate of the first axis AX1 of the feature point FP and a coordinate of the first axis AX1 of the reference point RP corresponding thereto.

The controller 100 may extract the reference point through the step of extracting the reference point from the head image (S240). Specifically, the reference point RP may be determined as a point that is spaced apart from the feature point FP onto the first axis AX1 by a distance of a predetermined ratio of the middle-lower face portion calculation value. For example, the reference point RP may be determined as a point that is spaced apart from the feature point of the first group G1FP in the first direction of the first axis AX1 by a distance of a predetermined ratio of the middle-lower face portion calculation value determined based on the feature point of the first group G1FP and the feature point of the second group G2FP. Hereinafter, a method of determining the reference point RP will be described in detail with reference to the drawings.

Figure 19:
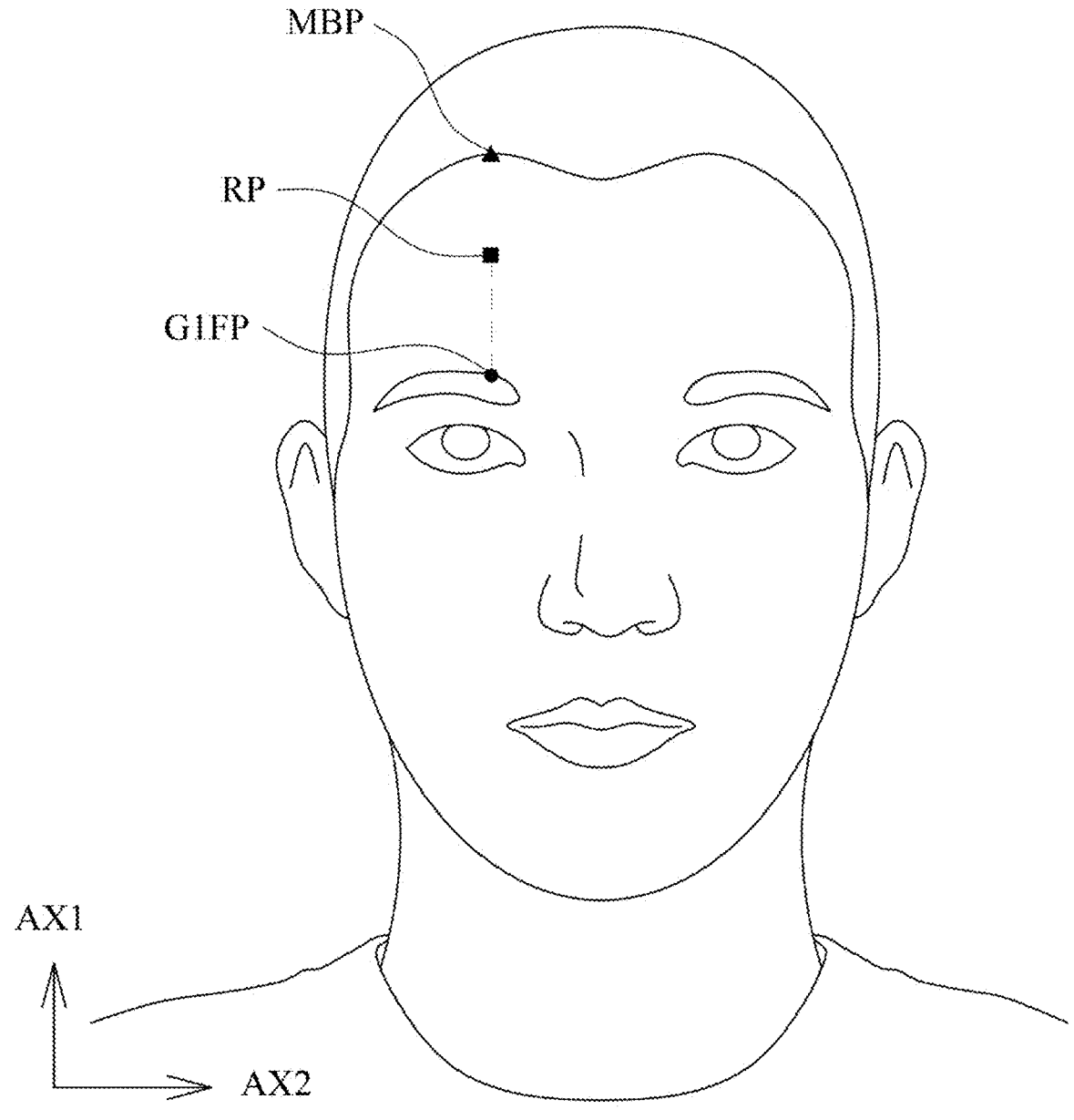
FIG. 19 is a diagram for describing a method of determining a reference point in a head image.

FIG. 19 is a diagram for describing a method of determining a reference point in a head image. Referring to FIG. 19, the reference point RP may be a point that is spaced apart from the feature point of the first group G1FP in the first direction of the first axis AX1 on the head image by a distance of a predetermined ratio of the middle-lower face portion calculation value. In other words, the reference point RP may be a point that is spaced apart from the feature point of the first group G1FP in the first direction of the first axis AX1 on the head image by a value obtained by multiplying or dividing the middle-lower face portion calculation value and the predetermined ratio. Meanwhile, the middle-lower face portion calculation value can be determined based on multiple feature points FP, and this can correspond to the second calculation value previously described through FIG. 15 and FIG. 16. In addition, the preset ratio may correspond to the ratio described above with reference to FIG. 17, and a redundant description thereof will be omitted.

The controller 100 may determine the hair loss state of the user based on the first upper face portion calculation value and the second upper face portion calculation value described above in the user hair loss state determination step S270. For example, when the first upper face portion calculation value is equal to or less than the second upper face portion calculation value, the controller 100 may determine that the hair loss state of the user is normal. Alternatively, when the first upper face portion calculation value exceeds the second upper face portion calculation value, the controller 100 may determine that the hair loss state of the user is in progress. Thereafter, in the user hair loss state information providing step S280, the controller 100 may provide the hair loss state information to the user based on the result of the user hair loss state determination.

According to another embodiment, the user hair loss state determination module 160 of FIG. 6 may determine the hair loss state of the user based on the upper face portion area value. More specifically, the user hair loss state determination module 160 may determine the hair loss state of the user based on the area value of the first upper face portion and the area value of the second upper face portion.

Here, the area value of the first upper face portion and the area value of the second upper face portion may be determined based on the user's head image. However, the area value of the first upper face portion may mean an area of the user's current forehead region (e.g., a region from a boundary line below the head carcass and a forehead from above the eyebrow in the head image), and the area value of the second upper face portion may mean an area of the user's ideal forehead region determined based on a predetermined ratio. That is, the user hair loss state determination module 160 may determine whether the hair loss of the user is in progress or normal by comparing the area of the user's current forehead region determined through the head image with the area of the user's ideal forehead region.

Meanwhile, the area value of the first upper face portion may be calculated based on a plurality of feature points FP and a plurality of matching boundary points MBP corresponding thereto. In addition, the area value of the second upper face portion may be calculated based on the plurality of feature points FP and a plurality of reference points RP corresponding thereto. Hereinafter, a method of calculating the area value of the first upper face portion and the area value of the second upper face portion will be described with reference to the drawings.

The feature point extraction module 120 of FIG. 6 may extract a plurality of feature points FP from the head image. In this case, the plurality of feature points FP extracted by the feature point extraction module 120 may include a first feature point FP1 and a second feature point FP2.

Figure 20:
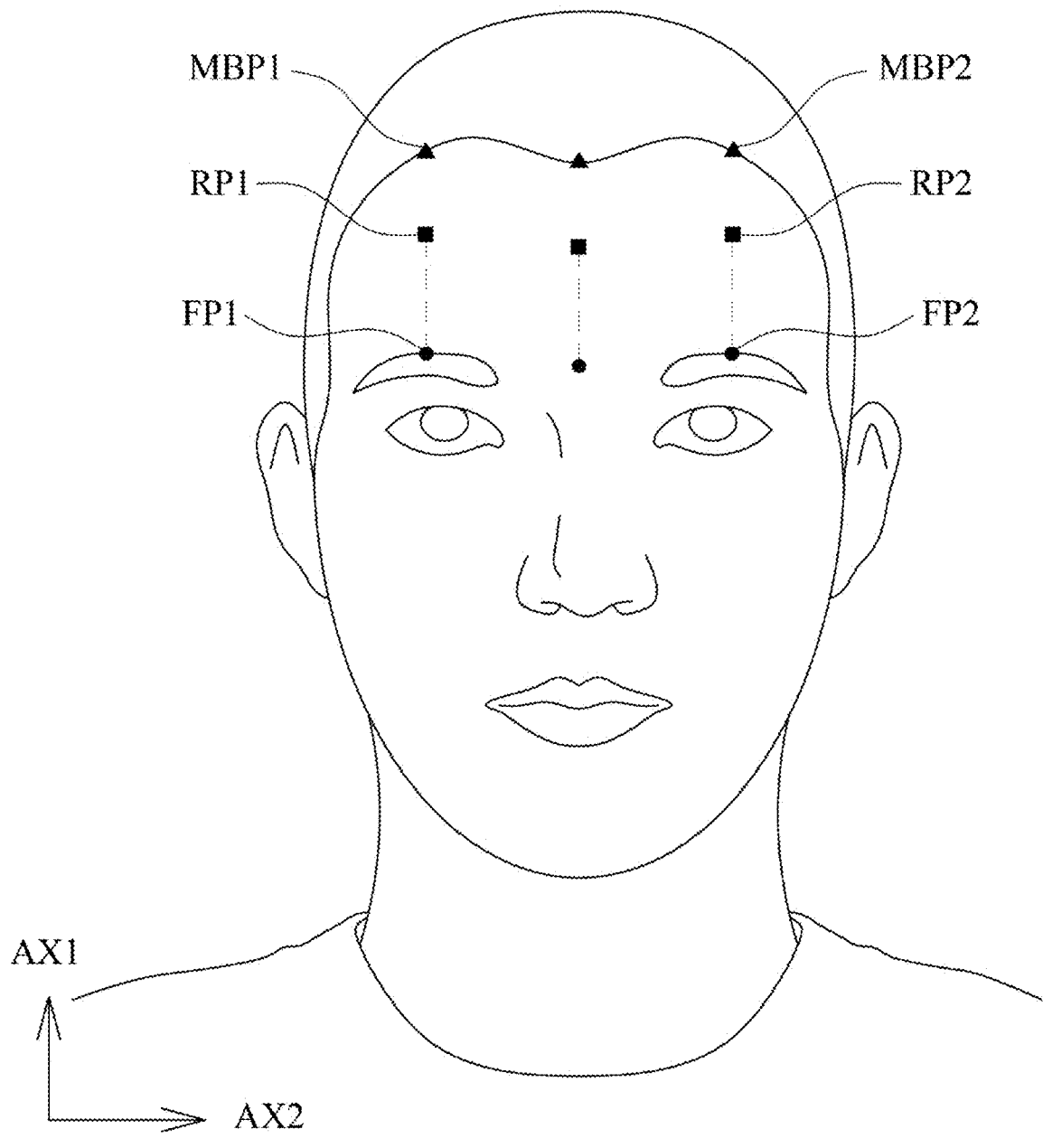
FIG. 20 is a diagram for describing a method of calculating an area of a upper face portion according to an embodiment.

FIG. 20 is a diagram for describing a method of calculating an area of an upper face portion according to an embodiment. Referring to FIG. 20, the first feature point FP1 and the second feature point FP2 may be any one of the feature points of the first group G1FP, respectively. For example, the first feature point FP1 may be any one of a plurality of feature points located in one region of the left eyebrow among the feature points of the first group G1FP. In addition, the second feature point FP2 may be any one of a feature point located in one region of the right eyebrow among the feature points of the first group G1FP. The first feature point FP1 and the second feature point FP2 may be any one of feature points located symmetrically within an error range with respect to the first axis AX1 at the center of the head image among the feature points of the first group G1FP. For example, the first feature point FP1 may be a feature point corresponding to the center of the left eyebrow among the feature points of the first group G1FP, and the second feature point FP2 may be a feature point corresponding to the center of the right eyebrow among the feature points of the first group G1FP.

The matching boundary point selection module 130 of FIG. 6 may select a plurality of matching boundary points MBP among the boundary points extracted from the head image. In this case, the selected plurality of matching boundary points MBP may include the first matching boundary point MBP1 and the second matching boundary point MBP2. Referring to FIG. 20, the matching boundary point selection module 130 may select the first matching boundary point MBP1 corresponding to the first feature point FP1. In addition, the matching boundary point selection module 130 may select the second matching boundary point MBP2 corresponding to the second feature point FP2. Meanwhile, since the method of selecting the matching boundary point MBP corresponding to the feature point FP has been described above with reference to FIGS. 11 to 14, a redundant description thereof will be omitted.

According to an additional embodiment, the controller 100 may extract a plurality of reference points from the head image. In this case, the extracted plurality of reference points may include the first reference point BP1 and the second reference point BP2. Referring to FIG. 20, the controller 100 may extract the first reference point RP1 corresponding to the first feature point FP1. In addition, the controller 100 may extract the second reference point RP2 corresponding to the second feature point FP2. Meanwhile, the plurality of reference points RP may be determined based on the feature point FP and the predetermined ratio, and since they are described above with reference to FIG. 19, a redundant description thereof will be omitted.

Figure 21:
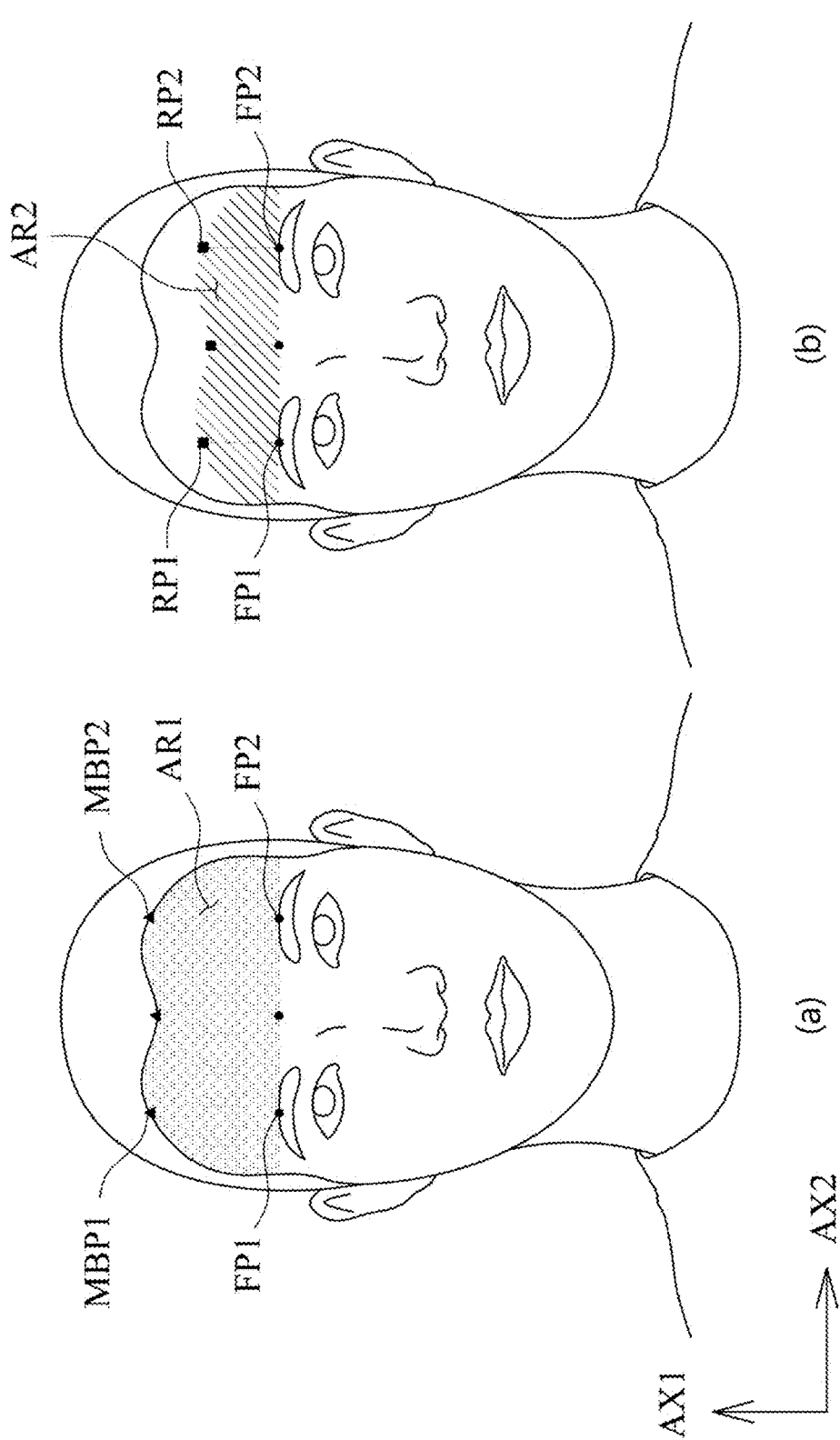
FIGS. 21 and 22 are diagrams illustrating an area of a upper face portion according to an embodiment.
Figure 22:
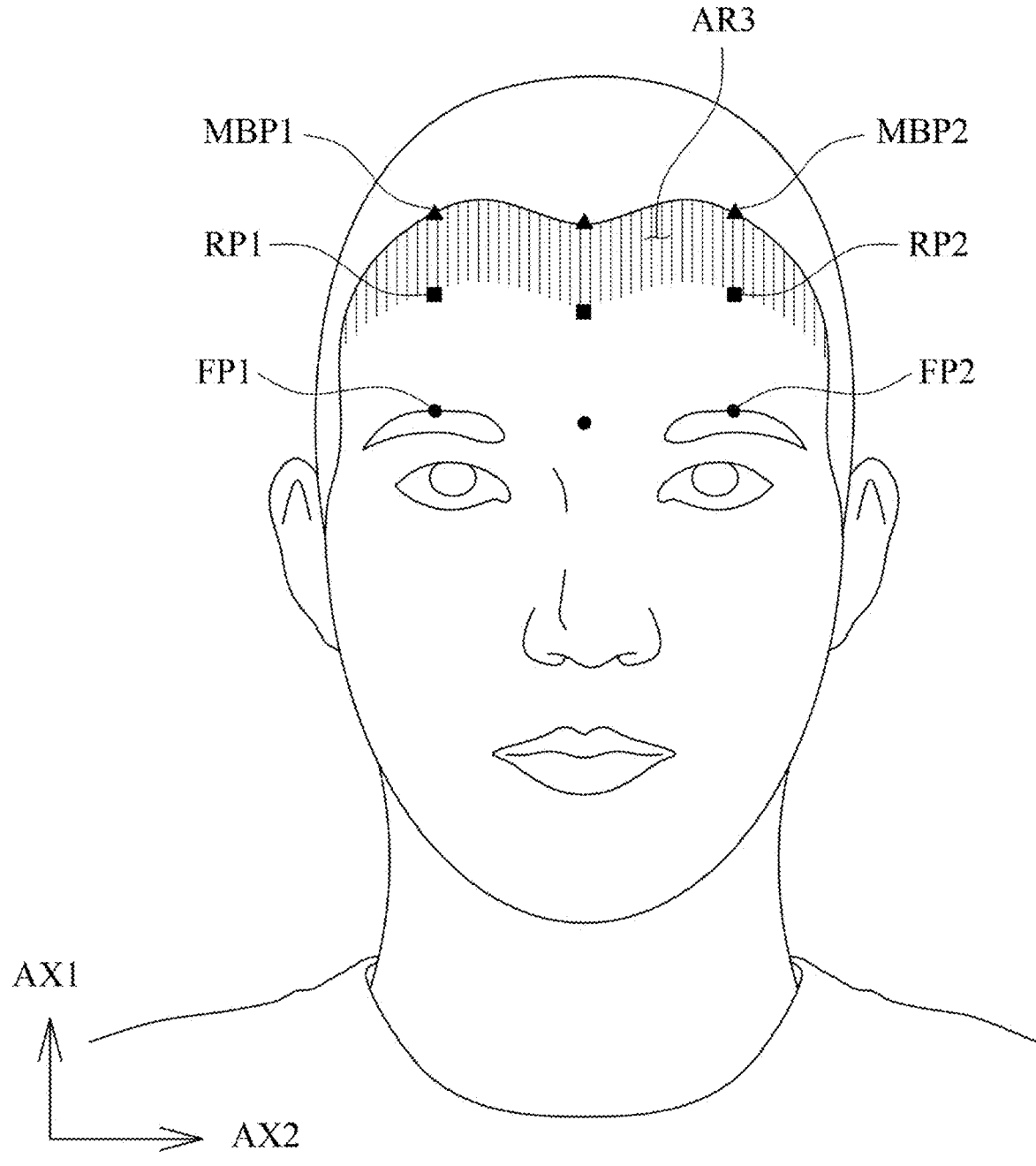

FIGS. 21 and 22 are views illustrating an area of the upper face portion according to an embodiment. Referring to FIG. 21, the upper face portion may mean a region corresponding to a boundary line between the hair and the forehead and a top portion of the eyebrow in the head image as described above.

Referring to FIG. 21(*a*), the first upper face portion AR1 may be a region determined based on the first feature point FP1, the second feature point FP2, the first matching boundary point MBP1, and the second matching boundary point MBP2. That is, the first upper face portion AR1 may correspond to a current forehead region of the user, for example, a region below the boundary line between the hair and the forehead from above the eyebrow. In addition, referring to FIG. 21(*b*), the second upper face portion AR2 may be a region determined based on the first feature point FP1, the second feature point FP2, the first reference point RP1, and the second reference point RP2. That is, the second upper face portion AR2 may correspond to an ideal forehead region of the user determined based on the predetermined ratio, for example, a region between the first reference point RP1 and the second reference point RP2 from above the eyebrow.

According to an embodiment, the controller 100 may calculate an area value of the first upper face portion AR1 based on the first feature point FP1, the second feature point FP2, the first matching boundary point MBP1, and the second matching boundary point MBP2. The controller 100 may calculate an area value of the first upper face portion AR1 based on coordinates of each of the first feature point FP1, the second feature point FP2, the first matching boundary point MBP1, and the second matching boundary point MBP2. For example, the controller 100 may calculate the area value of the first upper face portion AR1 through a trigonometric calculation method based on coordinates of each of the first feature point FP1, the second feature point FP2, the first matching boundary point MBP1, and the second matching boundary point MBP2, but is not limited thereto, and various known methods for obtaining the area using the coordinates may be used.

Meanwhile, the controller 100 may calculate the area value of the second upper face portion AR2 based on the first feature point FP1, the second feature point FP2, the first reference point RP1, and the second reference point RP1, and the detailed method is the same as the method for calculating the area value of the first upper face portion AR1, and thus a redundant description thereof will be omitted.

According to another embodiment, the controller 100 may calculate the area value of the first upper face portion AR1 based on the reference horizontal length and the first feature point FP1, the second feature point FP2, the first matching boundary point MBP1, and the second matching boundary point MBP2. Specifically, the controller 100 may obtain the vertical length of the first upper face portion AR1 based on the feature point FP and the matching boundary point MBP corresponding thereto, and calculate the area value of the first upper face portion AR1 using the obtained vertical length and the reference horizontal length.

Referring to FIG. 21, the controller 100 may calculate the area value of the first upper face portion AR1 by multiplying the vertical length of the first upper face portion AR1 (e.g., a length determined based on the first feature point FP1 and the first matching boundary point MBP1 corresponding thereto or a length determined based on the second feature point FP2 and the second matching boundary point MBP2 corresponding thereto) and the reference horizontal length. In this case, the reference horizontal length may be determined based on an aspect ratio of the user face and a preset standard face length. In this case, the aspect ratio of the user face may be a ratio of the horizontal length and the vertical length of the user face determined based on at least one of the feature point FP or the boundary point BP existing in the head image. Specifically, the vertical length of the user face may be determined based on one of the feature point FP and one of the boundary point BP. In addition, the horizontal length of the user face may be determined based on a plurality of feature points FP or a plurality of boundary points BP.

Meanwhile, the preset standard face length may include a preset standard face horizontal length or a vertical length. For example, the preset standard face length may be an average vertical (or horizontal) length of a male (or female) face. For example, the reference horizontal length may be determined based on the vertical length of the preset standard male face and the aspect ratio of the user face.

FIG. 22 is a diagram for describing a method of determining a hair loss state of a user based on a first upper face portion and a second upper face portion by a user hair loss state determination module. Referring to FIG. 22, the user hair loss state determination module 160 may determine the hair loss state of the user based on the first upper face portion AR1 area value and the second upper face portion AR2 area value.

More specifically, the user hair loss state determination module 160 may determine the hair loss state of the user based on a difference between the first upper face portion AR1 area value and the second upper face portion AR2 area value. Alternatively, the user hair loss state determination module 160 may determine the hair loss state of the user based on a ratio between the first upper face portion AR1 area value and second upper face portion AR2 area value.

For example, the user hair loss state determination module 160 may determine the user's hair loss state based on an area value of the first upper face portion AR1 being larger or smaller than an area value of the second upper face portion AR2 (i.e., a reference area value). For example, when the area value of the first upper face portion AR1 is smaller than the area value of the second upper face portion AR2, the user hair loss state determination module 160 may determine that the user hair loss state is normal. Further, when the area value of the first upper face portion AR1 is greater than the area value of the second upper face portion AR2, the user hair loss state determination module 160 may determine that the user hair loss state is in progress. As another example, the user hair loss state determination module 160 may determine the hair loss state of the user in a stepwise manner based on a ratio of an area value of the first upper face portion AR1 and an area value of the second upper face portion AR2.

Figure 23:
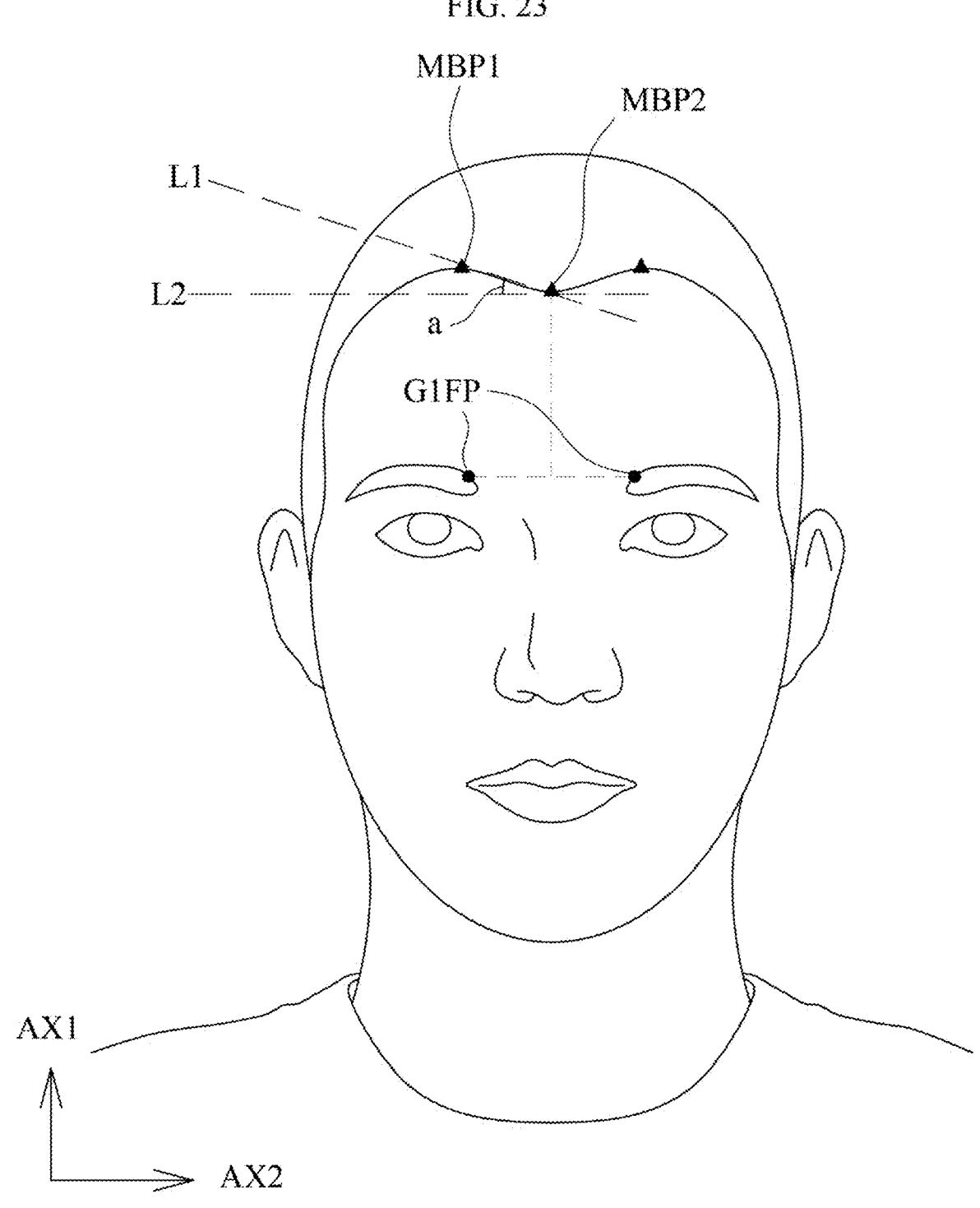
FIG. 23 is a diagram for describing a method of determining a hair loss state of a user according to another embodiment.

FIG. 23 is a diagram for describing a method for determining a hair loss state of a user according to another embodiment. Hereinafter, a method for determining a hair loss state of a user according to another embodiment will be described with reference to FIG. 23.

Referring to FIG. 23, the user hair loss state determination module 160 may determine the user's hair loss state based on the feature point of the first group G1FP and the matching boundary point MBP. The user hair loss state determination module 160 may determine the user's hair loss state based on the first matching boundary point MBP1 and the second matching boundary point MBP2 selected corresponding to at least one of the feature point of the first group G1FP.

The first matching boundary point MBP1 may be a boundary point having the highest first axis AX1 coordinate value on the head image among matching candidate boundary points MCBP corresponding to feature points located in one region of the left or right eyebrows. This is described above in FIG. 13(*c*), and thus a redundant description is omitted. The second matching boundary point MBP2 may be a boundary point corresponding to a middle portion of the forehead in the head image. According to an embodiment, the second matching boundary point MBP2 may be selected based on a plurality of feature points of the first group G1FP. For example, the second matching boundary point MBP2 may be selected to correspond to a first feature point located in one region of the left eyebrow and a second feature point located in one region of the right eyebrow among the feature points of the first group G1FP. Meanwhile, the second matching boundary point MBP2 in FIG. 23 may correspond to the sixth matching boundary point MBP6 of FIG. 12.

The user state determination module 160 may determine the hair loss state of the user based on an angle a formed by the straight line connecting the first matching boundary point MBP1 and the second matching boundary point MBP2 and the second axis AX2. For example, when the angle (M-shaped angle) between the straight line connecting the first matching boundary point MBP1 and the second matching boundary point MBP2 and the second axis AX2 is equal to or greater than a predetermined reference, the user state determination module 160 may determine that the user's hair loss is in progress, and when the angle between the straight line connecting the first matching boundary point MBP1 and the second matching boundary point MBP2 is less than the predetermined reference, the user state determination module 160 may determine that the user's hair loss is normal.

As described above, when the user determines whether the user has hair loss based on the boundary point between the user's hair and the forehead, the user hair loss state determination module 160 may more accurately determine the user's M-shaped hair loss.

Figure 24:
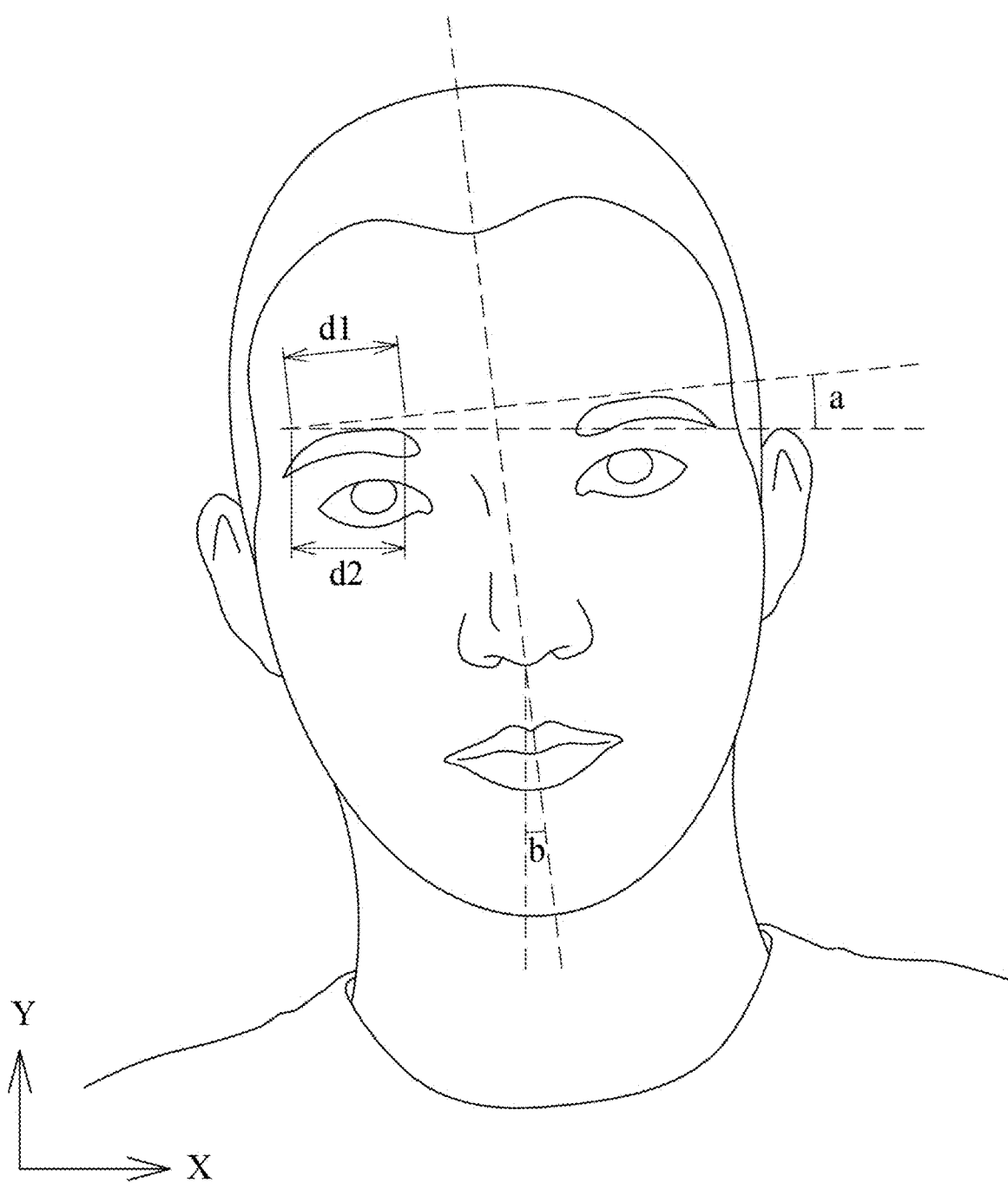
FIG. 24 is a diagram for describing a method of recalibrating an image based on an angle of inclination of a user's head in a head image.

FIG. 24 is a diagram for describing a method of recalibrating an image based on an angle of tilt of a user's head in a head image.

The user's head may be photographed in a state in which the user's head is inclined in a three-dimensional manner on the head image. In this case, the measured length of the main portion of the user's face, e.g., the eyes, nose, leaves, ears, etc., included in the head image may be different from the actual length according to the angle of inclination. Accordingly, the measured length of the main portion included in the head image needs to be corrected based on the angle at which the user's head is inclined in the head image. In this case, the measured length may mean a length obtained by measuring a length of a main portion of the user's face in an X-axis or a Y-axis direction on the head image.

Referring to FIG. 24, in the photographed head image, the user's head may be inclined at a predetermined angle with respect to the X-axis or the Y-axis on the image. Specifically, the user's head may be inclined by an angle theta_a of a straight line extending a left eyebrow top portion of the user on an X-axis and a straight line connecting the left eyebrow top portion and the right eyebrow top portion. Alternatively, the user's head may be inclined by an angle theta_b formed by a straight line connecting the user's nose and jaw tip and a straight line extending the nose tip on the Y-axis.

In this case, the actual length of the user's face major portion may be determined according to a ratio of the measured length and the angle of inclination theta_a or theta_b. For example, when the user's face is tilted so that the right eyebrow is higher than the left eyebrow, the actual length of the left eyebrow may be the length obtained by dividing the measured length of the left eyebrow by the cos(theta_a) value, and the actual length of the right eyebrow may be the length obtained by multiplying the measured length of the right eyebrow by the cos(theta_b) value.

As another example, when the user's face is tilted so that the left eyebrow is higher than the right eyebrow, the actual length of the left eyebrow may be a length obtained by multiplying the measured length of the left eyebrow by a value of cos(theta_a), and the actual length of the right eyebrow may be a length obtained by dividing the measured length of the right eyebrow by a value of cos(theta_a). As another example, the actual length from the end of the nose center to the bottom of the lower lip center of the user may be the length divided by the measured length by the value of cos(theta_b). In this case, the measured length may be a Y-axis direction length from the end of the nose center to the bottom of the lower lip center. As another example, the actual length from the base of the user's lower lip center to the chin end may be the length divided by the measured length by the value of cos(theta_b). In this case, the measured length may be a Y-axis direction length from the base of the lower lip center to the chin end.

The actual length related to the major portion of the user's face measured by the above-described method may be used to determine the state of hair loss of the user, or may be used to compare the ratio of the major portion of the user's face with a predetermined ratio.

Figure 25:
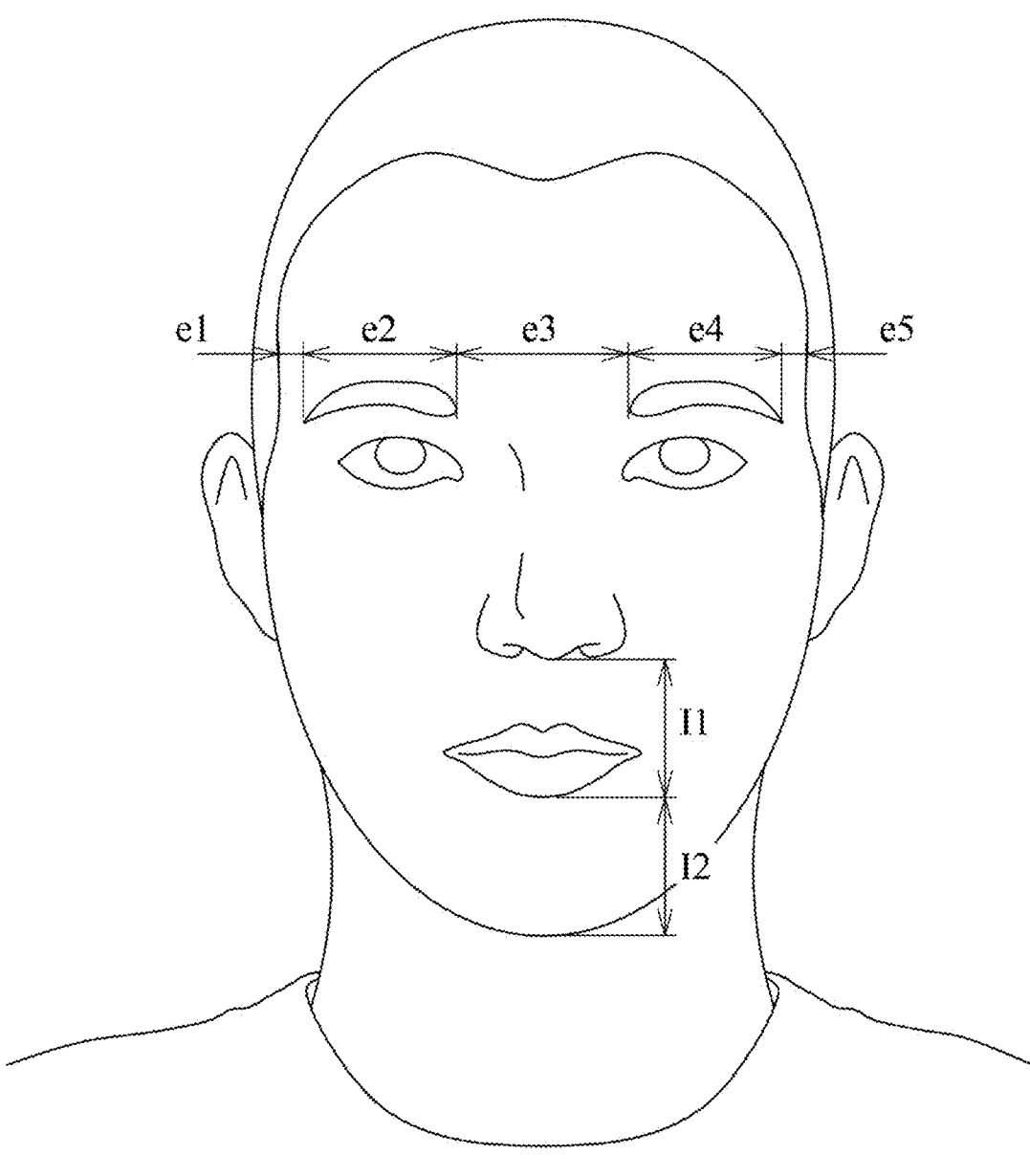
FIG. 25 is a diagram for describing a detailed ratio related to a major portion of a user's face.

FIG. 25 is a diagram for describing a detailed ratio related to a major portion of a user's face. Referring to FIG. 25, various detailed ratios related to major parts of the face may be measured from the user's head image, and the user's hair loss may be determined based on the measured detailed ratios. Alternatively, the measured detail ratio may be used when a ratio of a major portion of the user's face is compared with a predetermined ratio.

The output unit 500 may output information related to the hair loss state of the user determined by the controller 100 through the user hair loss state determination module 160. For example, the output unit 500 may output user hair loss state information determined based on a first calculation value and/or a second calculation value from the controller 100. Alternatively, the output unit 500 may output user hair loss state information determined based on at least one of a plurality of feature points FP and a plurality of boundary points BP extracted or selected from the controller 100. Alternatively, the output unit 500 may output user hair loss state information determined based on a first upper face portion area value and/or a second upper face portion area value from the controller 100. The above-described information related to the hair loss state of the user may include various information such as, for example, information about whether hair loss is being progressed to the user, a degree of hair loss, a type of hair loss, and an area requiring a treatment.

The output unit 500 may output information about a treatment area. The output unit 500 may output information about a treatment area determined based on information acquired through the user hair loss state determination module 160. The treatment area may refer to an area requiring a hair implantation on the head due to hair loss generated by the user. Alternatively, the treatment area may refer to an area desired by the user to implant a hair on the head. In other words, the treatment area may refer to an area determined by the user that a hair implantation is needed on the head.

For example, the treatment area may be determined based on the first upper face portion AR1 area value and the second upper face portion AR2 area value described with reference to FIGS. 21 and 22. More specifically, the treatment area may be determined based on an area AR3 corresponding to a difference between the first upper face portion AR1 and the second upper face portion AR2.

The output unit 500 may output the treatment area in a text or image format. For example, when the output unit 500 outputs the treatment area in the text format, the output unit 500 may output information about an area value of the area requiring the treatment, a number of hair follicles to be treated in the treatment area, and the like together. As another example, when the output unit 500 outputs the treatment area in the image format, the output unit 500 may output a head image after a hair has been implanted in the treatment area, that is, a head image after a user's treatment.

Figure 26:
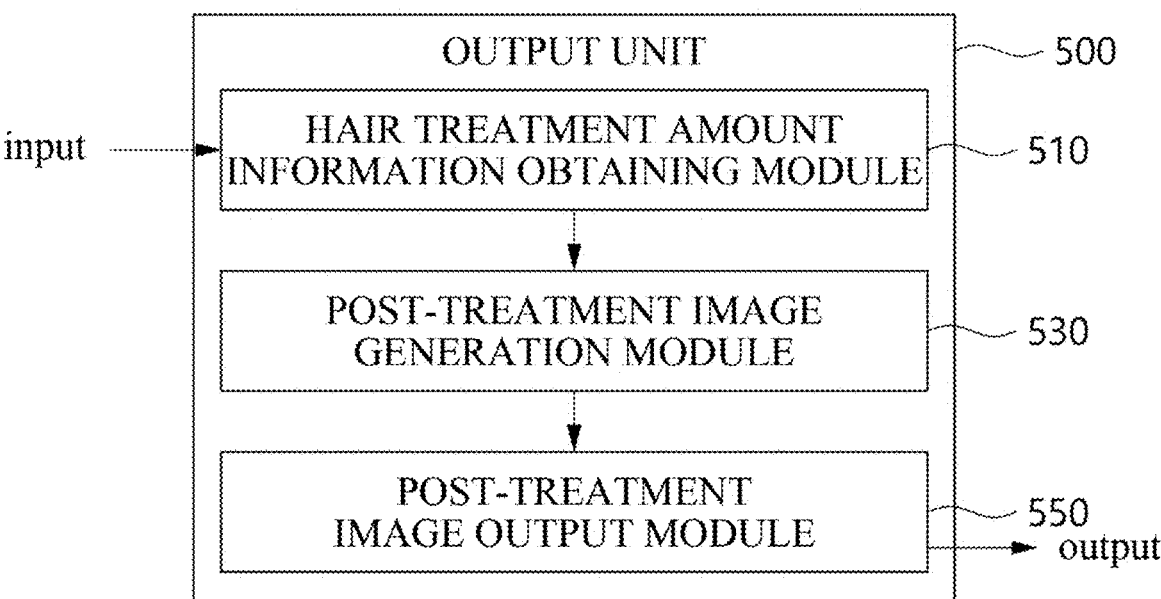
FIGS. 26 and 27 are diagrams for describing an output unit outputting information related to a hair loss state of a user based on user input information.
Figure 27:
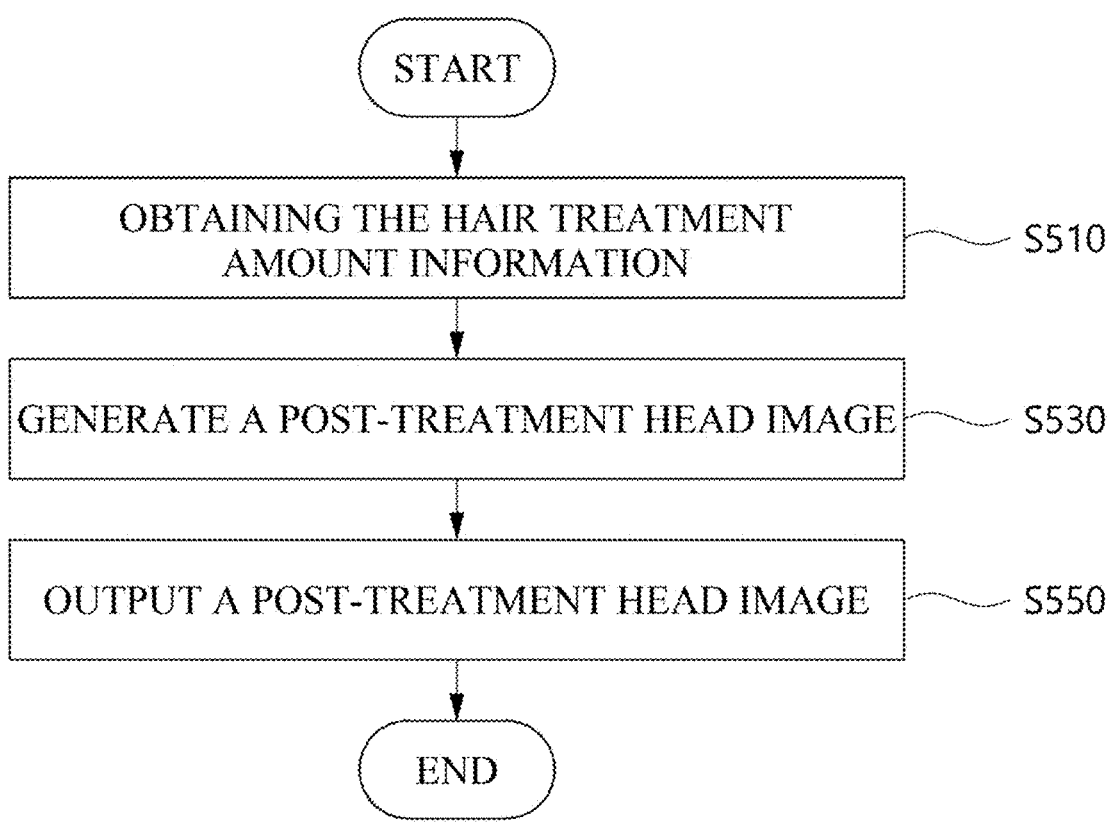
Figure 28:
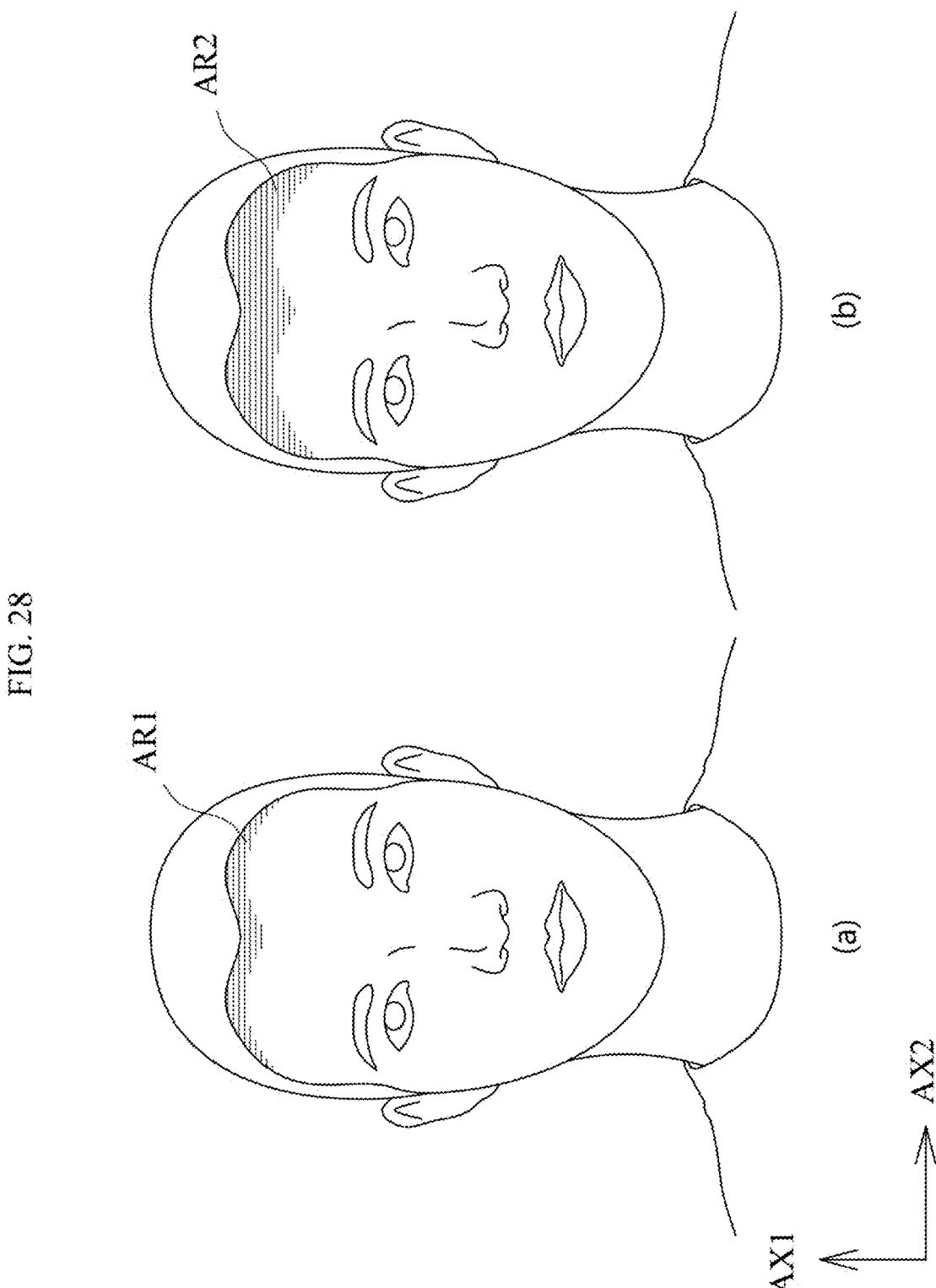
FIGS. 28 and 29 are diagrams for exemplarily describing an output unit outputting a head image after a user's treatment.
Figure 29:
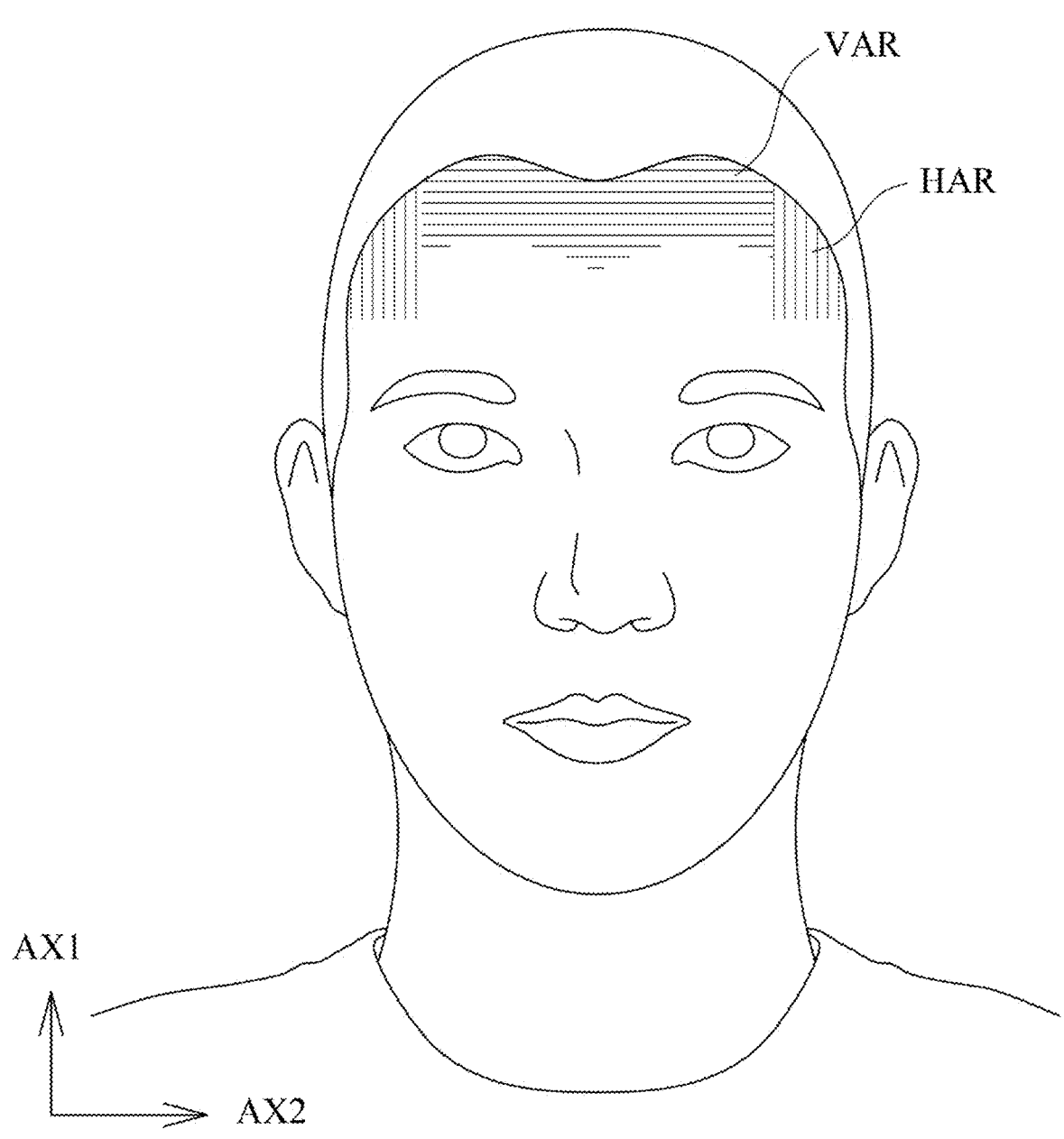

FIGS. 26 and 27 are diagrams for describing outputting information related to the hair loss state of the user based on user input information, and FIGS. 28 and 29 are diagrams for exemplarily describing outputting a head image after a user's treatment. Hereinafter, a method of outputting information related to the hair loss state of the user based on user input information by the output unit will be described with reference to FIGS. 26 to 29.

Referring to FIGS. 26 and 27, the output unit 500 may output information related to the hair loss state based on user input information acquired through the user input unit 400. The output unit 500 may output a head image after a user's treatment based on user input information acquired through the user input unit 400.

The hair treatment amount information obtaining module 510 of the output unit 500 may obtain the hair treatment amount information through the step S510 of obtaining the hair treatment amount information from the user or the third party. Here, the hair treatment amount information is information input by the user or the third party and may include information about the number of hair follicles, the type of hair to be treated, the treatment area, the treatment site, the treatment method, and the like. The post-treatment image generation module 530 may generate a post-treatment head image of the user through the step S530 of generating the post-treatment image.

Referring to FIG. 28, the post-treatment image output module 550 may output a post-treatment head image of the user in the step S550 of outputting the post-treatment image. The post-treatment image output module 550 may output an image about a treatment area determined based on the user input information. The treatment area may include a first treatment area and a second treatment area different from the first treatment area, and the first treatment area may be an area determined when the hair treatment amount input by the user is the first treatment amount, and the second treatment area may be an area determined when the hair treatment amount input by the user is the second treatment amount.

Referring to FIG. 28(a), when the hair treatment amount obtained by the hair treatment amount information obtaining module 510 is the first treatment amount, the treatment area may be determined as the first treatment area AR1. Referring to FIG. 28(b), when the hair treatment amount obtained by the hair treatment amount information obtaining module 510 is the second treatment amount, the treatment area may be determined as the second treatment area AR2. In this case, the second treatment amount may be larger than the first treatment amount.

Referring to FIG. 29, for example, the post-treatment head image output by the post-treatment image output module 550 may be an image about a region VAR simulated to gradually implant hair from a boundary line of a user's hair and a forehead in a second direction of a first axis AX1 (a direction from a mother toward a jaw) on the head image based on the input hair treatment amount. As another example, the post-treatment head image output by the post-treatment image output module 550 may be an image about a region HAR simulated to gradually implant hair from a boundary line of a user's hair and a forehead in a second axis AX2 on the head image based on the input hair treatment amount. As the output unit 500 provides a post-treatment head image for implanting hair based on the direction of the first axis and/or the second axis, more precise simulation information may be provided to the user.

According to an embodiment of the present disclosure, a method of selecting images for analysis to provide hair loss diagnosis assistance information, the method comprising: obtaining a plurality of scalp images including a first scalp image and a second scalp image; obtaining pore region information included in each scalp image; based on the pore region information of the first scalp image, obtaining first quantitative information related to the number of pore regions included in the first scalp image; based on the pore region information of the second scalp image, obtaining second quantitative information related to the number of pore regions included in the second scalp image; and selecting a target image by comparing the first quantitative information and the second quantitative information.

According to an embodiment of the present disclosure, wherein selecting the target image, further comprising: selecting a valid scalp image based on a result of comparing the first quantitative information and the second quantitative information; obtaining a manually captured scalp image; obtaining third quantitative information related to the number of pore regions included in the manually captured scalp image; and determining the target image based on quantitative information related to the valid scalp image and the third quantitative information related to the manually captured scalp image.

According to an embodiment of the present disclosure, wherein selecting the target image, further comprising: determining an image having a greater value of quantitative information as the target image by comparing the quantitative information related to the valid scalp image and the third quantitative information related to the manually captured scalp image.

According to an embodiment of the present disclosure, wherein obtaining pore region information, further comprising: obtaining initial pore region information related to the pore region included in the scalp image; and obtaining the pore region information by correcting the initial pore region information.

According to an embodiment of the present disclosure, wherein obtaining pore region information is performed by an artificial neural network configured to obtain the pore region information based on the scalp image.

According to an embodiment of the present disclosure, wherein the correcting the initial pore region information, further comprising: obtaining first information related to the pore region included in the scalp image; obtaining second information related to the hair region included in the scalp image; and correcting the initial pore region information based on whether the first information and the second information included in the common region range of the scalp image correspond to each other.

According to an embodiment of the present application, wherein the correcting the initial pore region information, further comprising: obtaining first location information and second location information related to the pore region included in the initial pore region information; verifying the validity of the first location information and the second location information based on whether the separation distance between the first location information and the second location information is within a predetermined distance; and determining at least one of first location information and the second location information to be invalid if the separation distance between the first location information and the second location information is within a predetermined distance; determining the first location information and the second location information to be valid if the separation distance between the first location information and the second location information is not within the predetermined distance; determining a pore region corresponding to the location information determined to be valid as the pore region information when it is determined that at least one of the first location information and the second location information is invalid.

According to an embodiment of the present application, a computer-readable recording medium having recorded thereon a program for executing the method of selecting a target image may be provided.

According to an embodiment of the present application, a scalp measuring device for obtaining scalp images comprising a camera configured to capture a plurality of scalp images and an at least one processor configured to select images for analysis to provide hair loss diagnosis assistance information based on the plurality of scalp images; wherein the at least one processor is configured to: obtain the plurality of scalp images including a first scalp image and a second scalp image; obtain pore region information included in each scalp image; based on the pore region information of the first scalp image, obtain first quantitative information related to the number of pore regions included in the first scalp image; based on the pore region information of the second scalp image, obtain second quantitative information related to the number of pore regions included in the second scalp image; and select a target image by comparing the first quantitative information and the second quantitative information.

According to an embodiment of the present application, wherein the at least one processor is configured to select the target image by performing the steps below: selecting a valid scalp image based on a result of comparing the first quantitative information and the second quantitative information; obtaining a manually captured scalp image; obtaining third quantitative information related to the number of pore regions included in the manually captured scalp image; and determining the target image based on quantitative information related to the valid scalp image and the third quantitative information related to the manually captured scalp image.

According to an embodiment of the present application, wherein the at least one processor is configured to determine an image having a greater value of quantitative information as the target image by comparing the quantitative information related to the valid scalp image and the third quantitative information related to the manually captured scalp image. wherein the at least one processor is configured to obtain initial pore region information related to the pore region included in the scalp image; and obtain the pore region information by correcting the initial pore region information.

According to an embodiment of the present application, wherein the at least one processor is configured to obtain pore region information based on an artificial neural network configured to obtain the pore region information based on the scalp image.

According to an embodiment of the present application, wherein the at least one processor is configured to: obtain first information related to the pore region included in the scalp image; obtain second information related to the hair region included in the scalp image; and correct the initial pore region information based on whether the first information and the second information included in the common region range of the scalp image correspond to each other.

According to an embodiment of the present application, wherein the at least one processor is configured to: obtain first location information and second location information related to the pore region included in the initial pore region information; verify the validity of the first location information and the second location information based on whether the separation distance between the first location information and the second location information is within a predetermined distance; and determining at least one of first location information and the second location information to be invalid if the separation distance between the first location information and the second location information is within a predetermined distance; determining the first location information and the second location information to be valid if the separation distance between the first location information and the second location information is not within the predetermined distance; determine a pore region corresponding to the location information determined to be valid as the pore region information when it is determined that at least one of the first location information and the second location information is invalid.

According to an embodiment of the present application, an electronic device for receiving a scalp image from an external scalp measuring device, the electronic device including: a transceiver configured to communicate data with the scalp measuring device; and a controller configured to acquire a plurality of scalp images including a first scalp image and a second scalp image through the transceiver, and select an analysis target image for providing hair loss diagnosis assistance information based on the plurality of scalp images, wherein the controller may be configured to acquire the plurality of scalp images, acquire pore region information included in each scalp image, obtain first quantitative information related to a number of pore regions included in the first scalp image based on the pore region information of the first scalp image, obtain second quantitative information related to a number of pore regions included in the second scalp image based on the pore region information of the second scalp image, and select a target image by comparing the first quantitative information and the second quantitative information.

According to an embodiment of the present application, the controller of the electronic device according to an embodiment of the present application may be configured to select an valid scalp image based on a result of comparing the first quantitative information and the second quantitative information, acquire a passive photographed scalp image, acquire third quantitative information related to a number of pore regions included in the passive photographed scalp image, and determine a target image based on the quantitative information related to the valid scalp image and the third quantitative information related to the passive photographed scalp image.

According to an embodiment of the present application, the controller of the electronic device according to an embodiment of the present application may be configured to compare the quantitative information related to the valid scalp image and the third quantitative information related to the passive photographed scalp image to select an image having a larger quantitative information as the target image.

According to an embodiment of the present application, the controller of the electronic device according to an embodiment of the present application may be configured to acquire pore region initial information related to a pore region included in a scalp image, and acquire the pore region information by correcting the pore region initial information.

According to an embodiment of the present application, the controller of the electronic device according to an embodiment of the present application may be configured to acquire the initial pore region information through an artificial neural network trained to acquire the initial pore region information based on the scalp image.

According to an embodiment of the present application, the controller of the electronic device according to an embodiment of the present application may be configured to acquire first information related to a pore region included in the scalp image, acquire second information related to a hair region included in the scalp image, and correct the initial pore region information based on whether the first information and the second information included in a common area range of the scalp image correspond to each other.

According to an embodiment of the present application, the controller of the electronic device according to an embodiment of the present application may be configured to acquire first location information and second location information related to a pore region included in the initial pore region information, verify validity of the first location information and the second location information based on whether a separation distance between the first location information and the second location information is within a predetermined distance, determine that at least one of the first location information and the second location information is invalid if the separation distance between the first location information and the second location information is within the predetermined distance, determine that the first location information and the second location information are invalid if the separation distance between the first location information and the second location information is not within the predetermined distance, and determine that the pore region corresponding to the location information determined to be invalid as the pore region information if the at least one of the first location information and the second location information is determined to be invalid.

Hereinafter, a scalp image analysis method, a scalp image analysis device, and a scalp image analysis system according to an embodiment of the present application will be described. Here, the analysis of the scalp image may mean all operations that may be performed to acquire assistance information that may be considered for diagnosing hair loss from the scalp image. The present application discloses various techniques for improving the accuracy and reliability of scalp image analysis, such as a method of optimally selecting a scalp image that is based on acquiring hair loss diagnosis assistance information.

Hereinafter, a scalp image analysis method, a scalp image analysis device, and a scalp image analysis system according to an embodiment of the present application will be described.

Figure 30:
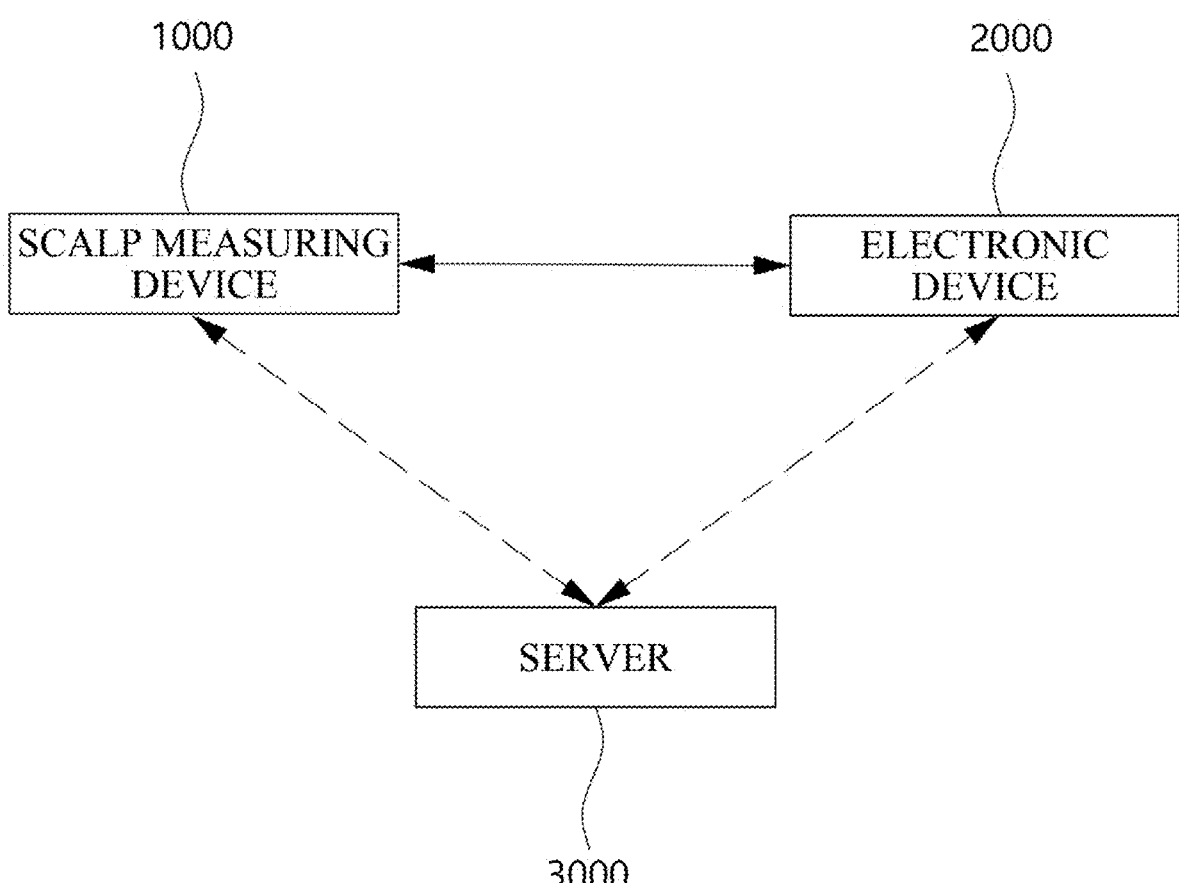
FIG. 30 is a schematic diagram illustrating a scalp image analysis system according to an embodiment of the present application.

FIG. 30 is a schematic diagram illustrating a scalp image analysis system according to an embodiment of the present application. Referring to FIG. 30, a scalp image analysis system according to an embodiment of the present application may include a scalp measuring device 1000, an electronic device 2000, and a server 3000.

The scalp measuring device 1000 may acquire a scalp image. In addition, the scalp measuring device 1000 may acquire sensing data related to the scalp, for example, temperature data, humidity data, odor data, or the like. The scalp measuring device 1000 may select a target image to be analyzed to acquire hair loss diagnosis assistance information from among the acquired scalp images. The scalp measuring device 1000 may transmit the acquired scalp image and/or the sensing data to the electronic device 2000 or the server 3000 through a certain network.

Figure 31:
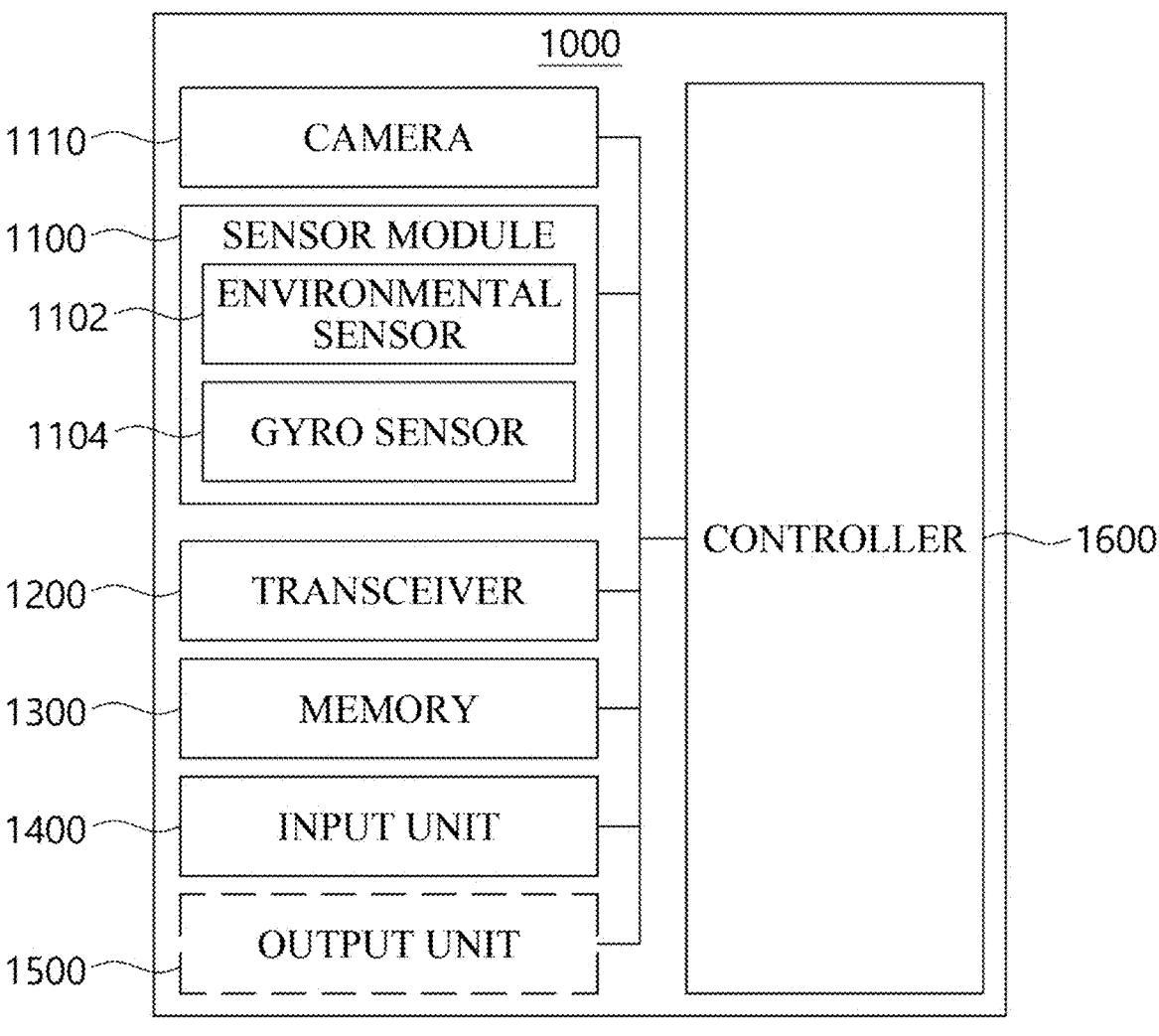
FIG. 31 is a schematic block diagram illustrating a scalp measuring device 1000 according to an embodiment of the present application.

Hereinafter, a configuration of the scalp measuring device 1000 according to an embodiment of the present application will be described with reference to FIGS. 31 and 32. FIG. 31 is a schematic block diagram illustrating a scalp measuring device 1000 according to an embodiment of the present application. FIG. 32 is a diagram illustrating an external structure and an internal structure of a scalp measuring device 1000 according to an embodiment of the present application.

The scalp measuring device 1000 according to an embodiment of the present application may include a sensor module 1100, a camera 1110, a transceiver 1200, a memory 1300, an input unit 1400, an output unit 1500, and a controller 1600.

The sensor module 1100 may acquire sensing data such as temperature data, humidity data, and odor data related to the scalp. To this end, the sensor module 1100 may include an environmental sensor 1102 and/or a gyro sensor 1104.

The camera 1110 may capture an image. In this case, the user may capture a scalp image by adjacent the camera 1110 to the scalp. For example, as the capture mode of the scalp measuring device 1000 is activated, the camera 1110 may continuously capture the scalp. For another example, the camera 1110 may capture the scalp image based on a user input indicating capture of the scalp image received through the input unit 1400.

Meanwhile, the scalp measuring device 1000 may include a light source for capturing an image. According to an embodiment of the present application, the scalp measuring device 1000 may include a white LED. In this case, the camera 1110 may capture a scalp image corresponding to the white light source. In addition, according to an additional embodiment of the present application, the scalp measuring device 1000 may include a UV-A LED. In this case, the camera 1110 may capture a scalp image corresponding to the UV-A light source.

The camera 1110 according to an embodiment of the present application may include a filter for filtering light of a predetermined wavelength band. For example, when the camera 1110 captures a scalp image using a light source through the UV-A LED, information related to the scalp characteristic (e.g., porphyrin or sebum information) may not be measured relatively clearly due to light of a blue wavelength band emitted from the corresponding light source reflected from the skin and introduced into the camera. To solve the above problem, the camera 1110 according to an embodiment of the present application may include a blue-cut filter for filtering light of a wavelength (e.g., 360 nm to 440 nm) of a specific region introduced into the camera. Accordingly, the camera 1110 according to an embodiment may acquire a scalp image in which light of a specific wavelength band (e.g., 360 nm to 440 nm) is blocked by the blue-cut filter. As described above, according to an embodiment of the present application, accuracy of analysis of the scalp image may be improved by using the camera including the blue-cut filter.

The environmental sensor 1102 may acquire sensing data including temperature data, humidity data, and/or odor data related to the scalp. The sensing data may be a basis for calculating hair loss diagnosis assistance information of a user. For example, the environmental sensor 1102 may include a temperature sensor for measuring a temperature of the scalp, a moisture sensor for measuring a humidity of the scalp, and/or a total volatile organic compound (TVOC) sensor for measuring odor data of the scalp.

Meanwhile, the gyro sensor 1104 may acquire angle data (or direction data) indicating an angle of the scalp measuring device 1000. The angle data may be used to recognize a scalp image of a user measuring a specific scalp area, as described below with reference to FIGS. 59 to 61. According to an embodiment, the angle data may be in the form of coordinate data.

Referring back to FIGS. 31 and 32, according to an embodiment, a plurality of sensors such as a temperature sensor, a moisture sensor, and/or a TVOC sensor may be embedded as one module to configure the environmental sensor 1102. Meanwhile, in the above-described embodiment, the sensor module 1100 is described as including both the temperature sensor, the environmental sensor 1102 including the moisture sensor and/or the TVOC sensor, and the gyro sensor 1104, but this is merely an example, and at least one of the above-described sensors may be omitted or a sensor not shown in FIG. 31 may be added. In addition, although the sensor module 1100 and the camera 1110 are illustrated as physically separated structures in FIG. 31, this is merely an example, and the camera 1110 may be provided as a structure physically coupled with the sensor module 1100.

Meanwhile, referring to FIG. 32, the above-described white LED and/or the UV-A LED may be disposed around the camera 1110. Through this, the camera 1110 may capture a scalp image corresponding to white light and/or a scalp image corresponding to UV light.

The transceiver 1200 may communicate with any external device including the electronic device 2000 and the server 3000. For example, the scalp measuring device 1000 may transmit the scalp image or the target image to the electronic device 2000 or the server 3000 through the transceiver 1200. In addition, the scalp measuring device 1000 may transmit temperature data, humidity data, odor data, and the like related to the scalp to the electronic device 2000 or the server 3000 through the transceiver 1200. In addition, the scalp measuring device 1000 may transmit data related to the tilting of the scalp measuring device 1000 to the electronic device 2000 or the server 3000 through the transceiver 1200.

In addition, the scalp measuring device 1000 may receive hair loss diagnosis assistance information or information (e.g., parameter set information of a neural network model) for operation of the scalp measuring device 1000 from the server 3000 through the transceiver 12000. The scalp measuring device 1000 may access a network through the transceiver 1200 to transmit and receive various data. The transceiver 1200 may include a wired type and a wireless type. Since the wired type and the wireless type have advantages and disadvantages, the wired type and the wireless type may be simultaneously provided in the scalp measuring device 1000 in some cases. Here, in the case of the wireless type, a wireless local area network (WLAN)-based communication scheme such as Wi-Fi may be mainly used. Alternatively, in the case of the wireless type, cellular communication may be used, for example, LTE-based communication scheme or 5G-based communication scheme. In particular, the scalp measuring device 1000 according to an embodiment may transmit and receive data to and from the electronic device 2000 through a Wi-Fi Direct-based communication scheme. At this time, the scalp measuring device

1000 may transmit and receive data to and from the server 3000 by using the electronic device 2000 as a medium. However, the wireless communication protocol is not limited to the above-described example, and any suitable wireless type communication scheme may be used. In addition, in the case of the wired type, a local area network (LAN) or universal serial bus (USB) communication is a representative example, and other schemes are possible.

The memory 1300 may store various information. The memory 1300 may temporarily or semi-permanently store various data. Examples of the memory 1300 may include a hard disk (HDD), a solid state drive (SSD), a flash memory, a read-only memory (ROM), a random access memory (RAM), and the like. The memory 1300 may be provided in a form embedded in the scalp measuring device 1000 or provided in a form detachable. The memory 1300 may store various data necessary for the operation of the scalp measuring device 1000, including an operating system (OS) for driving the scalp measuring device 1000 or a program for operating each component of the scalp measuring device 1000. For example, various data related to a scalp image and information related to a target image may be stored in the memory 1300.

The scalp measuring device 1000 according to an embodiment of the present disclosure may include an input unit 1400. The scalp measuring device 1000 may obtain a user input through the input unit 1400. For example, the scalp measuring device 1000 may obtain a user input requesting a photographing of a scalp image through the input unit 1400. In addition, the scalp measuring device 1000 may obtain a user input requesting a sensing data acquisition through the input unit 1400. In addition, the scalp measuring device 1000 may obtain a user input requesting a photographing mode of the camera 1110 or an activation of the sensor module 1100 through the input unit 1400. The input unit 1400 may be provided in any of various forms, such as an input button, a switch, a mouse, a keyboard, a touch pad, and the like.

According to an embodiment, the input unit 1400 may be configured as a plurality of input modules. For example, the input unit 1400 of the scalp measuring device 1000 may include a first input module for obtaining a first input and a second input module for obtaining a second input different from the first input. Here, the first input module and the second input module may be provided in a form appropriate for obtaining a user input, respectively.

The scalp measuring device 1000 according to an embodiment of the present disclosure may include an output unit 1500. The scalp measuring device 1000 may output information related to a scalp of a user through the output unit 1500.

For example, the output unit 1500 may output a scalp image obtained by the scalp measuring device 1000 to the user. For example, the output unit 1500 may output a scalp image photographed by the camera 1110 of the scalp measuring device 1000 to the user. Alternatively, the output unit 1500 may output a target image selected from among a plurality of scalp images to the user. Through this, the user may check whether the selected target image is appropriate. In addition, the user may correct the selected target image or indicate a replacement to another scalp image through the above-described input unit 1400.

As another example, the output unit 1500 may output hair loss diagnosis assistance information and/or hair loss progression indicator information obtained from the server 3000. For example, the server 3000 may calculate the hair loss diagnosis assistance information of the user based on the target image and/or the sensing data, as described below. Here, the scalp measuring device 1000 may receive the hair loss diagnosis assistance information from the server 3000 and output the received hair loss diagnosis assistance information through the output unit 1500.

The output unit 1500 may be provided in any of various forms, such as a display panel, a speaker, and the like, capable of outputting information. In addition, the scalp measuring device 1000 may provide a user interface for obtaining a user input and outputting information corresponding to the obtained user input.

Although FIG. 31 illustrates that the scalp measuring device 1000 according to an embodiment of the present disclosure includes the output unit 1500, this is merely an example, and according to an embodiment, the scalp measuring device 1000 having the output unit 1500 omitted may be provided.

The controller 1600 may control the overall operation of the scalp measuring device 1000. For example, the controller 1600 may control the overall operation of the scalp measuring device 1000, such as an operation of selecting a target image to be described below or an operation of correcting information obtained from the target image. Specifically, the controller 1600 may load and execute a program for the overall operation of the scalp measuring device 1000 from the memory 1300. The controller 1600 may be implemented as an application processor (AP), a central processing unit (CPU), or a device similar to the same according to hardware, software, or a combination thereof. Here, the hardware may be provided in the form of an electronic circuit that processes an electrical signal to perform a control function, and the software may be provided in the form of a program or code that drives a hardware circuit.

Meanwhile, the scalp measuring device 1000 according to an embodiment may communicate with the server 3000 directly. However, according to an embodiment, there may be a situation in which the scalp measuring device 1000 cannot communicate with the server 3000 directly. In this case, the scalp measuring device 1000 may transmit and receive a plurality of scalp images and/or sensing data to and from the server 3000 via the electronic device 2000.

As described above, according to an embodiment of the present disclosure, the electronic device 2000 may serve as a medium of the scalp measuring device 1000 and the server 3000. For example, the electronic device 2000 may receive a plurality of scalp images from the scalp measuring device 1000. In addition, the electronic device 2000 may receive sensing data from the scalp measuring device 1000. The electronic device 2000 may transmit the plurality of scalp images and/or sensing data received from the scalp measuring device 1000 to the server 3000. In addition, the electronic device 2000 may receive hair loss diagnosis assistance information or a hair loss progression indicator from the server 3000. According to an additional embodiment, the electronic device 2000 may output the plurality of scalp images received from the scalp measuring device 1000. Alternatively, the electronic device 2000 may output the hair loss diagnosis assistance information and/or the hair loss progression indicator received from the server 3000.

In this case, as described above, the electronic device 2000 may perform communication with the scalp measuring device 1000 in a Wi-Fi Direct scheme. On the other hand, as described below, the electronic device 2000 may perform communication with the server 3000 in any suitable communication scheme, for example, a WLAN-based communication scheme (e.g., Wi-Fi communication) or a cellular communication scheme (e.g., LTE, 5G communication).

Meanwhile, according to an embodiment of the present disclosure, the electronic device 2000 may perform a partial function of the scalp measuring device 1000 and/or a partial function of the server 3000. For example, the electronic device 2000 may perform an operation of selecting a target image from among the plurality of scalp images instead of the scalp measuring device 1000. In addition, the electronic device 2000 may perform at least a part of an operation of calculating hair loss diagnosis assistance information of a user instead of the server 3000. For example, the electronic device 2000 may receive a parameter set of a neural network model (e.g., a right version of the neural network model) used to calculate hair loss diagnosis assistance information from the server 3000 and may perform at least a part of an operation of directly calculating hair loss diagnosis assistance information from data of the scalp measuring device.

Figure 33:
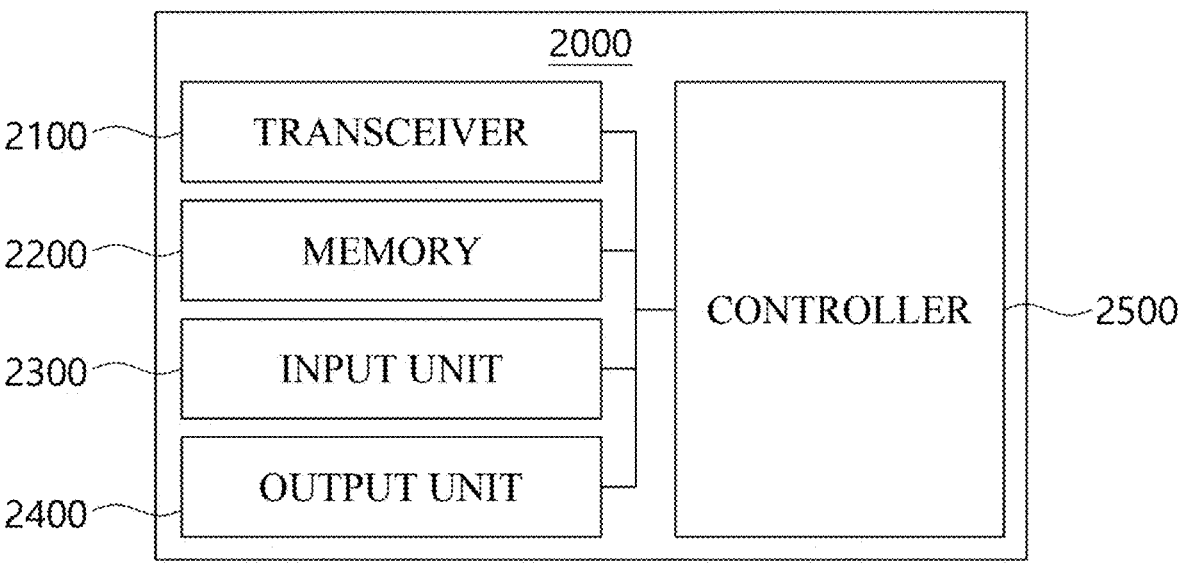
FIG. 33 is a schematic block diagram of an electronic device 2000 according to an embodiment of the present application.

Hereinafter, a configuration of the electronic device 2000 according to an embodiment of the present disclosure will be described with reference to FIG. 33. The electronic device 2000 according to an embodiment of the present disclosure may include a transceiver 2100, a memory 2200, an input unit 2300, an output unit 2400, and a controller 2500.

The transceiver 2100 may communicate with any external device including the scalp measuring device 1000 and the server 3000. For example, the electronic device 2000 may receive various data including a scalp image, temperature data related to the scalp, humidity data, odor data, and the like from the scalp measuring device 1000 through the transceiver 2100. In addition, the electronic device 2000 may transmit the selected target image to the server 3000 through the transceiver 2100. In addition, the electronic device 2000 may receive hair loss diagnosis assistance information and/or hair loss progression indicators from the server 3000 through the transceiver 2100. In addition, the electronic device 2000 may access a network through the transceiver 2100 to upload various data related to the scalp image.

The transceiver 2100 may include a wired type and a wireless type. Since the wired type and the wireless type have advantages and disadvantages of each other, the wired type and the wireless type may be simultaneously provided in the electronic device 2000 in some cases.

Here, in the case of the wireless type, a wireless local area network (WLAN)-based communication scheme such as Wi-Fi may be mainly used. Alternatively, in the case of the wireless type, cellular communication (e.g., LTE, 5G-based communication scheme) may be used. However, since the wireless communication protocol is not limited to the above-described example, it is possible to use any suitable wireless type communication scheme.

In addition, in the case of the wired type, local area network (LAN) or universal serial bus (USB) communication is a representative example and other schemes are possible.

Meanwhile, the electronic device 2000 may transmit and receive data to and from the scalp measuring device 1000 and the server 3000 through the transceiver 2100 in various ways. For example, the electronic device 2000 may transmit and receive data to and from the scalp measuring device 1000 and the server 3000 using a common transceiver. As another example, the electronic device 2000 may be implemented to transmit and receive data to and from the scalp measuring device 1000 through the first transceiver 2110, and to transmit and receive data to and from the server 3000 through the second transceiver 2120. In other words, the electronic device 2000 may be implemented to include a separate transceiver capable of transmitting and receiving data to and from the scalp measuring device 1000 and the server 3000, respectively.

In particular, the electronic device 2000 according to an embodiment may perform communication with the scalp measuring device 1000 using a Wi-Fi communication scheme. Specifically, the electronic device 2000 may transmit and receive data to and from the scalp measuring device 1000 through a Wi-Fi Direct-based communication scheme. In this case, the electronic device 2000 may transmit data received from the scalp measuring device 1000 to the server 3000 as a medium of the scalp measuring device 1000 and the server 3000.

On the other hand, the electronic device 2000 may perform communication with the server 3000 using various mobile communication schemes such as a 3rd Generation (3G), a Long Term Evolution (LTE), and a 5G. However, according to an embodiment, the electronic device 2000 may perform communication with the server 3000 using a Wi-Fi communication scheme or a wired communication scheme.

The memory 2200 may store various kinds of information. The memory 2200 may temporarily or semi-permanently store various kinds of data. Examples of the memory 2200 may include a hard disk drive (HDD), a solid state drive (SSD), a flash memory, a read-only memory (ROM), a random access memory (RAM), and the like. The memory 2200 may be provided in a form built in the electronic device 2000 or in a form detachable. The memory 2200 may store various kinds of data necessary for an operation of the electronic device 2000, including an operating system (OS) for driving the electronic device 2000 or a program for operating each component of the electronic device 2000. For example, various kinds of data related to a scalp image and information related to a target image may be stored in the electronic device 2000.

The electronic device 2000 according to an embodiment of the present disclosure may include an input unit 2300. The electronic device 2000 may obtain a user input through the input unit 2300. For example, the electronic device 2000 may obtain a user input requesting initiation of an operation of selecting a target image through the input unit 2300. In addition, the electronic device 2000 may obtain a user input requesting correction or processing of a selected target image through the input unit 2300. In addition, the electronic device 2000 may obtain a user input manipulating a user interface providing hair loss diagnosis assistance information through the input unit 2300. Meanwhile, the input unit 2300 may be provided in any of various forms such as an input button, a switch, a mouse, a keyboard, a touch pad, and the like.

According to an embodiment, the input unit 2300 may include a plurality of input modules. For example, the input unit 2300 of the electronic device 2000 may include a first input module for obtaining a first input and a second input module for obtaining a second input different from the first input. Here, the first input module and the second input module may be provided in a form suitable for obtaining a user input, respectively.

The electronic device 2000 according to an embodiment of the present disclosure may include an output unit 2400. The electronic device 2000 according to an embodiment may output various kinds of information related to a scalp to a user through the output unit 2400. For example, the output unit 2400 may output a selected target image to the user. Through this, the user may check whether the selected target image is appropriate. In addition, the user may correct the selected target image or indicate a replacement to another scalp image through the input unit 2300. As another example, the output unit 2400 may output hair loss diagnosis assistance information and/or hair loss progression indicator information obtained from the server 3000. For example, the server 3000 may calculate hair loss diagnosis assistance information based on the target image and/or sensing data, as described below. Here, the electronic device 2000 may receive hair loss diagnosis assistance information from the server 3000 and output hair loss diagnosis assistance information through the output unit 2400. The output unit 2400 may be provided in various forms such as a display panel, a speaker, and the like.

According to an embodiment, the output unit 2400 may include a plurality of output modules. For example, the electronic device 1000 may include a first output module (e.g., a display panel) for outputting first type information and a second output module (e.g., a speaker) for outputting second type information different from the first type information. Here, the first output module and the second output module may be provided in a form suitable for obtaining a user input, respectively. The electronic device 2000 may provide a user interface for obtaining a user input and outputting information corresponding to the obtained user input.

The controller 2500 may control the overall operation of the electronic device 2000. For example, the controller 2500 may control the overall operation of the electronic device 2000, such as an operation of selecting a target image, an operation of correcting information obtained from the target image, or an operation of outputting hair loss diagnosis assistance information, which will be described later. Specifically, the controller 2500 may load and execute a program for an operation of the electronic device 2000 from the memory 2200.

The controller 2500 may be implemented as an application processor (AP), a central processing unit (CPU), or a device similar to the same according to hardware, software, or a combination thereof. Here, the hardware may be provided in the form of an electronic circuit for processing an electrical signal to perform a control function, and the software may be provided in the form of a program or code for driving a hardware circuit.

According to an embodiment of the present application, the server 3000 may obtain a scalp image (e.g., a target image) and/or sensing data. The server 3000 may calculate hair loss diagnosis assistance information based on the scalp image and/or the sensing data. Here, the server 3000 may use a pre-trained neural network model in the process of calculating the hair loss diagnosis assistance information. For example, the server 3000 may use a neural network model trained to receive the target image and output pore region information, and may calculate hair loss diagnosis assistance information based on the pore region information. In addition, the server 3000 may transmit the calculated hair loss diagnosis assistance information to the scalp measuring device 1000 and/or the electronic device 2000. Detailed operations of the server 3000 will be described in detail with reference to FIGS. 48 to 61.

Hereinafter, some operations performed by an embodiment of the scalp image analysis system will be described in more detail.

Hereinafter, an operation of selecting a target image according to an embodiment of the present application will be described in detail with reference to FIGS. 34 to 43. Here, the target image means at least one scalp image used to analyze a scalp state of a user. That is, the target image may mean a scalp image transmitted to the server 3000 and used to analyze the scalp state of the user. Meanwhile, in order to accurately analyze the scalp state, the target image needs to be selected optimally. Therefore, the target image may be selected as an optimal (e.g., clear or focus clear) scalp image among a plurality of scalp images obtained through the camera 1110 of the scalp measuring device 1000.

According to an embodiment of the present application, the operation of selecting the target image may be performed by at least one of the scalp measuring device 1000 and the electronic device 2000.

For example, the operation of selecting the target image may be performed by the scalp measuring device 1000 of the present application. For example, the scalp measuring device 1000 may select the target image from among the plurality of scalp images captured through the camera 1110.

As another example, when the scalp measuring device 1000 and the electronic device 2000 are interlocked with each other, the plurality of scalp images captured from the camera 1110 of the scalp measuring device 1000 may be transmitted to the electronic device 2000. For example, the plurality of scalp images captured from the camera 1110 of the scalp measuring device 1000 may be transmitted to the electronic device 2000 in real time. Alternatively, the plurality of scalp images captured from the camera 1110 of the scalp measuring device 1000 may be transmitted to the electronic device 2000 after the capturing of the camera 1100 is completed. In this case, the electronic device 2000 may select the target image from among the obtained plurality of scalp images.

Meanwhile, the plurality of scalp images captured through the camera 1110 may be transmitted to the electronic device 2000 in a video format as well as in an image format. In this case, the electronic device 2000 may select the target image from data in a video format.

Figure 34:
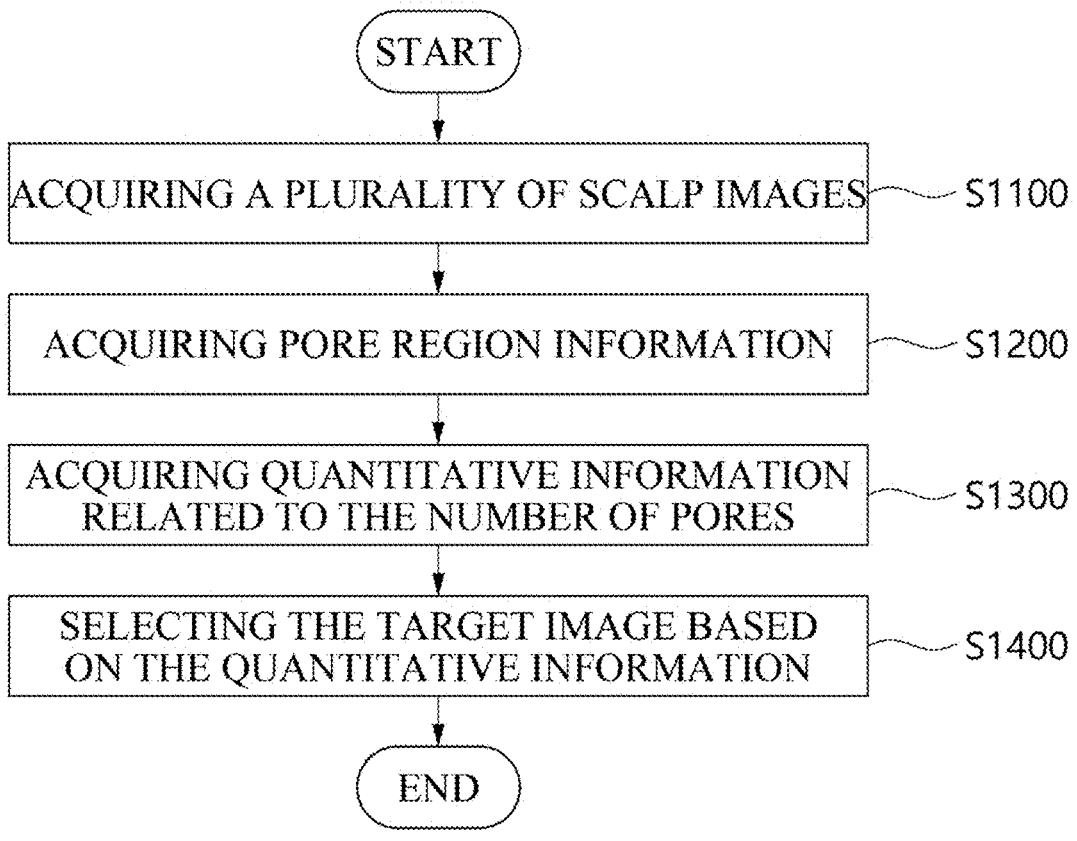
FIG. 34 is a flowchart illustrating a method of selecting a target image according to an embodiment of the present application.

FIG. 34 is a flowchart illustrating a method of selecting a target image according to an embodiment of the present application.

The plurality of scalp images obtained by the scalp measuring device 1000 may include scalp images relatively suitable for calculating hair loss diagnosis assistance information, and may include scalp images relatively inappropriate for calculating hair loss diagnosis assistance information. For example, when a scalp image is captured using a camera, since the camera is closely attached to a very close distance of the scalp, an image that is not clear, for example, an image having a blurred focus, is highly likely to be obtained.

Accordingly, the scalp measuring device 1000 or the electronic device 2000 according to an embodiment of the present application may perform an operation of selecting a clear high-quality scalp image among the plurality of scalp images as the target image. Hereinafter, an operation of selecting a target image based on the scalp measuring device 1000 will be described, but at least some of the operations of selecting the target image by the electronic device 2000 may be performed according to an embodiment.

Various information (e.g., keratin information, scalp sensitivity, pore region information, hair information, and the like) that may be obtained from the scalp image may be used as a reference for selecting the target image of the scalp measuring device 1000. For example, the scalp measuring device 1000 may use quantitative information of the pore region to select the target image. Hereinafter, an embodiment of using quantitative information of the pore region to select the target image will be described. However, this is merely an example, and various information that may be obtained from the scalp image may be used to select a clear-quality scalp image.

Referring to FIGS. 31 and 34, a method of selecting a target image according to an embodiment of the present application may include acquiring a plurality of scalp images (S1100), acquiring pore region information (S1200), acquiring quantitative information related to the number of pores (S1300), and selecting the target image based on the quantitative information (S1400).

In the acquiring the plurality of scalp images (S1100), the scalp measuring device 1000 may acquire the plurality of scalp images captured through the camera 1110. Here, the plurality of scalp images may mean to include all of the plurality of scalp images acquired by the camera 1110 to continuously photograph and and/or the manually captured scalp image acquired in response to the user's photographing instruction input.

Meanwhile, sensing data including temperature data, humidity data, odor data, etc of the scalp acquired from the environmental sensor 1102 of the scalp measuring device 1000 may be acquired together when the scalp image is acquired. The sensing data may be considered for calculating hair loss diagnosis assistance information to be described below.

According to an additional embodiment, the gyro sensor data acquired from the gyro sensor 1104 may be acquired together when the scalp image is acquired. The gyro sensor data may be used to identify which scalp area of the user is measured with respect to the scalp image in relation to calculating the hair loss progression indicator to be described below. In this regard, the description will be given below with reference to FIGS. 59 to 61.

Hereinafter, a scalp image acquisition operation according to an embodiment of the present application will be described in detail with reference to FIGS. 31, 35 to 37. Here, the scalp image acquisition operation to be described with reference to FIGS. 35 to 37 may be controlled by the controller 1600 of the scalp measuring device 1000 according to an embodiment of the present application.

Figure 35:
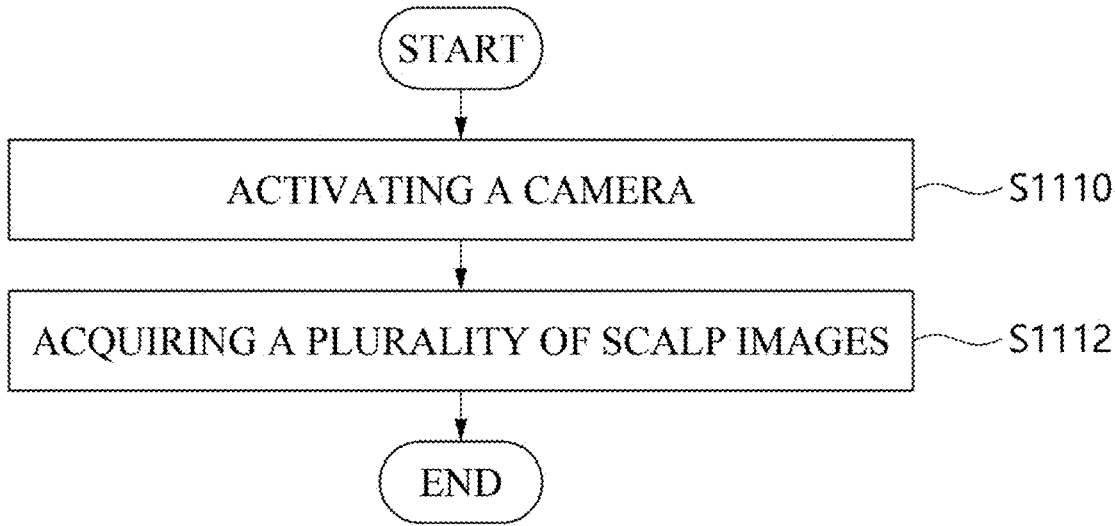
FIGS. 35 and 36 are flowcharts illustrating a method of acquiring a scalp image according to an embodiment of the present application.
Figure 36:
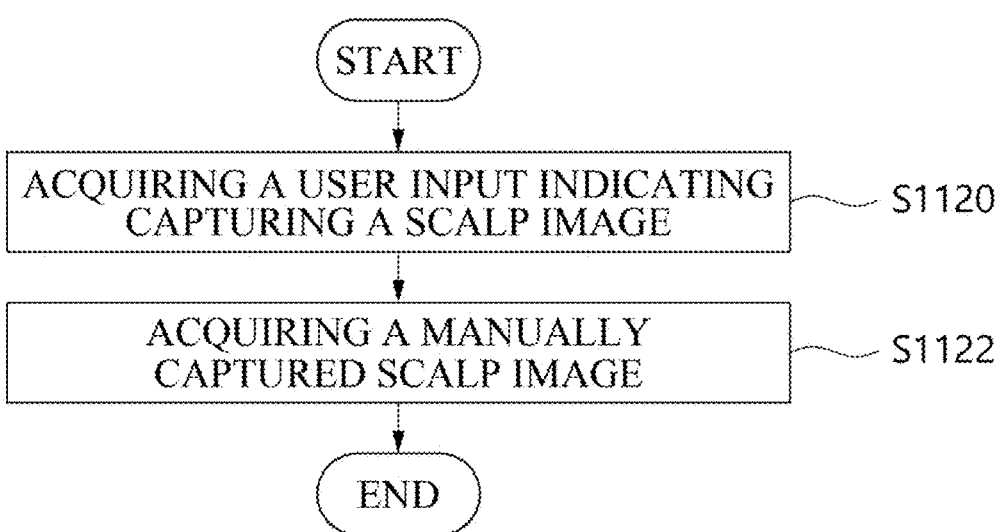

FIGS. 35 and 36 are flowcharts illustrating embodiments of the present application in which the scalp measuring device acquires a scalp image.

Referring to FIG. 35, a method for acquiring a scalp image according to an embodiment of the present application may include activating a camera (S1110), and acquiring a plurality of scalp images (S1112).

In the activating camera (S1110), the scalp measuring device 1000 may activate the camera 1100 for photographing a scalp image. For example, as the scalp measuring device 1000 is powered on, the camera 1110 may be activated. That is, when the scalp measuring device 1000 is powered on, the controller 1600 may be configured to activate the camera 1110. Meanwhile, when the camera 1110 is activated, a temperature sensor, a moisture sensor, and/or a TVOC sensor included in the sensor module 1100 may also be activated together. As another example, the camera 1110 may be activated based on a user's input requesting activation of the camera 1110. In this case, as described below, as the camera 1110 is activated, the photographing mode may be automatically executed, and the camera 1110 may measure a scalp image. Meanwhile, according to an embodiment, an input unit for turning on the scalp measuring device 1000 and an input unit for activating the camera 1110 may be separately configured from each other.

In the acquiring a plurality of scalp images (S1112), the scalp measuring device 1000 may acquire a plurality of scalp images through the camera 1110. For example, as described above, when the camera 1110 is activated, the photographing mode may be automatically executed so that the camera 1110 performs photographing. In this case, the user may approach or make the camera 1110 of the scalp measuring device 1000 into contact with the scalp. The scalp measuring device 1000 may acquire a plurality of scalp images photographing the scalp of the user through the camera 1110. As another example, after the camera 1110 is activated, the photographing mode of the camera 1110 may be executed based on a user's input triggering execution of the photographing mode. In this case, the scalp measuring device 1000 may acquire a plurality of scalp images capturing the scalp of the user through the camera 1110 under the capturing mode executed in response to the user input.

Referring to FIG. 36, a scalp image acquisition method according to another embodiment of the present disclosure may include acquiring a user input indicating capturing a scalp image (step S1102) and acquiring a manually captured scalp image (step S1122).

In acquiring a user input indicating capturing a scalp image (step S1102), the scalp measuring device 1000 may receive a user input through the input unit 1400 described above. First, the user may approach or contact the scalp measuring device 1000 with a scalp region desired by the user. In this case, the user may indicate capturing a scalp region desired through the input unit 1400.

In acquiring the manually captured scalp image (step S1122), the scalp measuring device 1000 may acquire a manually captured scalp image related to a scalp region desired by the user through the camera 1110. Here, the manually captured scalp image may mean a scalp image captured based on a user input triggering capturing a scalp image acquired through the input unit 1400. For example, the scalp image described in FIG. 35 may mean a scalp image continuously captured under the capturing mode of the camera 1110, but the manually captured scalp image described in FIG. 36 may be distinguished from a scalp image captured in response to a user input triggering capturing a scalp image.

Meanwhile, in acquiring the manually captured scalp image (step S1122), one or a predetermined number of scalp images may be acquired in response to the user input. To this end, the number of scalp images to be captured in response to the user input may be preset.

Meanwhile, according to an embodiment of the present disclosure, the scalp measuring device 1000 and the electronic device 2000 may be interlocked with each other. For example, the scalp measuring device 1000 and the electronic device 2000 may perform communication with each other using Wi-Fi communication. Specifically, the scalp measuring device 1000 and the electronic device 2000 may perform communication with each other using Wi-Fi Direct communication.

The scalp measuring device 1000 may transmit the acquired plurality of scalp images or the manually captured scalp image to the electronic device 2000. In addition, the electronic device 2000 may receive the plurality of scalp images or the manually captured scalp image from the scalp measuring device 1000. However, the aforementioned communication scheme of the scalp measuring device 1000 and the electronic device 2000 is merely an example, and it is also understood that data transmission and reception between the scalp measuring device 1000 and the electronic device 2000 may be implemented using any communication scheme.

Meanwhile, although not shown in FIG. 34, the method of selecting the target image according to an embodiment of the present disclosure may further include pre-processing the acquired scalp image. In other words, the plurality of scalp images described in step S1100 of FIG. 34 may be interpreted as meanings encompassing the preprocessed scalp image.

For example, the scalp measuring device 1000 according to an embodiment may perform an operation of lowering the resolution of the scalp image. For example, the resolution of the original data of the scalp image acquired from the camera 1110 may be relatively high. However, selecting the target image using the scalp image having a high resolution may be relatively disadvantageous in terms of data processing speed. In particular, in the case where the scalp image is input to the neural network model at the resolution as it is the original in the step S1200 of obtaining the pore region information to be described below, the processing speed of the neural network model may be relatively slow.

Accordingly, the scalp measuring device 1000 according to an embodiment of the present disclosure may perform an operation of lowering the resolution of the scalp image. For example, the scalp measuring device 1000 may perform an operation of converting the high-resolution scalp image of the original to a low-resolution. That is, the scalp measuring device 1000 may perform an operation of reducing the size of the scalp image. As another example, the scalp measuring device 1000 according to an embodiment may perform an operation of modifying the size or the ratio of the scalp image. For example, the scalp measuring device 1000 may utilize any suitable crop technique to cut the scalp image. In other words, the scalp measuring device 1000 according to an embodiment of the present disclosure may perform the above-described operation of lowering the resolution and the operation of modifying the size of the scalp image together. Accordingly, the data processing speed of the scalp measuring device 1000 may be improved, and thus, scalp state analysis may be rapidly and effectively performed.

However, there may be a case where the scalp state analysis should be finely performed. In this case, in order to analyze the scalp image more precisely, the operation of pre-processing the scalp image (e.g., the operation of lowering the resolution of the scalp image or modifying the size of the scalp image) is omitted, and the analysis may be performed using the scalp image of the original. Alternatively, as a method of preprocessing the scalp image for more precisely analyzing the scalp image, any suitable image processing method may be implemented. For example, any image processing technique for removing noise that may be present in the scalp image may be performed.

In the step S1200 of obtaining the pore region information, the scalp measuring device 1000 may obtain pore region information from each of the plurality of scalp images. Here, the pore region information may mean any information related to the pore region including position information and/or quantitative information of the pore region included in each of the scalp images.

For example, the pore region information may be obtained using the trained neural network model. For example, the pore region information may be obtained using the trained neural network model to receive the scalp image and output the pore region information. As another example, the pore region information may be obtained using any image analysis algorithm and/or software.

Figure 37:
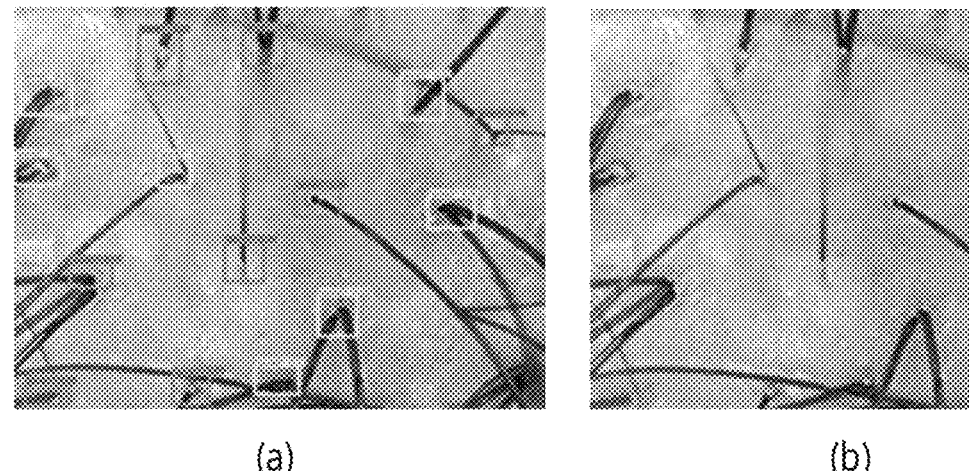
FIG. 37 is a diagram illustrating exemplary pore region information acquired through a trained neural network model according to an embodiment of the present application.

FIG. 37 is an exemplary diagram illustrating pore region information obtained through the trained neural network model according to an embodiment of the present disclosure.

The pore region information may include various pieces of information about the pore region obtained from the scalp image. The pore region information may include information about a plurality of regions included in the scalp image. According to an embodiment, the pore region information may include first region information indicating a first region (e.g., a pore region) obtained from the scalp image. In addition, the pore region information may include second region information indicating a second region (e.g., a pore region and a hair region adjacent thereto) of a shape different from the first region obtained from the scalp image.

According to an embodiment of the present disclosure, information of a first type (e.g., a point) may be overlaid on the first region (e.g., the pore region) of the scalp image based on the first region information. In addition, information of a second type (e.g., a bounding box) may be overlaid on the second region (e.g., the pore region and the hair region adjacent thereto) of the scalp image based on the second region information. Accordingly, the first region information and the second region information may be more easily distinguished. However, the above description is merely exemplary, and an output result may be configured as an arbitrary shape for distinguishing the first region information and the second region information.

The pore region information may be obtained for one or more scalp images, respectively. The pore region information may include various pieces of information related to the pore region obtained from the scalp image.

For example, the pore region information may include location information (e.g., a point in FIG. 37(b)) related to each pore region included in the scalp image. Specifically, the pore region information may include location information of the first pore region included in the first scalp image and location information of the second pore region included in the first scalp image.

For example, the pore region information may include information related to the total number of pore regions included in the scalp image. Specifically, when N pore regions are obtained in the scalp image, the pore region information may include quantitative information indicating that N pore regions are included in the scalp image.

For example, the pore region information may include information related to the number of hairs per pore region. More specifically, when N hairs are extracted in a specific pore region, information indicating that N hairs are included in the pore region (e.g., a red box in FIG. 37(a)) may be included in the pore region information.

However, the pore region information shown in FIG. 37 is merely an exemplary drawing for convenience of description, and it is to be understood that the pore region information may include information indicating that the number of hairs per pore region is N and/or information indicating the total number of hairs.

Meanwhile, the pore region information output through the trained neural network model may be output in the form of probability information. For example, the pore region information output through the trained neural network may be provided in the form of a probability map including a probability value for the pore region and/or a probability value for the number of hairs per pore region. The probability information may be used to correct initial pore region information as described below with reference to FIGS. 54 to 58.

Figure 38:
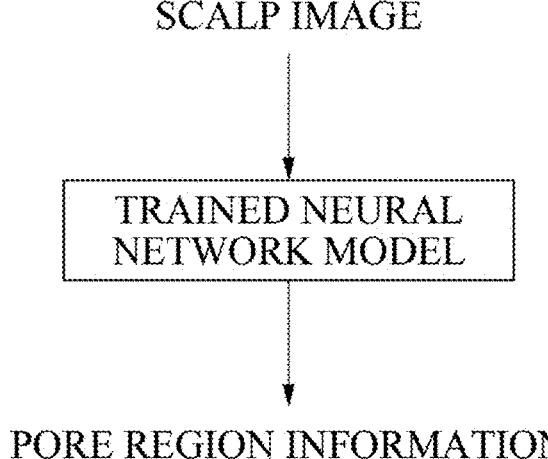
FIG. 38 is a schematic diagram illustrating a deploying operation of a trained neural network model according to an embodiment of the present application.

According to an embodiment of the present disclosure, the above-described pore region information may be obtained through the trained artificial neural network model. FIG. 38 is a schematic diagram illustrating a deploying operation of the trained neural network model according to an embodiment of the present disclosure.

The trained neural network model may be configured to output pore region information from the scalp image. More specifically, the neural network model is trained to receive a scalp image through an input layer and output pore region information through an output layer. At this time, pore region information about the scalp image may be acquired using the trained neural network.

Hereinafter, a learning method and a deploying method of a neural network model used to acquire pore region information according to an embodiment of the present application will be described in more detail with reference to FIGS. 31 and 39 to 43.

FIG. 39 is a flowchart illustrating a process for acquiring pore region information according to an embodiment of the present application. The process for acquiring pore region information according to an embodiment of the present application may include a learning process P1000 of the neural network model and a deploying process P2000 for acquiring pore region information using the trained artificial neural network model.

At this time, the learning process P1000 may be performed by the server 3000 according to an embodiment of the present application. However, according to an embodiment, the learning process P1000 may be performed by the scalp measuring device 1000 or any external device including the electronic device 2000.

In addition, the deploying process P2000 may be performed by the scalp measuring device 1000 or the electronic device 2000 according to an embodiment of the present application. At this time, a parameter of the neural network model acquired by the learning process P1000 may be transmitted from the server 3000 to the scalp measuring device 1000 or the electronic device 2000. At this time, the scalp measuring device 1000 or the electronic device 2000 may acquire pore region information based on the parameter of the neural network model acquired by the learning process P1000 and the scalp image acquired from the scalp measuring device 1000.

The learning process P1000 according to an embodiment of the present application may include a process P1100 for acquiring a learning data set, a process P1200 for training the neural network model, a process P1300 for verifying the neural network model, and a process P1400 for acquiring a parameter of the neural network model.

Figure 40:
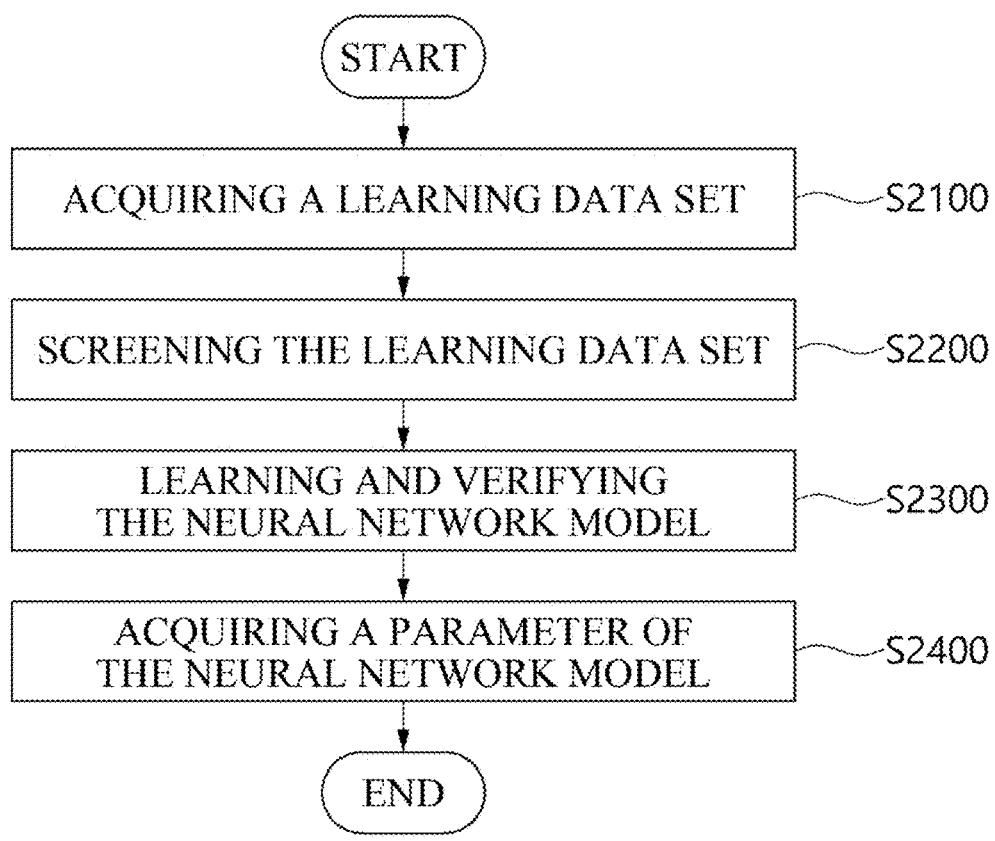
FIG. 40 is a flowchart of a method of learning a neural network model according to an embodiment of the present application.

Hereinafter, a learning method of a neural network model according to an embodiment of the present application will be described in more detail with reference to FIG. 40. FIG. 40 is a flowchart illustrating a learning method of a neural network model according to an embodiment of the present application.

The learning method of the neural network model according to an embodiment of the present application may include acquiring a learning data set (S2100), screening the learning data set (S2200), learning and verifying the neural network model (S2300), and acquiring a parameter of the neural network model (S2400).

In the acquiring step (S2100) of the learning data set, the learning data sets may be acquired from the scalp measuring device 1000 or any external devices. The learning data set may be a basis for training the neural network model.

Figure 41:
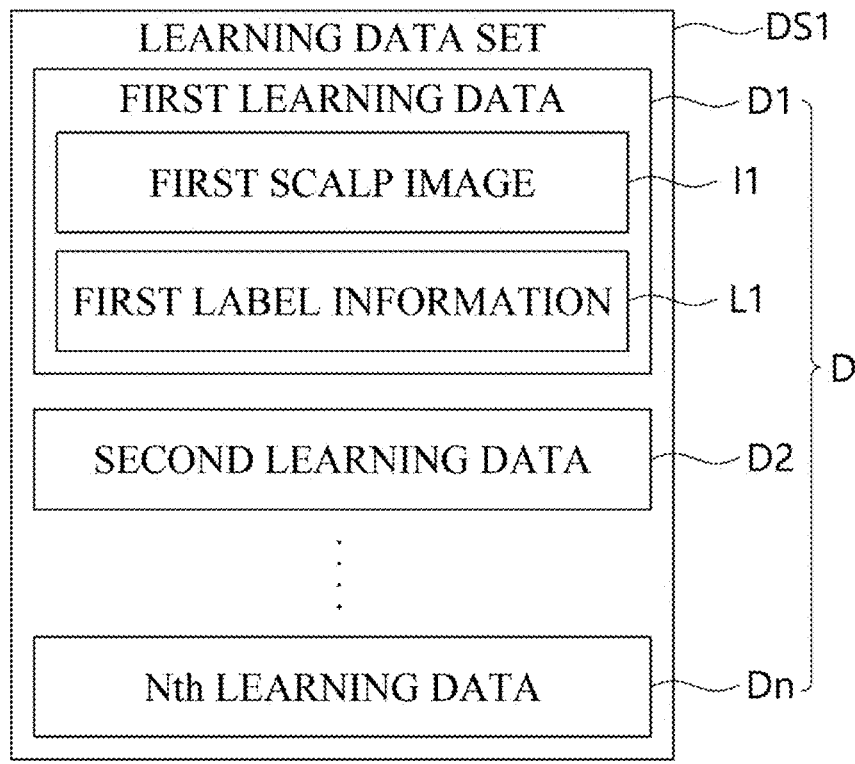
FIG. 41 is a schematic structure diagram of a learning data set according to an embodiment of the present application.

FIG. 41 is an exemplary structure diagram of a learning data set according to an embodiment of the present application. The learning data set DS1 may include one or more learning data D. In other words, the learning data set DS1 may include first learning data D1, second learning data D2, to nth learning data Dn.

At this time, each of the one or more learning data included in the learning data set DS1 may include a scalp image and label information. For example, the first learning data D1 included in the learning data set DS1 may include a first scalp image I1 and first label information L1.

The label information included in the learning data set DS1 may mean encompassing any type of information given to the scalp image of the learning data in order to train the neural network model outputting the pore region information. For example, the label information may include information related to the pore region included in the scalp image.

For example, the label information included in the learning data set DS1 may include information indicating that a portion of the area included in the scalp image corresponds to the pore region. For example, when the first area of the scalp image corresponds to the pore region, the label information may include first information indicating that the first area is the pore region.

For example, the label information included in the learning data set DS1 may include information indicating that a portion of the area included in the scalp image corresponds to the hair region including the pore region. For example, when the second area of the scalp image corresponds to the hair region including the pore region, the label information may include second information indicating that the second area is the hair region including the pore region.

For another example, the label information included in the learning data set DS1 may include information indicating the number of hairs per each pore region included in the scalp image. For example, when the first pore region included in the scalp image has 1 hair, the label information may include information indicating that the first pore region has 1 hair. For example, when the second pore region included in the scalp image has 2 hairs, the label information may include information indicating that the second pore region has 2 hairs. For example, when the third pore region included in the scalp image has 3 hairs, the label information may include information indicating that the third pore region has 3 hairs.

In this case, the label information may be manually labeled with respect to each of the scalp images I1 to In of the learning data set DS1. Alternatively, the label information may be automatically labeled with respect to each of the scalp images I1 to In of the learning data set DS1 using any suitable image analysis technique. The scalp image and the label information included in the learning data may be used to train a neural network model and verify the neural network model in relation to the learning method of the neural network model according to an embodiment of the present application.

In the step S2200 of screening the learning data set, an operation of screening the learning data set obtained in the step S2100 of obtaining the learning data set or selecting only some learning data among the learning data included in the learning data set may be performed. For example, some learning data among the learning data set may not be suitable for learning the neural network model. For example, some learning data may include serious noise or artifacts, and such learning data may not be suitable for training the neural network model. Accordingly, in the step S2200 of screening the learning data set, only learning data suitable for training the neural network model may be selected.

Figure 42:
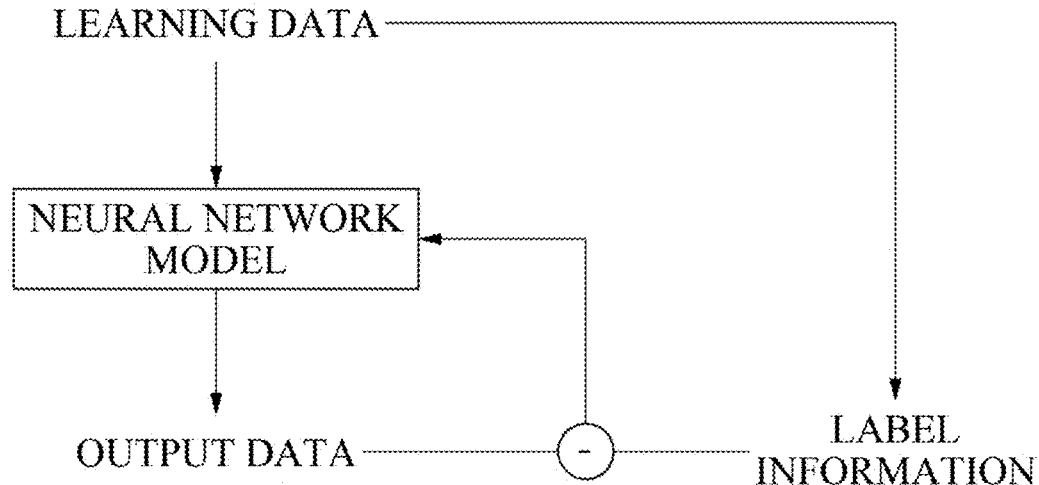
FIG. 42 is a schematic diagram illustrating a method of learning a neural network model according to an embodiment of the present application.

In the step S2300 of learning and verifying the neural network model, the neural network model outputting the pore region information may be trained. Hereinafter, a method of learning a neural network model according to an embodiment of the present application will be described with reference to FIGS. 41 and 42. FIG. 42 is a schematic diagram illustrating a method of learning a neural network model according to an embodiment of the present application.

The neural network model may include an input layer for receiving learning data, an output layer for outputting output data that is a result, and a hidden layer including one or more nodes. In this case, the neural network model may be implemented to receive learning data D included in the acquired learning data set (DS1) through the input layer and to output output data through the output layer.

In addition, the neural network model may be configured to adjust a parameter of at least one node included in the neural network model based on the output data and label information L of the learning data D included in the learning data set (DS1). Specifically, a weight or parameter of at least one node included in the hidden layer of the neural network model may be adjusted based on a difference between the label information L included in the learning data D and the output data output through the output layer of the neural network model, thereby learning the neural network model.

For example, the neural network model may be configured to acquire a scalp image of learning data (e.g., learning data of each of D1 and D2 to Dn of FIG. 41) as an input and to output output data through the output layer. In this case, the parameter of at least one node included in the neural network model may be updated so that a difference between the label information of the learning data and the output data is reduced. By repeating the above-described learning process, the parameter of the neural network model may be optimized so that the output data is approximated to the label information. In other words, the parameter (or weight) of the node included in the hidden layer may be repeatedly updated so that a difference between the label information included in the learning data and the output data output from the neural network model is minimized.

The neural network model for obtaining the pore region information according to an embodiment of the present application may be a Darknet Yolo, R-CNN, or a Fast R-CNN model. However, this is merely an example, and various image segmentation algorithms including image segmentation using the neural network model may be used.

For example, the image segmentation algorithm may be provided as a machine learning model. A representative example of the machine learning model may include an artificial neural network. Specifically, a representative example of the artificial neural network includes an input layer for receiving data, an output layer for outputting a result, and an artificial neural network having a deep learning series including a hidden layer for processing data between the input layer and the output layer. Specific examples of the artificial neural network include a convolutional neural network, a recurrent neural network, a deep neural network, a generative versarial network, and the like, and the artificial neural network should be interpreted as a generic meaning including all of the artificial neural network described above, various types of artificial neural networks other than the artificial neural networks and artificial neural networks in a combination thereof, and may not necessarily be a deep learning series.

In addition, the machine learning model does not necessarily have the form of the artificial neural network model, and may include a nearest neighboring algorithm (KNN), a random forest, a support vector machine (SVM), a main component analysis method (PCA), and the like. Alternatively, the above-described techniques may include all of the forms ensembled or a combination in various other ways. Meanwhile, it is previously revealed that the artificial neural network may be replaced with another machine learning model unless otherwise mentioned in the embodiments mentioned based on the artificial neural network.

Furthermore, the image segmentation algorithm is not necessarily limited to the machine learning model in the present specification. That is, the image segmentation algorithm may include various determination/determining algorithms rather than the machine learning model. Accordingly, it is necessary to reveal that the image segmentation algorithm in the present specification should be understood as a generic meaning including all types of algorithms performing segmentation using image data.

In the step of verifying the neural network model (S2300), the trained neural network model may be verified as described above. For example, the trained neural network model may be verified based on some learning data (hereinafter, referred to as verification learning data) among one or more learning data D included in the learning data set DS1. Specifically, the trained neural network model may receive a scalp image of the verification learning data and output output data. In this case, the trained neural network model may be verified based on the label information included in the verification learning data and the output data output through the trained neural network model. For example, by comparing the similarity between the label information included in the verification learning data and the output data output through the trained neural network model, it may be verified whether a parameter (or weight) of a node of a hidden layer of the trained neural network model is appropriate.

In the step of obtaining the neural network model (S2400), parameters of a node of the trained neural network model may be obtained. Specifically, as the operation of learning the neural network model and verifying the neural network model based on the learning data D is repeatedly performed as described above, the neural network model including a node having a parameter (or weight) minimizing a difference between the label information included in the learning data D and the output data may be obtained. The obtained node parameter (or weight) and the trained neural network model may be used to calculate pore region information of the scalp image of the deploying process P2000.

Meanwhile, although not shown in FIG. 40, the method of learning the neural network model according to the embodiment of the present application may include a pro-processing step of the learning data set. For example, similar to the pre-processing operation described above with reference to FIG. 34, a pro-processing operation for removing noise included in the scalp image of the learning data set (DS1) or adjusting a resolution of the scalp image may be performed before being input to the neural network model. For example, a pro-processing operation for modifying a size of the scalp image of the learning data set may be performed before being input to the neural network model. The scalp images used in the case of learning the neural network model and the scalp images used in the case of obtaining pore region information using the trained neural network model may be learned and analyzed under the same condition, thereby improving accuracy of the trained neural network model.

Referring back to FIG. 39, the deploying process P2000 according to the embodiment of the present application may include a scalp image obtaining process P2100 and a pore region information obtaining process P2200. The pore region information obtaining process P2200 may be performed by the scalp measuring device 1000 or the electronic device 2000 according to the embodiment of the present application.

Figure 43:
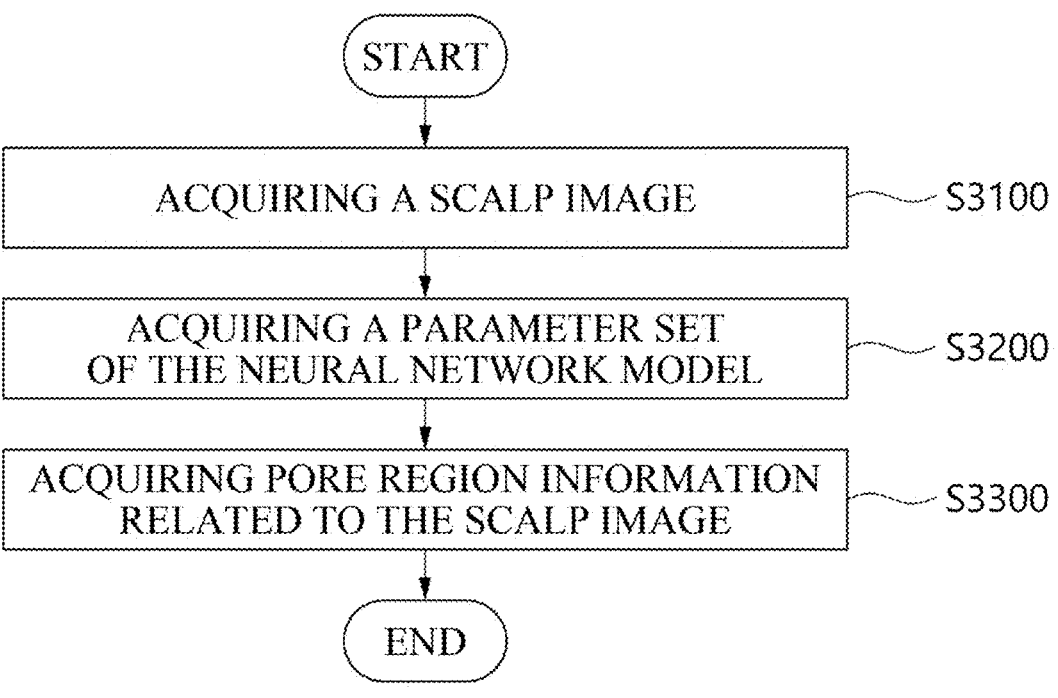
FIG. 43 is a flowchart of a deploying method using a neural network model according to an embodiment of the present application.

Hereinafter, a deploying operation using the neural network model according to the embodiment of the present application will be described with reference to FIG. 43. FIG. 43 is a flowchart of a deploying method using a neural network model according to an embodiment of the present application. The deploying method using the neural network model according to an embodiment of the present application may include acquiring a scalp image in operation S3100, acquiring a parameter set of the neural network model in operation S3200, and acquiring pore region information related to the scalp image based on the parameter set of the neural network model in operation S3300.

In the acquiring operation S3100 of the scalp image, a plurality of scalp images captured from the camera 1110 of the scalp measuring device 1000 may be acquired. Here, the above-described contents of the acquiring operation S3100 of the scalp image may be applied in the same manner in operation S1100 of FIG. 34.

In the acquiring operation S3200 of the parameter set of the neural network model, the parameter sets of the neural network model acquired in operation S2400 of FIG. 40 may be acquired. Specifically, the parameter sets acquired by the learning operation of the neural network model performed by the server 3000 may be transmitted to the scalp measuring device 1000. Accordingly, the scalp measuring device 1000 may acquire the parameter sets of the neural network model.

In the acquiring operation S3300 of the pore region information related to the scalp image, the pore region information may be acquired based on the scalp image acquired in operation S3100 and the parameter set acquired in operation S3200. Specifically, the neural network model having the parameter set acquired in operation S3200 may receive the scalp image acquired in operation S3100 through the input layer and output the pore region information. Accordingly, the scalp measuring device 1000 according to an embodiment of the present application may acquire pore region information related to the scalp image.

Meanwhile, the scalp measuring device 1000 according to an embodiment of the present application may update or update the parameter set of the trained neural network model in the deploying process P2000. For example, the pore region information acquired using the trained neural network model may be modified manually or by using any software. Here, the scalp measuring device 1000 may modify the parameter (or weight) of one or more nodes of the trained neural network model based on the difference between the pore region information before the modification and the modified pore region information. Accordingly, the neural network model may be updated or updated not only in the learning process of the neural network model but also in the deploying process. As the neural network model is updated in the scalp measuring device 1000, the accuracy of the neural network model outputting the pore region information may be improved.

Referring back to FIG. 34, the method of selecting the target image according to an embodiment of the present application may include acquiring quantitative information related to the pore region in operation S1300. For example, as described above, the number of pore regions may be calculated based on the pore region information acquired using the trained neural network model. Accordingly, the quantitative information related to the pore region included in the scalp image may be calculated.

FIG. 44 is a diagram illustrating an aspect of acquiring quantitative information related to the pore region according to an embodiment of the present application.

The pore region information acquired using the trained neural network model may include any information related to the pore region included in the scalp image. For example, the pore region information may include information on a position of the pore region included in the scalp image, information on a number of pore regions and/or information related to a number of hairs per pore region. For example, the first information Ba of FIG. 44 may include information on a position of the first pore region included in the scalp image within the scalp image and/or information indicating that the number of hairs is two in the first pore region. In addition, the second information Bb of FIG. 44 may indicate information on a position of the second pore region included in the scalp image within the scalp image and/or information indicating that the number of hairs is one in the second pore region.

In this case, the scalp measuring device 1000 according to an embodiment of the present application may perform an operation of calculating a quantitative information related to the pore region based on the pore region information including the first information Ba and the second information Bb. For example, the scalp measuring device 1000 may be implemented to calculate quantitative information related to the number of pore regions based on the pore region information including the first information Ba and the second information Bb. For example, the scalp measuring device 1000 may calculate the number of pore regions based on the pore region included in the scalp image obtained through the trained neural network model.

In addition, the scalp measuring device 1000 may be implemented to calculate quantitative information related to the number of hairs per pore based on the pore region information including the first information Ba and the second information Bb. For example, as described above, the first information Ba may indicate that the number of hairs is one in the first pore region. The second information Bb may indicate that the number of hairs is two in the second pore region. Similarly, the scalp measuring device 1000 may calculate the total number of hairs by obtaining the number of hairs for each pore region included in the pore region information. In this case, the scalp measuring device 1000 may calculate the quantitative information related to the number of hairs per pore based on the total number of hairs and the number of pore regions related to the scalp image.

In addition, the scalp measuring device 1000 may be implemented to calculate the quantitative information related to the pore density based on the pore region information including the first information Ba and the second information Bb. For example, the scalp measuring device 1000 may be implemented to calculate the total area of the scalp image. In addition, the scalp measuring device 1000 may calculate the total area of each pore region from the pore region information. In this case, the scalp measuring device 1000 may be implemented to calculate the quantitative information related to the pore density (e.g., the total area of the pore region/the total area of the scalp image) based on the total area of the scalp image and the total area of the pore region.

However, the above-described method of calculating the type and quantitative information of the quantitative information related to the pore region is merely exemplary, and the above-described quantitative information or the arbitrary type of quantitative information may be calculated by any appropriate method. In addition, although it is illustrated in FIG. 44 that quantitative information such as the number of pore regions, the number of hairs per pore, and the pore density are obtained based on the pore region information, this is merely exemplary, and it is of course, some of the quantitative information among the number of pore regions, the number of hairs per pore, and the pore density may not be calculated.

Referring back to FIG. 34, a method of selecting a target image according to an embodiment of the present application may include selecting a target image based on quantitative information (S1400). For example, the scalp measuring device 1000 may calculate quantitative information related to a pore region for each of a plurality of scalp images. In this case, the scalp measuring device 1000 may select a target image based on quantitative information related to a pore region of each of the plurality of scalp images. Specifically, the scalp measuring device 1000 may compare the quantitative information related to the pore region of each of the plurality of scalp images to select the target image. For example, the scalp measuring device 1000 may compare the quantitative information related to the pore region of each of the plurality of scalp images to select a scalp image having a larger quantitative value as the target image.

Figure 45:
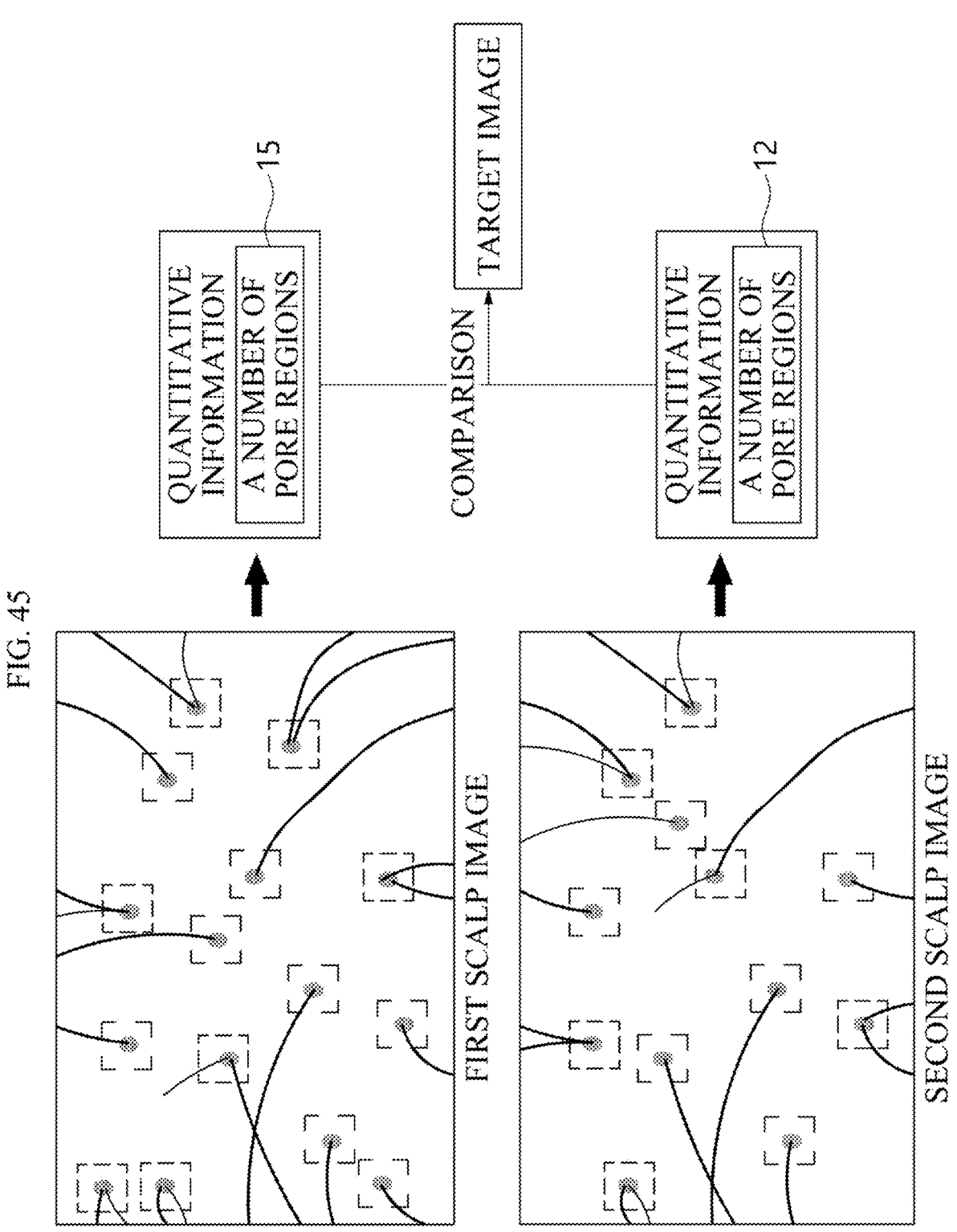
FIG. 45 is a diagram illustrating an aspect of selecting a target image.

FIG. 45 is a diagram illustrating an example of aspects of selecting a target image.

As described above, in operation S1100, a plurality of scalp images may be acquired. For example, in operation S1100, a plurality of scalp images including a first scalp image and a second scalp image may be acquired.

In this case, pore region information related to the first scalp image may be acquired using the trained neural network model as described above. In addition, quantitative information related to the first scalp image may be acquired based on the pore region information related to the first scalp image. Similarly, pore region information related to the second scalp image may be acquired using the trained neural network model. In addition, quantitative information of a pore region related to the second scalp image may be acquired based on the pore region information related to the second scalp image.

In addition, the scalp measuring device 1000 may select a target image based on the quantitative information related to the first scalp image and the quantitative information related to the second scalp image. Specifically, the scalp measuring device 1000 may compare the quantitative information related to the first scalp image and the quantitative information related to the second scalp image to select a scalp image having a larger value as the target image.

For example, referring to FIG. 45, information indicating that quantitative information (e.g., the number of pore regions) of a pore region related to the first scalp image includes a first quantitative value (e.g., 15) and quantitative information of a pore region related to the second scalp image includes a second quantitative value (e.g., 12) smaller than the first quantitative value (e.g., 15). In this case, the scalp measuring device 1000 may compare the quantitative information of the first scalp image and the quantitative information of the second scalp image to select a first scalp image having a larger value as the target image.

Meanwhile, the scalp measuring device 1000 may update or finally determine the target image by repeatedly performing the above-described processes with respect to the plurality of scalp images acquired in operation Si 100. Accordingly, a clear scalp image among the plurality of scalp images may be finally selected as the target image. Accordingly, the target image based on the calculation of the hair loss diagnosis assistance information may be optimally selected, and thus the hair loss diagnosis assistance information may be more accurately calculated.

Figure 47:
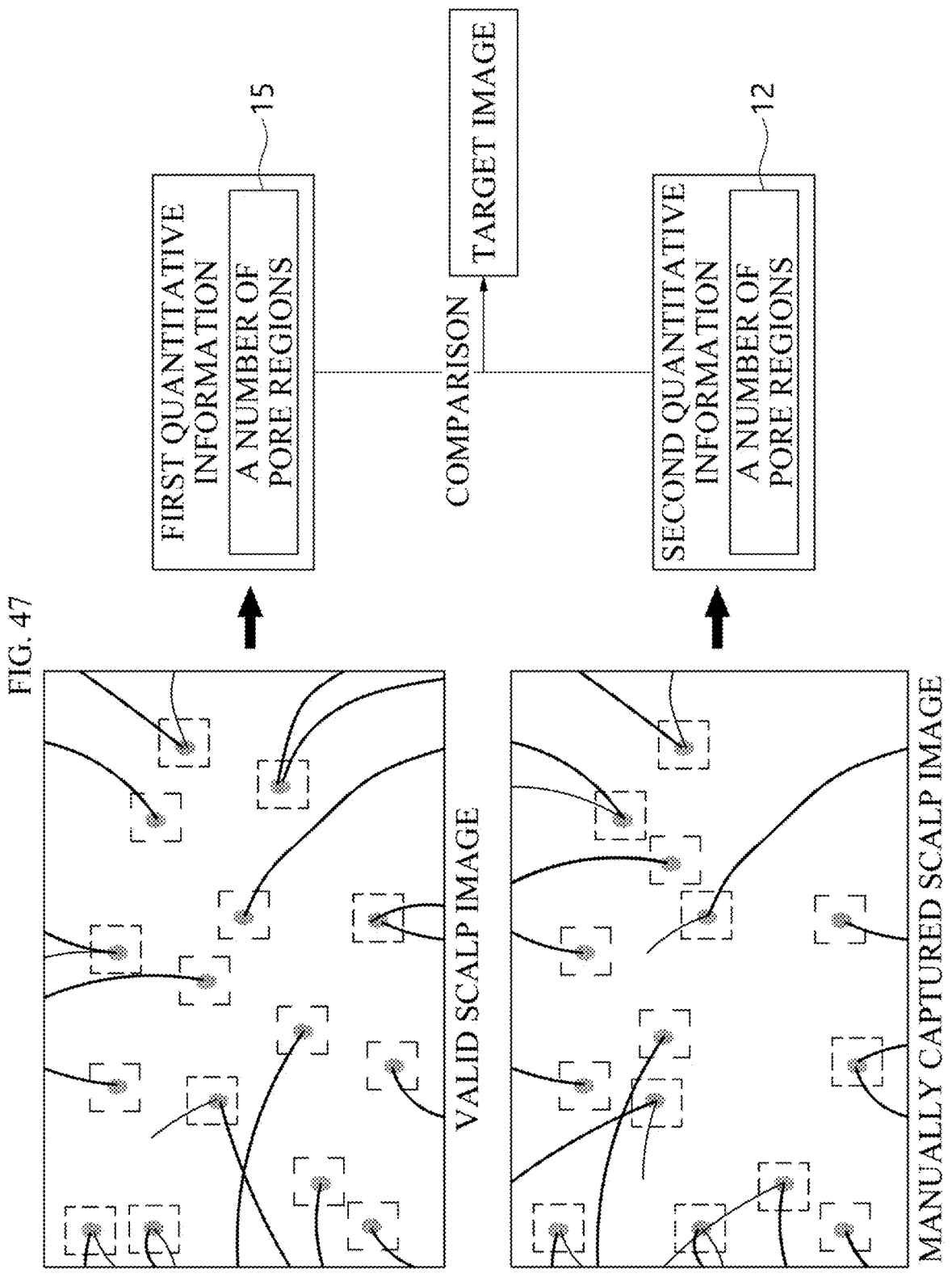
FIG. 47 is a diagram illustrating another aspect of selecting a target image.

Hereinafter, a method of selecting a target image according to another embodiment of the present application will be described in detail with reference to FIGS. 46 and 47. FIG. 46 is a flowchart illustrating a method of selecting a target image according to another embodiment of the present application. Specifically, FIG. 46 is a flowchart illustrating step S1400 of FIG. 34. FIG. 47 is a diagram illustrating another aspect of selecting a target image.

The method of selecting the target image according to the present embodiment may include: obtaining an valid scalp image and a manually captured scalp image (S1410); obtaining first quantitative information related to the number of pores of the valid scalp image (S1420); obtaining second quantitative information related to the number of pores of the manually captured scalp image (S1430); and determining the target image based on the first quantitative information and the second quantitative information (S1440).

In S1410, the valid scalp image and the manually captured scalp image may be obtained.

As described with reference to FIG. 35, the valid scalp image may refer to one or more scalp images selected from a plurality of scalp images obtained by continuously photographing the scalp as the camera 1110 of the scalp measuring device 1000 switches to the photographing mode. For example, pore region information may be obtained for each of the plurality of continuously photographed scalp images, and quantitative information related to the pore region may be calculated for each of the scalp images based on the obtained pore region information. In this case, the valid scalp image may refer to a scalp image having quantitative information including the largest value by comparing the quantitative information.

As described with reference to FIG. 36, the manually captured scalp image may refer to a scalp image obtained in response to a photographing input of the user through the input unit 1400. For example, the user may approach or contact the scalp region to be measured by the scalp measuring device 1000 and request a photographing operation of the camera 1110 through an input to the input unit 1400. In response to the user's input, the camera 1110 of the scalp measuring device 1000 may photograph the scalp image. The scalp image in this case may refer to the manually captured scalp image in the present specification.

In operation S1420 of obtaining the first quantitative information related to the number of pores of the valid scalp image, the first quantitative information related to the number of pore regions may be calculated based on the obtained pore region information of the valid scalp image.

Specifically, the trained neural network model may receive the valid scalp image and output the pore region information. In this case, the scalp measuring device 1000 may calculate the first quantitative information related to the number of pore regions based on the pore region information. For example, referring to FIG. 47, first quantitative information related to the valid scalp image indicating that the number of pore regions included in the valid scalp image is 15 may be calculated based on the pore region information of the valid scalp image output through the output layer of the trained neural network model.

In operation S1430 of obtaining the second quantitative information related to the number of pores of the manually captured scalp image, the second quantitative information related to the number of pore regions of the manually captured scalp image may be calculated based on the pore region information calculated for the obtained manually captured scalp image.

Specifically, the scalp measuring device 1000 may obtain pore region information related to the manually captured scalp image using the trained neural network model (see, for example, S1200 of FIG. 34), and obtain the second quantitative information related to the number of pore regions of the manually captured scalp image based on the pore region information (see, for example, S1300 of FIG. 5). For example, referring to FIG. 47, based on the pore region information of the manually captured scalp image output through the output layer of the trained neural network model, second quantitative information indicating that the number of pore regions included in the manually captured scalp image is 14 may be calculated.

In step S1440 of determining the target image based on the first quantitative information and the second quantitative information, the scalp measuring device 1000 may select the target image based on the first quantitative information and the second quantitative information. For example, the scalp measuring device 1000 may determine the target image by comparing the first quantitative information and the second quantitative information.

For example, referring to FIG. 47, the first quantitative information (e.g., the number of pore regions) of the pore region related to the valid scalp image may include a quantitative value indicating 15 and the second quantitative information of the pore region related to the manually captured scalp image may include a quantitative value indicating 14 smaller than 15. In this case, the scalp measuring device 1000 may compare the quantitative information of the valid scalp image and the manually captured scalp image to select a scalp image having a larger value as the target image. In addition, the scalp measuring device 1000 may be implemented to delete a scalp image having a smaller value as the quantitative information. For example, referring to FIG. 47, the valid scalp image having the quantitative information including the number of pore regions may be selected as the target image. In addition, the scalp measuring device 1000 may delete the manually captured scalp image having the smaller value as the quantitative information.

In relation to the aspect of selecting the target image, the above description was focused on selecting the target image by comparing the quantitative information related to the number of pore regions. However, this is merely an example for convenience of description, and it is also possible to select an optimal target image from among a plurality of scalp images by comparing other types of quantitative information (e.g., pore density, number of hairs per pore) other than the number of pore regions as the quantitative information.

According to the present embodiment, the target image may be selected as the optimal scalp image by determining the target image by additionally considering the quantitative information of the manually captured scalp image. In addition, since the hair loss diagnosis assistance information may be calculated based on the optimal target image, the reliability and accuracy of the hair loss diagnosis assistance information may be increased.

Although not shown in FIGS. 34 and 46, the scalp measuring device 1000 may transmit the determined target image to the server 3000 using any suitable communication method. The server 3000 may receive the target image and use the received target image to calculate the hair loss diagnosis assistance information. In this regard, the description will be given in detail with reference to FIGS. 48 to 58.

Meanwhile, the method of selecting the target image according to an embodiment of the present application may further include correcting the pore region information. For example, the pore region information obtained by outputting the trained neural network model may not be detected even when the pore region is present in the scalp image, or even when the pore region is a single pore region, there may be errors detected in duplication.

Accordingly, the scalp measuring device 1000 according to an embodiment of the present application may perform an operation of correcting the initial pore region information obtained using the trained neural network model. In addition, the scalp measuring device 1000 may obtain quantitative information related to the scalp image based on the corrected pore region information. In addition, the scalp measuring device 1000 may determine the target image based on the quantitative information calculated based on the corrected pore region information. Accordingly, the quantitative information for each scalp image may be calculated more accurately. In addition, since the target image may be selected by the accurately calculated quantitative information, the hair loss diagnosis assistance information may be calculated more accurately and more reliably.

The content related to the step of correcting the pore region information may be implemented similarly to the content of the step of obtaining the final pore region information (S4300 of FIG. 48) by correcting the initial pore region information of the server 3000 to be described later. Therefore, the content related to the step of correcting the pore region information will be described in detail later with reference to FIG. 48 and FIGS. 54 to 29.

Hereinafter, a method of obtaining hair loss diagnosis assistance information according to an embodiment of the present application will be described with reference to FIG. 48 to FIG. 58. The present embodiment may be performed by the server 3000. Alternatively, the present embodiment may be performed by the scalp measuring device 1000 or the electronic device 2000. However, the scalp measuring device 1000 or the electronic device 2000 may have a limit on the processing speed of data. Therefore, when the hair loss diagnosis assistance information is obtained by the scalp measuring device 1000 or the electronic device 2000, the hair loss diagnosis assistance information may be performed through an artificial neural network or algorithm that is simplified as compared to when the scalp measuring device 1000 or the electronic device 2000 is performed by the server 1000.

Figure 48:
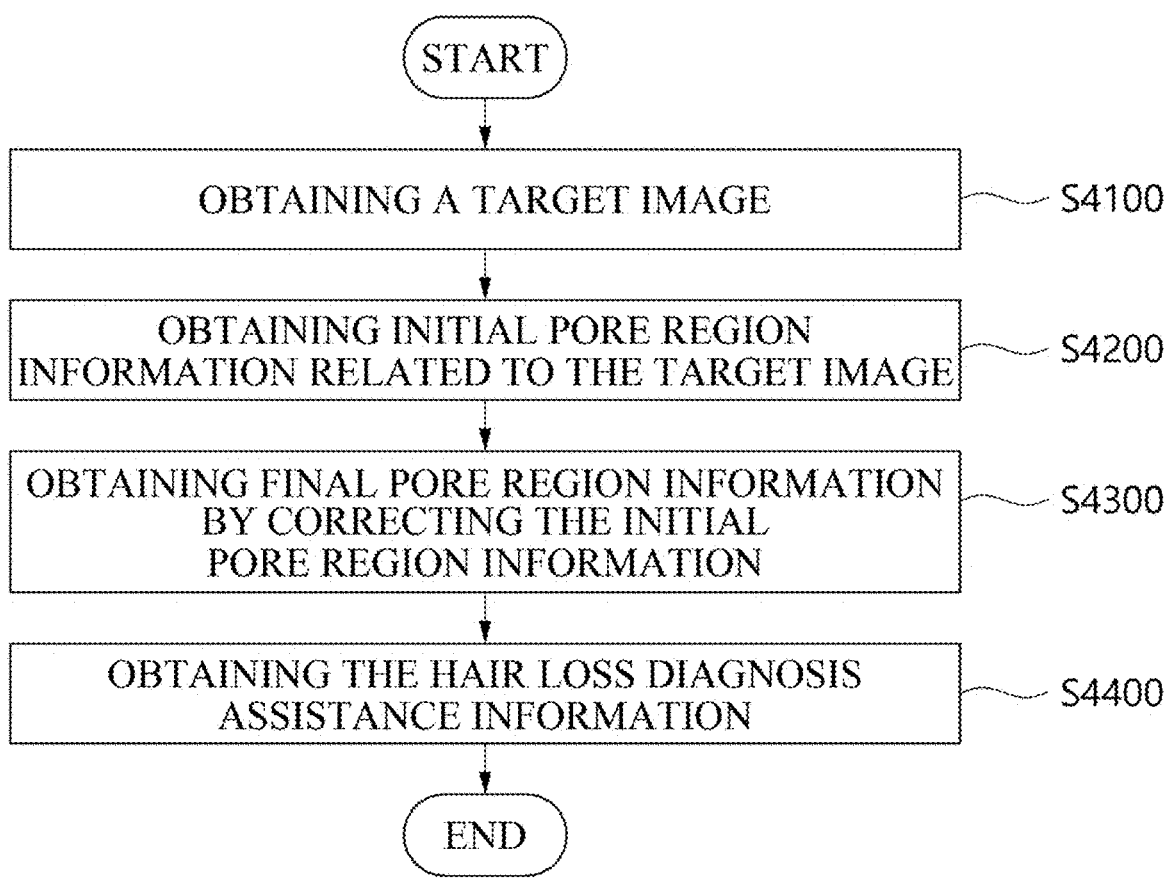
FIG. 48 is a flowchart illustrating a method of acquiring hair loss diagnosis assistance information according to an embodiment of the present application.

FIG. 48 is a flowchart illustrating a method of obtaining hair loss diagnosis assistance information according to an embodiment of the present application. The server 3000 may calculate the hair loss diagnosis assistance information from the target image and/or the sensing data. For example, the server 3000 may calculate the pore region information from the target image and calculate the hair loss diagnosis assistance information based on the pore region information. For another example, the server 3000 may calculate the scalp characteristic information from sensing data and calculate the hair loss diagnosis assistance information based on the scalp characteristic information. Here, the scalp characteristic information may mean a sense of including the target image and any information related to the scalp related to sensitivity, keratin amount, moisture, temperature, and odor that may be calculated as the sensing data.

Hereinafter, the calculation of the hair loss diagnosis assistance information using the target image will be described in detail. However, this is for convenience of description and is not limited thereto. The method of obtaining the hair loss diagnosis assistance information according to an embodiment of the present application may include obtaining a target image (S4100), obtaining initial pore region information related to the target image (S4200), obtaining final pore region information by correcting the initial pore region information (S4300), and obtaining the hair loss diagnosis assistance information (S4400).

In the step of obtaining the target image (S4100), the server 3000 may obtain the target image selected from the scalp measuring device 1000 or the electronic device 2000. Meanwhile, although not shown in FIG. 48, the server 3000 may obtain angle data related to the target image. Alternatively, the server 3000 may obtain sensing data including odor data, temperature data, and/or tactile data of the scalp area related to the target image.

Although not shown in FIG. 48, the method for calculating the hair loss diagnosis assistance information according to an embodiment of the present application may further include pre-processing the obtained target image. In other words, the target image described in step S4200 of FIG. 48 may be interpreted as a meaning that encompasses the preprocessed target image.

For example, the server 3000 may perform an image processing operation such as adjusting a pixel value and/or an intensity of the target image, reconfiguring the target image, or binarizeing the target image.

For example, the server 3000 may be implemented to calculate the hair loss diagnosis assistance information related to the sensitivity of the scalp of the user based on the target image. In this case, the server 3000 may determine a region having a red color series in the target image to determine the sensitivity of the scalp of the user, and determine the sensitivity of the scalp of the user based on a ratio of a size of the region having the red color series to a size of the analysis target image. In this case, before determining a plurality of pixels having the red color series in the target image, the server 3000 may perform pre-processing on the target image, and overlap a binarized image generated by binarizeing the target image to the preprocessed analysis target image through bit masking. Here, the pre-processing (or pre-filtering) may include image shape conversion through Dilation or Dilation+Erosion.

Meanwhile, the server 3000 may rereconstruct the preprocessed target image. Specifically, the server 3000 may determine an RGB value of each of the plurality of pixels of the preprocessed target image, and if it is determined that a pixel satisfying a predetermined condition exists based on the determined RGB value, the server 3000 may change a color value (or a color value) of the corresponding pixel to reconfigure the preprocessed target image. In this case, if there is a pixel satisfying the predetermined condition, the server 3000 changes only a color value of the pixel satisfying the predetermined condition, and maintains a color value of the remaining pixels not satisfying the predetermined condition. As described above, reconfiguring the target image is to reduce an R value of a pixel having a larger R value than another color value but having no large difference from another color value, so that the region having the red color series can be more clearly determined when determining the sensitivity.

Thereafter, the server 3000 may binarize the target image to generate a binarized image, and overlap the binarized image to the preprocessed target image through bit masking. Accordingly, the color value of the pixel of the target image may be standardized, so that the more accurate sensitivity of the scalp may be calculated. As another example, the server 3000 may be implemented to calculate the hair loss diagnosis assistance information related to the degree of smell of the scalp of the user based on the target image. In this case, the server 3000 may determine a pixel having a specific brightness among the plurality of pixels of the target image to determine the keratin amount of the scalp of the user, and determine the keratin amount of the scalp of the user based on the determined number of pixels. To this end, first, the server 3000 may perform pre-processing on the target image, and overlap the binarized image generated by binarization of the target image to the preprocessed analysis target image through bit masking. A detailed method thereof has been described above. Through this, the server 3000 may determine the reference brightness based on the brightness of each of the plurality of pixels of the target image (i.e., the image overlapped with the target image in which the binarized image is preprocessed), and determine the keratin amount of the scalp based on the number of pixels having a brightness greater than the determined reference brightness and the number of total pixels of the target image.

However, the above-described pre-processing is merely an example, and any suitable image processing method may be implemented as a pre-processing method of the target image for more precise analysis of the target image. For example, an operation of increasing the resolution of the target image or any image processing technique of removing noise that may exist in the target image may be performed.

In step S4200 of obtaining the initial pore region information related to the target image, the initial pore region information may be calculated based on the target image. Here, the initial pore region information may mean a comprehensive meaning of any information related to the scalp area included in the scalp image obtained from the target image. For example, the initial pore region information may include information on a plurality of regions included in the target image (e.g., information on each of the pore regions included in the target image and/or information on each of the hair regions included in the target image).

The initial pore region information may be obtained using a neural network model trained to receive the target image and output information related to the scalp characteristic. In this case, the trained neural network model may be the same as or different from the trained neural network model to obtain the pore region information to select the above-described target image. This will be described in detail below.

According to another embodiment, the server 3000 may obtain the initial pore region information using any algorithm or software.

Hereinafter, a learning method and a deploying method of a neural network model used to obtain initial pore region information in order to obtain hair loss diagnosis assistance information according to an embodiment of the present application will be described in detail with reference to FIGS. 49 to 52.

The learning method and the deploying method of the neural network model used to obtain initial pore region information may be used to analogize the contents of the learning method and the deploying method of the neural network model described above with reference to FIGS. 39, 40 and 43. Specifically, the process for obtaining the initial pore region information may include a learning process P1000 of the neural network model and a deploying process P2000 for obtaining the initial pore region information using the trained neural network model.

The learning process P1000 of the neural network model used to calculate the initial pore region information may be performed by the server 3000. In addition, the deploying process P2000 for calculating the initial pore region information using the trained neural network model may be performed by the server 3000. Alternatively, the deploying process P2000 for calculating the initial pore region information by the scalp measuring device 1000 or the electronic device 2000 may be performed by a node of the trained neural network model by transmitting a parameter (or weight) to the scalp measuring device 1000 or the electronic device 2000. Hereinafter, it will be described that the learning process P1000 and the deploying process P2000 of the neural network model for calculating the initial pore region information are performed in the server 3000. However, this is for convenience of description, and the deploying process P2000 using the neural network model trained to calculate the initial pore region information as described above may be performed in the scalp measuring device 1000 or the electronic device 2000.

The learning process P1000 according to the present embodiment may include a process P1100 for obtaining a learning data set, a process P1200 for learning a neural network model, a process P1300 for verifying a neural network model, and a process P1400 for obtaining parameters of the neural network model. In addition, similar to FIG. 40, the method for learning a neural network model according to the present embodiment may include obtaining a learning data set, screening a learning data set, learning and verifying a neural network model, and obtaining parameters of the neural network model.

The deploying process P2000 according to the present embodiment may include a process P2100 for obtaining a target image and a process P2200 for obtaining initial pore region information. In addition, similar to FIG. 43, the method for deploying a neural network model according to the present embodiment may include obtaining a target image, obtaining a parameter set of a neural network model, and obtaining initial pore region information related to a scalp image based on the parameter set of the neural network model.

Hereinafter, a method for learning a neural network model used to obtain initial pore region information will be described in more detail with reference to FIGS. 42, 49 and 50.

Figure 49:
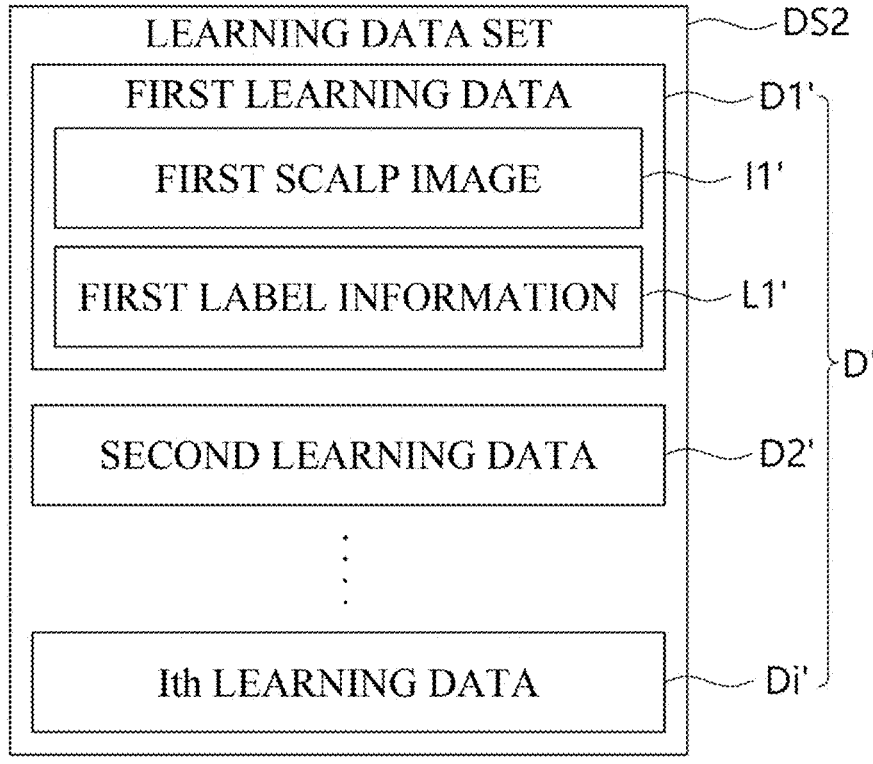
FIG. 49 is a schematic structure diagram of a learning data set according to an embodiment of the present application.

FIG. 49 is a diagram illustrating a structure of a learning data set according to an embodiment of the present application. The learning data set DS2 may be a basis for learning a neural network model. The learning data set DS2 may include one or more learning data D'. For example, the learning data set DS2 may include first learning data D1' and second learning data D2' to i-th learning data D1'. Here, each of the one or more learning data included in the learning data set DS2 may include a scalp image and label information. For example, the first learning data D1' included in the learning data set DS2 may include a first scalp image I1' and first label information L1'.

Figure 50:
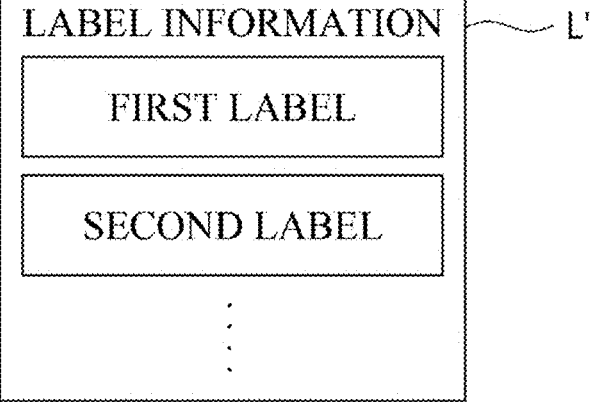
FIG. 50 is a schematic structure diagram of label information included in a learning data set (DS2) according to an embodiment of the present application.

FIG. 50 is a diagram illustrating a structure of label information included in the learning data set DS2 according to an embodiment of the present application. The label information (e.g., the i-th label information L1') included in the learning data set DS2 may include one or more labels. Specifically, each of the scalp images included in the learning data set DS2 may include label information. In this case, a plurality of labels may be assigned to label information for each of the scalp images.

For example, the learning data of the learning data set DS2 may include a first label related to a pore region assigned to the scalp image. Specifically, the first label indicating the pore region may be automatically or manually assigned to the scalp image of the learning data set DS2.

As another example, the label may be automatically or manually assigned to the scalp image by being differently classified according to the number of hairs per unit pore region included in the scalp image of the learning data set DS2. For example, the second label may be assigned to a specific pore region having the number of hairs per unit pore region N in the scalp image of the learning data set DS2. Specifically, the 2-1 label may be assigned to the specific pore region having the number of hairs per unit pore region in the scalp image of the learning data set DS2. The 2-2 label may be assigned to the specific pore region having the number of hairs per unit pore region in the scalp image of the learning data set DS2.

Meanwhile, as described above, the server 3000 may obtain the scalp characteristic information based on the sensing data and/or the target image. In this case, the server 3000 may train the neural network model to calculate the scalp characteristic information (or the scalp characteristic initial information) using the sensing data and/or the target image as the input data. For example, the neural network model for calculating the scalp characteristic information based on the input data and the neural network model for calculating the pore region initial information based on the target image may be the same. In this case, the input data may be assigned a label related to additional scalp characteristics other than the first label related to the pore region and the second label related to the number of hairs per unit pore region described above. As another example, the neural network model for calculating the scalp characteristic information and the neural network model for calculating the pore region initial information may be separate. Specifically, the pore region initial information and the scalp characteristic information output through each neural network model by inputting the target image and the sensing data into separate neural network models may be combined as appropriate. In this case, in order to train the neural network model for calculating the scalp characteristic information, the sensing data may be assigned a label related to the scalp characteristic.

The scalp image and the label information included in the learning data may be based on training the neural network model and verifying the neural network model in relation to the learning method of the neural network model according to an embodiment of the present application.

The neural network model for outputting the pore region initial information may be trained as described above with respect to FIG. 42. Specifically, the neural network model may be trained by adjusting a parameter (or weight) of a node of the neural network model so that a difference between the output data and the label information is minimized.

The neural network model for obtaining the pore region initial information according to an embodiment of the present application may be a Darknet Yolo, R-CNN, or a Fast R-CNN model. However, this is merely an example, and as described above, various image segmentation algorithms including image segmentation using the neural network model may be used.

The trained neural network model may be verified as described above with respect to FIG. 40. Specifically, the trained neural network model may be verified based on some learning data (hereinafter, referred to as verification learning data) included in the learning data set DS2. For example, the trained neural network model may receive the scalp image of the verification learning data and output the output data. In this case, the trained neural network model may be verified based on the label information included in the verification learning data and the output data output through the trained neural network model. Specifically, by comparing the similarity of the output data output through the trained neural network model with the label information included in the verification learning data, it may be verified whether the parameter (or weight) of the node of the hidden layer of the trained neural network model is appropriate.

As described above, the server 3000 may train the neural network model to output the pore region initial information based on the learning data set DS2 and repeatedly perform an operation of verifying the neural network model. Through this, the server 3000 may obtain a neural network model including a node having a parameter (or weight) where a difference between the label information L' included in the learning data D' and the output data is minimized.

The obtained node parameter (or weight) and the trained neural network model may be used to calculate pore region initial information in the deploying process P2000.

Similar to the above described with reference to FIG. 43, a deploying method using a neural network model trained to obtain pore region initial information according to the present embodiment may include obtaining a target image, obtaining a parameter set of the neural network model, and obtaining pore region initial information based on the target image and the parameter set of the neural network model.

In the step of obtaining the target image, the server 3000 may obtain the target image from the scalp measuring device 1000 or the electronic device 2000 by using any communication method. For example, the server 3000 needs to obtain accurate hair loss diagnosis assistance information by more specifically analyzing the target image. Therefore, the server 3000 may obtain the target image having the original resolution from the scalp measuring device 1000 or the electronic device 2000.

In the step of obtaining the parameter set of the neural network model, the parameter set (or weight) of the trained neural network model may be obtained with reference to FIGS. 49 to 50.

Figure 51:
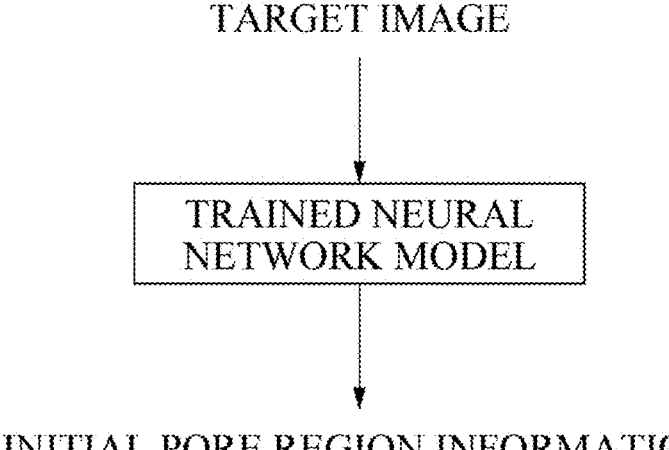
FIG. 51 is a schematic diagram illustrating a deploying operation of a trained neural network model according to an embodiment of the present application.

In the step of obtaining the pore region initial information based on the target image and the parameter set of the neural network model, the server 3000 may calculate the pore region initial information based on the obtained target image and the neural network model having the obtained parameter set. Referring to FIG. 51. FIG. 51 is a schematic diagram illustrating a deploying operation of a trained neural network model according to an embodiment of the present application. Specifically, the target image may be input to an input layer of the neural network model including the parameter set updated to output pore region initial information. The trained neural network model may output pore region initial information related to the target image based on the target image through the output layer. More specifically, the trained neural network model may receive the target image through the input layer and output the pore region initial information through the output layer.

Meanwhile, although FIG. 51 has been described based on outputting pore region initial information based on the target image, this is for convenience of description, and the learning process and the deploying process of the neural network model may be configured to output sensing data to output initial pore region initial information and scalp initial information or to output sensing data and target image as input data.

Figure 52:
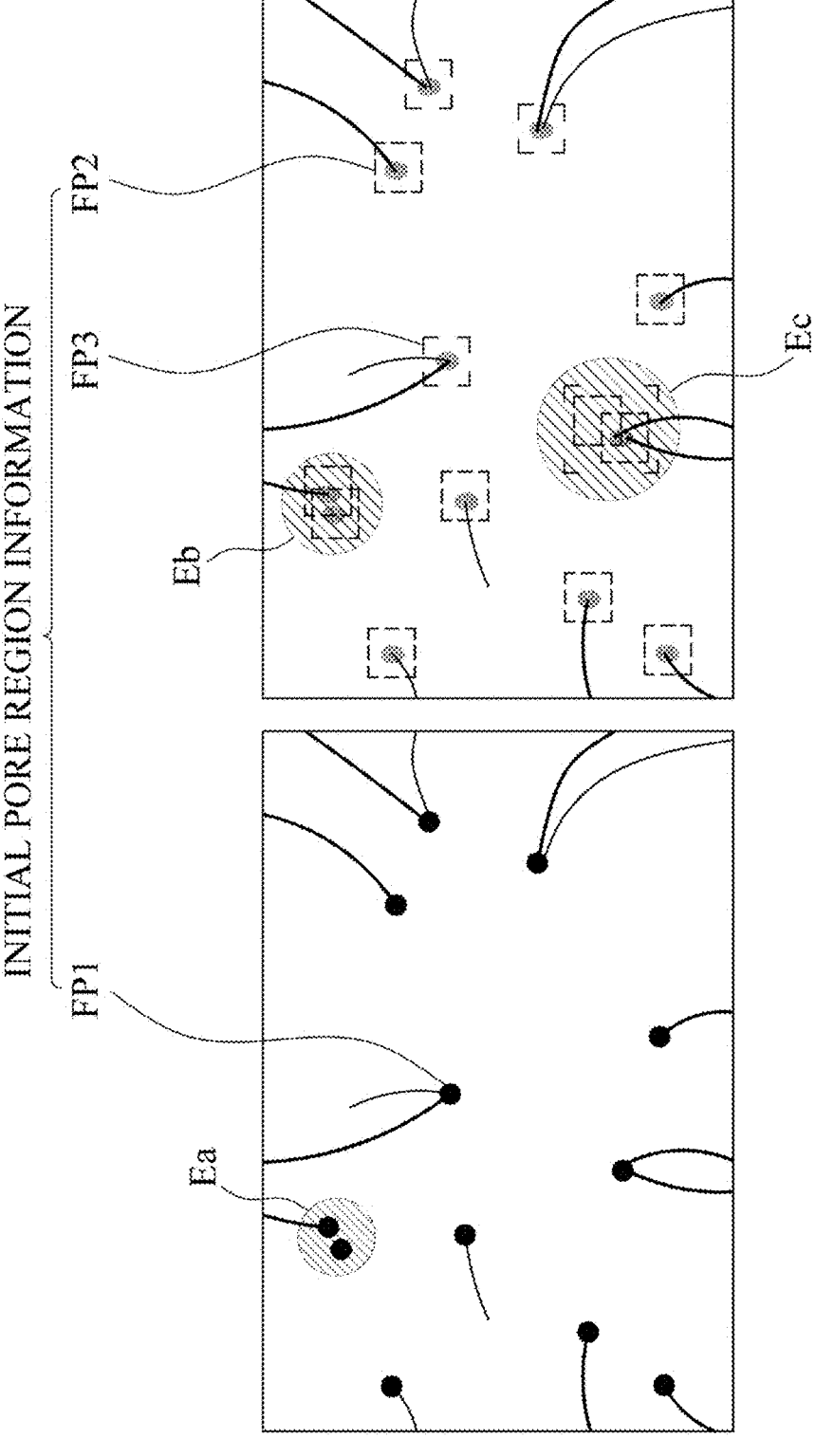
FIG. 52 is a diagram illustrating an example for describing initial pore region information according to an embodiment of the present application.

Referring to FIG. 52. FIG. 52 is an exemplary diagram for describing pore region initial information according to an embodiment of the present application. The pore region initial information may include information related to one or more pore regions. For example, the pore region initial information may include first information FP1. The first information FP1 may mean to include location information related to the pore region included in the target image and/or information related to the number of pore regions. For another example, the pore region initial information may include second information. The second information may be information related to the number of hairs per unit pore region included in the target image. For example, when there is one hair per unit pore region, information FP2 indicating that a hair is one hair per unit pore region may be included in the pore region initial information. As another example, when there are two hairs per unit pore region, information FP3 indicating that a hair is two hair per unit pore region may be included in the pore region initial information.

However, the pore region initial information shown in FIG. 52 is merely an example drawing for convenience of description, and information indicating that the number of hairs per unit pore region is i and/or information indicating the number of hairs may be output as the pore region initial information.

The pore region initial information acquired from the target image may be one or more for each type of information. For example, one target image may include a pore region corresponding to a plurality of pores. In this case, the server 3000 may acquire information on one or more pore regions included in the target image. Specifically, the server 3000 may acquire first information on the first pore region and first information on the second pore region included in the target image. For example, one target image may include a pore region corresponding to a plurality of pores having a hair i. For example, the target image may include a first pore region having a hair i and a second pore region having a hair i. In this case, the pore region initial information acquired by the server 3000 may include information FP2 indicating that the first pore region has a hair i and information FP2 indicating that the second pore region has a hair i.

Meanwhile, the pore region initial information may be output through the output layer of the neural network model in different forms for each type of information. For example, the pore region information FP1 may be overlaid with information of the first type (e.g., a point) and output through the output layer of the neural network model.

On the other hand, the information associated with the number of hairs per unit pore region (FP2, FP3, and FP4) may be overlaid with information of the second type (e.g., a bounding box) and output through the output layer of the neural network model. In particular, even within the information associated with the number of hairs per unit pore region, information of different forms may be overlaid according to the number of hairs. For example, the information associated with the 2-1 type (e.g., the first bounding box) may be overlaid with information FP2 indicating that one hair per unit pore region and output through the output layer of the neural network model. On the other hand, the information associated with the 2-2 type (e.g., the second bounding box) may be overlaid with information FP3 indicating that two hairs per unit pore region and the information associated with the 2-3 type (e.g., the third bounding box) may be overlaid with information FP4 indicating that three hairs per unit pore region and output through the output layer of the neural network model.

The pore region initial information may be output in the form of probability information. For example, the pore region initial information may be provided in the form of a probability map including a probability value for the first information (e.g., FP1) and/or a probability value for the second information (e.g., FP2, FP3, and FP4). The probability information may be used to correct the pore region initial information as described below with reference to FIGS. 54 to 58.

Meanwhile, hair removal assist diagnosis information may be calculated based on the pore region initial information. However, as shown in FIG. 52, there is a possibility that errors exist in the initial information of the pore region output through the trained neural network model. Specifically, the pore region initial information may have an error in which information to be calculated is missing or information that should not be calculated is additionally calculated.

For example, in reality, an error Ea obtained by the same pore region or two pore regions may exist. As another example, in reality, an error Eb calculated such that a pore region including only second information having one hair per unit pore region has 2-1 information having one hair per first pore region and 2-2 information having one hair per second pore region. As still another example, in reality, for a pore region having two hairs per one pore region, an error Ec may exist in which information indicating that one hair per unit pore region has one hair and information indicating that one hair per unit pore region has one hair additionally are additionally obtained in addition to the second information indicating that two hairs per unit pore region.

Therefore, the method of obtaining the hair loss diagnosis assistance information according to the embodiment of the present application may include a step (S4300 of FIG. 48) of obtaining pore region final information by correcting the initial information of the pore region. However, the initial information of the pore region is only written as the initial information of the pore region in order to distinguish the corrected pore region final information, and is not construed as limited thereto. Therefore, when there is no error, the initial information of the pore region and the final information of the pore region may be used in the same meaning. In other words, when there is no error, the server 3000 may be implemented to obtain the hair loss diagnosis assistance information based on the initial information of the pore region.

An operation of correcting the initial information of the pore region will be described in detail below with reference to FIGS. 54 to 58.

Meanwhile, a neural network model (hereinafter, referred to as a first neural network model) trained to output pore region information to select the target image described with reference to FIGS. 37 to 47 and a second neural network model (hereinafter, referred to as a second neural network model) trained to output pore region initial information (or pore region final information) to calculate the hair loss diagnosis assistance information described with reference to FIGS. 48 to 58 may be different or the same (including some of the same).

For example, as described above, the operation of selecting the target image may be performed by the scalp measuring device 1000 or the electronic device 2000. In this case, in order to improve the data processing speed of the scalp measuring device 1000 or the electronic device 2000, the first neural network model may be trained to output pore region information for selecting the target image by simplifying the configuration of the first neural network model than the second neural network model. For example, in terms of improving the speed of the scalp measuring device 1000 or the electronic device 2000, the first neural network model may be trained and deployed by lowering the resolution of the scalp image input to the input layer of the first neural network model. Specifically, the first neural network model may be trained using Darknet Yolo. In this case, when the anchor box is set to train the first neural network model, the first neural network model may be trained using a relatively small number (e.g., six cases) of acker boxes than the case of training the second neural network model. Accordingly, the configuration of the neural network model may be simplified, and thus the first neural network model for outputting the pore region information may be trained. Since the target image may be selected using the first neural network model including the simplified configuration, the data throughput of the scalp measuring device 1000 or the electronic device 2000 may be reduced. Accordingly, the data processing speed of the scalp measuring device 1000 or the electronic device 2000 may be increased.

On the other hand, there may be a need for an operation of selecting the target image of the scalp measuring device 1000 or the electronic device 2000 to be finely performed. In this case, there may be a need for the configuration of the first neural network model to be simplified for more sophisticated analysis. For example, the second neural network model may be trained to output initial pore region information (or final pore region information) related to the target image by more finely analyzing the selected target image. For example, in order to more finely analyze the selected target image, the second neural network model may receive the target image of the "original" having a high resolution into the input layer or may be trained by preset a relatively large number (e.g., nine anchor boxes). In this case, when there is a need for accurately selecting the target image, the first neural network model may be configured substantially the same as the second neural network model and may be trained. Accordingly, the target image may be more finely selected using the first neural network model and the target image may be more finely analyzed using the second neural network model, and thus the final pore region information may be accurately calculated.

Meanwhile, in order to calculate the hair loss diagnosis assistance information, as described above, a pre-processing operation of the target image or a post-processing operation of correcting the initial pore region information output through the neural network model may be performed before being input to the second neural network model. In this case, the above-described pre-processing operation and/or the post-processing operation may be appropriately performed in an operation for selecting the target image according to performance of an application processor (AP) or a central processing unit (CPU) of the scalp measuring device 1000 or the electronic device 2000. For example, an operation of preprocessing the scalp image may be performed before being input to the first neural network model. Alternatively, a post-processing operation of correcting the pore region information output through the first neural network model may be performed. Accordingly, the target image may be finely selected.

On the other hand, for another example, an operation of preprocessing the scalp image may be omitted before being input to the first neural network model. Alternatively, a post-processing operation of correcting the pore region information output through the first neural network model may be omitted. Accordingly, the processing speed of selecting the target image may be improved.

However, the above description is merely an example, and the first neural network model and the second neural network model may be trained in any appropriate configuration considering both the sophistication and the speed improvement aspects of the scalp image analysis. For example, the first also may be configured to perform at least some operations of the pre-processing and/or post-processing operations of the scalp image described above in each of the operation of selecting the target image and the operation of calculating the hair loss diagnosis assistance information in consideration of both the sophistication and the speed improvement aspects of the scalp image analysis. Alternatively, at least some operations may be omitted in each of the operation of selecting the target image and the operation of calculating the hair loss diagnosis assistance information.

Referring back to FIG. 48, the method of obtaining the hair loss diagnosis assistance information according to an embodiment of the present application may include acquiring pore region final information by correcting the pore region initial information (S4300).

The accuracy and objectivity of the hair loss diagnosis assistance information is an important factor in providing the hair loss diagnosis assistance information to the user. However, as described above, errors may exist in the pore region initial information output through the trained neural network model. Accordingly, according to an embodiment of the present application, the server 3000 may perform an operation of correcting the pore region initial information. However, when the errors do not exist in the pore region initial information, the hair loss diagnosis assistance information may be calculated based on the pore region initial information. That is, when the errors do not exist in the pore region initial information, the operation of acquiring the pore region final information by correcting the pore region initial information (S4300) may be omitted.

Figure 53:
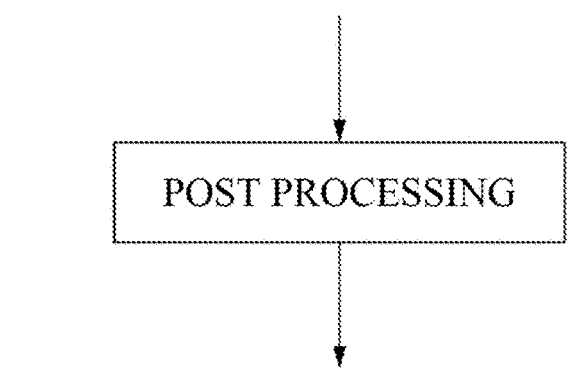
FIG. 53 is a schematic diagram illustrating a post processing operation according to an embodiment of the present application.

Reference is made to FIG. 53. FIG. 53 is a schematic diagram illustrating a post-processing operation according to an embodiment of the present application. The server 3000 may acquire the pore region final information by performing a post-processing operation of correcting the pore region initial information. The server 3000 may calculate the hair loss diagnosis assistance information based on the pore region final information.

Figure 54:
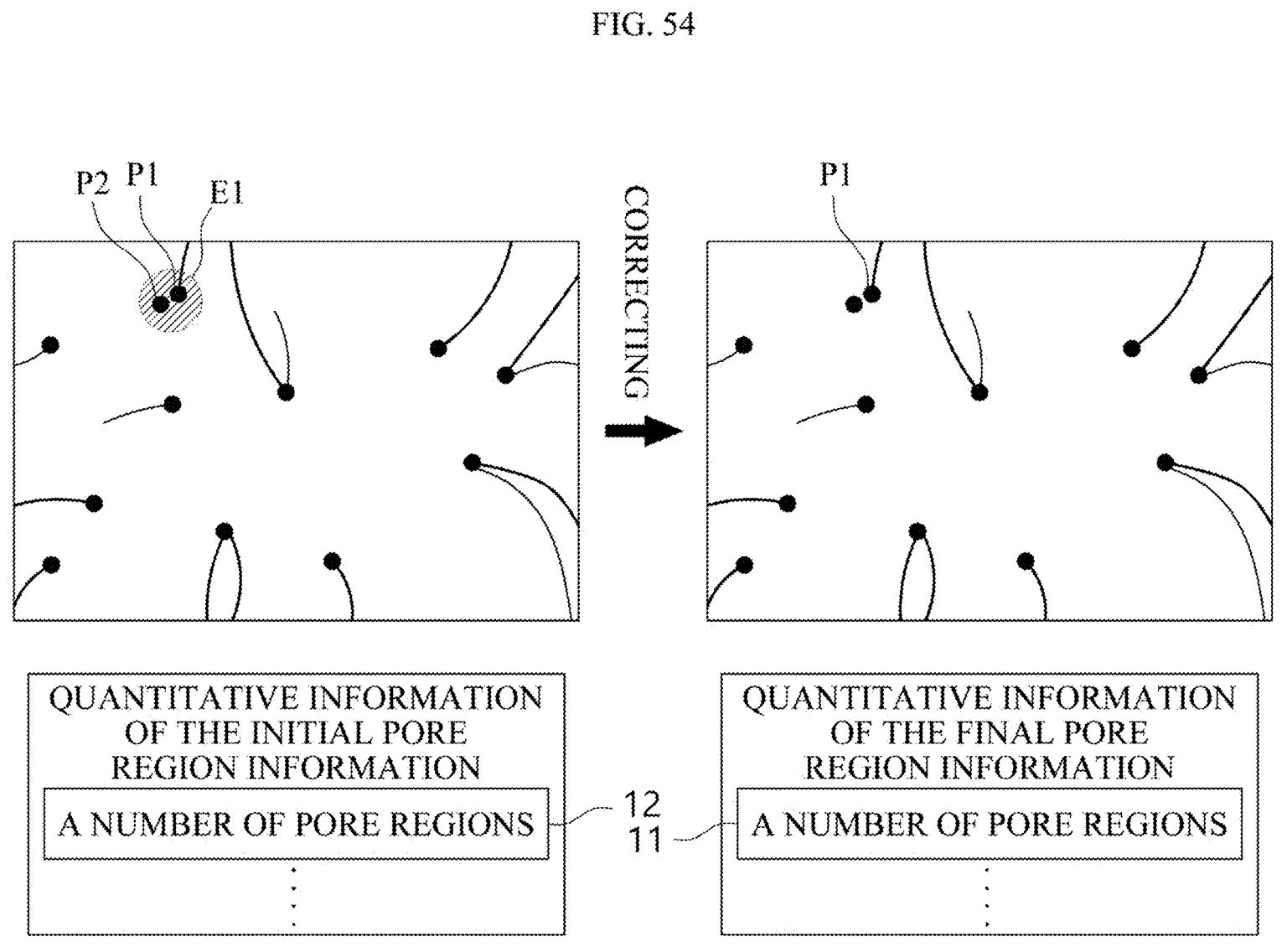

Hereinafter, the post-processing operations according to an embodiment of the present application will be described in detail with reference to FIGS. 54 to 28. FIGS. 54 to 57 are views illustrating aspects of post-processing according to an embodiment of the present application, respectively.

The pore region initial information may include information related to the pore region. However, an error may exist in the information related to the pore region. For example, even though the acquired pore region is actually one, the pore region initial information may exist a case where the pore region is obtained by overlapping. For example, even though one pore region should be actually acquired in the region E1 of FIG. 54, there may be errors acquired by two pore regions P1 and P2.

The server 3000 according to an embodiment of the present application may perform an operation of correcting the overlappingly acquired pore region. For example, the server 3000 may correct the overlappingly acquired pore region based on position information of the acquired pore regions in the scalp image related to the pore region. For example, the server 3000 may acquire first position information of the first pore region (e.g., P1 of FIG. 55) in the scalp image and second position information of the second pore region (e.g., P2 of FIG. 55) in the scalp image. Here, the first position information and/or the second position information may be in the form of coordinate information of a pixel in the scalp image. The server 3000 may determine whether the first pore region and/or the second pore region acquired based on the first position information and the second position information are valid. For example, when the separation distance between the first position information and the second position information is within a predetermined distance, the server 3000 may determine that at least one of the first pore region and/or the second pore region is not valid. Specifically, when the separation distance between the first position information and the second position information is within the predetermined distance, it may mean that the first pore region and the second pore region are closely adjacent to each other and a possibility that one pore region is overlapped and acquired is high. Therefore, when the separation distance between the first position information and the second position information is within the predetermined distance, the server 3000 may determine that at least one of the first pore region and/or the second pore region is not valid and correct the first pore region and the second pore region as one pore region. For example, the server 3000 may determine that at least one of the first pore region and/or the second pore region (e.g., P2 in FIG. 55) is not valid and determine the pore region (e.g., P1 in FIG. 55) determined to be valid as final pore region information. On the other hand, the server may perform correction of excluding the pore region (e.g., P2 in FIG. 55) determined to be not valid from the initial pore region information.

Here, the server 3000 may consider a probability value included in the pore region information in order to determine an invalid pore region among the first pore region and/or the second pore region. For example, the initial pore region information acquired through the trained neural network model as described above may include probability information on the pore region. In this case, the server 3000 may determine an invalid pore region based on the probability information of the first pore region and the second pore region overlapped and acquired. For example, when the first probability information related to the first pore region has a probability value higher than the second probability information related to the second pore region, the server 3000 may perform correction of including the first pore region as final pore region information and removing the second pore region from the initial pore region information. Through such correction, the server 3000 may correct information related to the number of pore regions related to the initial pore region information (e.g., the number of 12 pore regions in FIG. 55), and acquire final pore region information including information related to the corrected number of pore regions (e.g., the number of 11 pore regions in FIG. 55).

Meanwhile, when the separation distance between the first position information and the second position information is not within the predetermined distance, the server 3000 may determine that the first pore region and/or the second pore region are valid. When the separation distance between the first position information and the second position information is within the predetermined distance, it may mean that the first pore region and the second pore region are sufficiently spaced apart and each may correspond to one pore region. Therefore, when the separation distance between the first position information and the second position information is not within the predetermined distance, the server 3000 may determine that the first pore region and the second pore region are valid.

Figure 55:
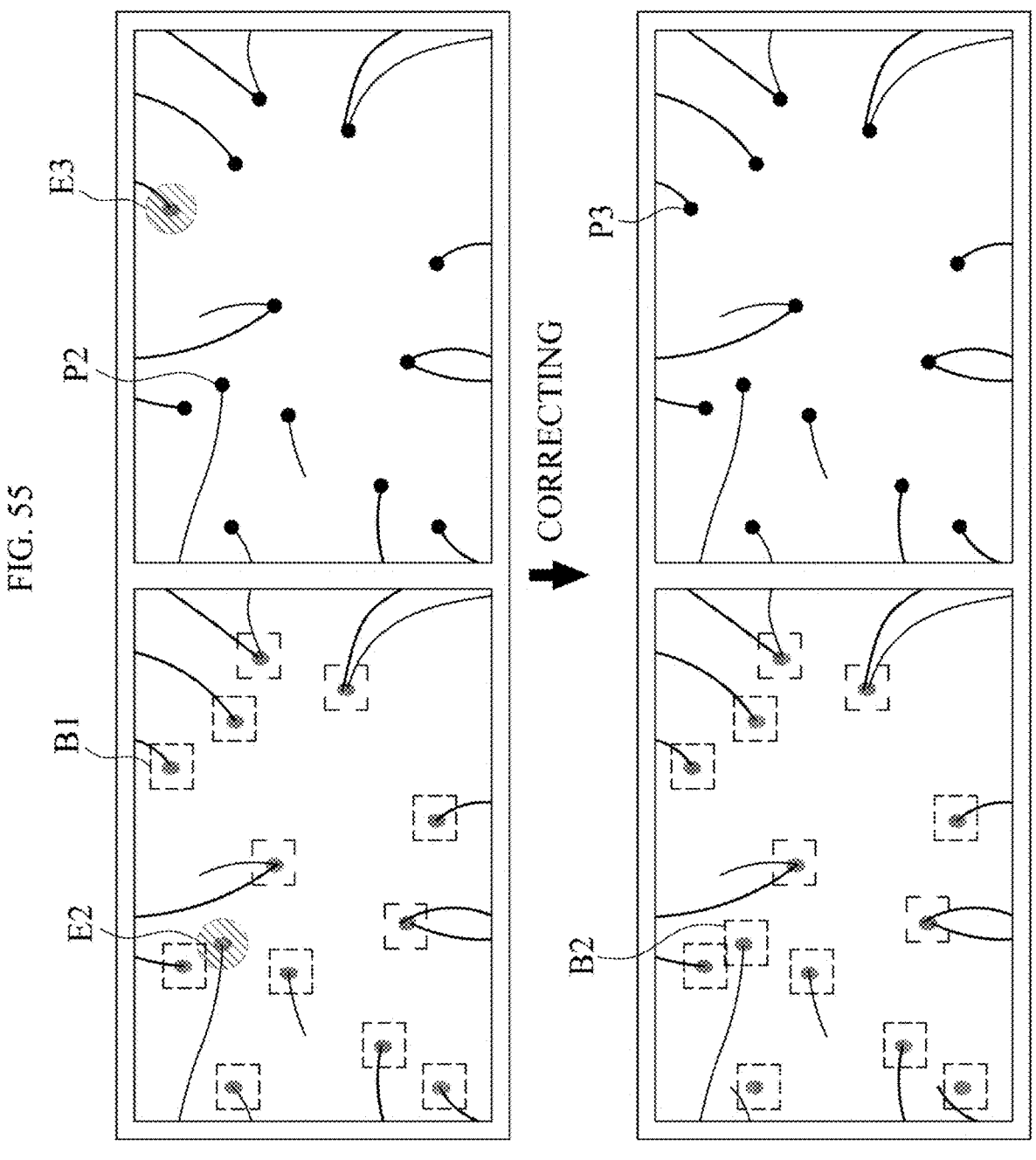

Referring to FIG. 55, the initial pore region information may include first information related to the pore region (e.g., P2 in FIG. 55) and second information related to the number of hairs per unit pore region (e.g., B1 in FIG. 55). In this case, since the second information related to the number of hairs per unit pore region generally accompanies the first information on the pore region, the second information related to the number of hairs per unit pore region and the first information on the pore region may have a high possibility of being corresponding to each other.

For example, when the pore region is present, the second information related to the number of hairs per pore region corresponding to the corresponding pore region should be acquired together, except for the case where the hairs are not present in the pore region. However, even when the pore region is actually present and the hairs are present in the pore region, an error may occur in which the second information related to the number of hairs per unit pore region is not acquired. For example, although the first information P2 on the specific pore region is acquired in relation to the area E2 of FIG. 55, an error may occur in which the second information related to the number of hairs per unit pore region corresponding to the corresponding pore region P2 is not acquired.

As another example, since the second information related to the number of hairs per unit pore region is information on the number of hairs present in the pore region, the second information related to the number of hairs per unit pore region should be acquired together with the first information related to the corresponding pore region. However, although the second information related to the number of hairs per unit pore region is acquired, an error may occur in which the first information on the corresponding pore region is not acquired. For example, in relation to the area E3 of FIG. 55, the second information (e.g., B1) related to the number of hairs per unit pore region is acquired but the first information on the corresponding pore region may not be acquired.

The server 3000 according to an embodiment of the present application may perform an operation of correcting the above-described error. The server 3000 may correct the error of the above-described initial pore region information based on whether the first information on the pore region corresponds to the second information related to the number of hairs per unit pore region.

For example, the server 3000 may acquire an error area based on whether the first information on the pore region corresponds to the second information related to the number of hairs per corresponding pore region. For example, when the first information (e.g., P2 of FIG. 55) on the first pore region is acquired and the second information related to the number of hairs per unit pore region corresponding to the first pore region is not acquired, the server 3000 may determine the neighboring area of the first pore region as the error area (e.g., E2 of FIG. 55). For another example, when the second information (e.g., B1 of FIG. 55) related to the number of hairs per unit pore region related to the second pore region is acquired and the first information on the second pore region is not acquired, the server 3000 may determine the neighboring area of the second pore region as the error area (e.g., E3 of FIG. 55).

The server 3000 may correct at least one of the first information on the pore region and the second information related to the number of hairs per unit pore region based on the acquired error area. For example, if first information (e.g., P2 of FIG. 55) about the first pore region has been acquired and second information related to the number of hairs per unit pore region corresponding to the first pore region has not been acquired, the server 3000 may assign second information (e.g., B2 of FIG. 55) related to the number of hairs per pore region related to the first pore region to the target image. Similarly, if second information (e.g., B1 of FIG. 55) related to the number of hairs per pore region related to the second pore region has been acquired and first information about the second pore region has not been acquired, the server 3000 may assign first information (e.g., P3 of FIG. 55) about the second pore region to the target image.

Figure 56:
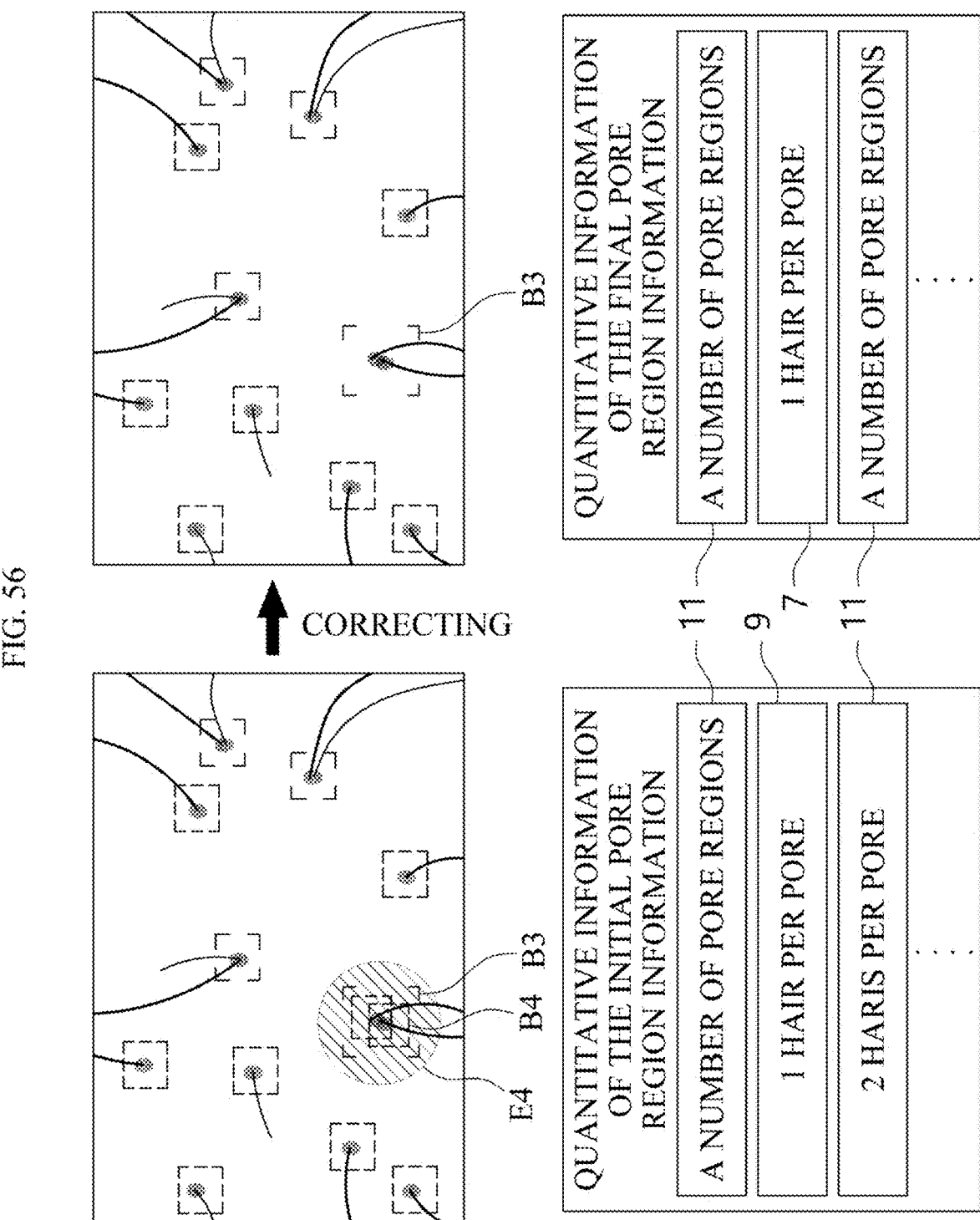

Referring to FIG. 56, the initial pore region information may include second information (e.g., B3 and B4 of FIG. 56) related to the number of hairs per unit pore region. However, there may be an error in the second information related to the number of hairs per unit pore region. For example, the second information related to the number of hairs per unit pore region may be obtained in duplicate. For example, referring to the error region E4 of FIG. 56, although there are two hairs in one pore, the 2-1 information (e.g., B3) where two hairs are present in one pore region and the 2-2 information (e.g., B4) where one hair is present in two pore regions may be simultaneously acquired. Referring to the quantitative information of the initial pore region information of FIG. 56, the total number of hair regions is 11, while the total number of information related to the number of hairs per pore is 13 exceeding 11.

The server 3000 according to an embodiment of the present application may be implemented to perform the operation of correcting the error described above. For example, the server 3000 may correct the initial pore region information based on the degree of overlap of the information about the number of hairs per unit pore region. Specifically, when the degree of overlap between the information about the number of hairs per unit pore region exceeds a predetermined ratio, the server 3000 may determine that an error exists in the information about the number of hairs per unit pore region. In addition, the server 3000 may correct the initial pore region information based on the result of determining that an error exists.

The server 3000 may correct the error based on the probability information of the information about the number of hairs per pore region overlapping with each other. For example, if the first probability information related to the 2-1 information (e.g., B3) of FIG. 56 has a first value and the second probability information related to the 2-2 information (e.g., B4) of FIG. 56 has a second value lower than the first value, the server 3000 may determine that the 2-1 information (e.g., B3) is valid and include the 2-1 information in the final pore region information, and determine that the 2-2 information (e.g., B4) is invalid and remove the 2-1 information from the initial pore region information. In other words, the server 3000 may correct the error by comparing the probability information of the information included in the error region (e.g., E4).

Referring to FIG. 57, the initial pore region information may include second information (e.g., B5 and B6 of FIG. 57) related to the number of hairs per unit pore region. However, there may be an error in the second information related to the number of hairs per pore region.

For example, information related to the number of hairs per unit pore region may be obtained by overlapping "some". For example, referring to the error region E5 of FIG. 57, although two hairs are actually present in one pore, the 2-1 information (e.g., B5) indicating that two hairs are present in one pore region and the 2-2 information (e.g., B6) indicating that one hair is present in one pore region may be simultaneously obtained.

The server 3000 according to an embodiment of the present disclosure may perform an operation of correcting the above-described error. For example, the server 3000 may correct the initial pore region information based on the degree of overlap of the information on the number of hairs per unit pore region. In detail, when the degree of overlap between the information on the number of hairs per unit pore region exceeds a predetermined ratio, the server 3000 may determine that an error exists in the information on the number of hairs per unit pore region. In addition, the server 3000 may correct the initial pore region information based on a result of determining that the error exists. For another example, the server 3000 may correct the initial pore region information by considering quantitative information on the number of hairs per pore region related to the error area. For example, in the error region E5 of FIG. 57, the number of hairs (e.g., two) obtained by the 2-1 information (e.g., B5) and the number of hairs (e.g., one) obtained by the 2-2 information (e.g., B6) may be different. In this case, the server 3000 may determine that the error exists based on the quantitative information of the initial pore region information. In addition, the server 3000 may correct the initial pore region information based on a result of determining that the error exists.

The server 3000 may correct the error based on the probability information of the information related to the number of hairs per pore region included in the error area. For example, when the first probability information related to the 2-1 information (e.g., B5) of FIG. 57 has a first value and the second probability information related to the 2-2 information (e.g., B6) of FIG. 57 has a second value lower than the first value, the server 3000 may determine that the 2-1 information (e.g., B5) is valid and include the 2-1 information as the final pore region information, and determine that the 2-1 information (e.g., B6) is not valid and remove the 2-1 information from the initial pore region information. In other words, the server 3000 may correct the initial pore region information based on the probability information of the information included in the error-related area.

The above-described post processing related to FIGS. 55 to 57 is merely exemplary. Accordingly, the server 3000 may be implemented to use any method to correct the initial pore region information. In addition, the initial pore region information may be corrected using any software. Alternatively, the initial pore region information may be manually corrected based on a user input.

Hereinafter, a method of obtaining hair loss diagnosis assistance information based on the final pore region information will be described in detail.

Referring back to FIG. 48, a method of obtaining hair loss diagnosis assistance information according to an embodiment of the present disclosure may include acquiring hair loss diagnosis assistance information (S4400). The hair loss diagnosis assistance information may be calculated based on the final pore region information. The pore region final information may be information corrected based on the pore region initial information. However, as described above, when there is no error in the pore region initial information, the pore region final information may be used in a substantially same meaning as the pore region initial information.

Figure 58:
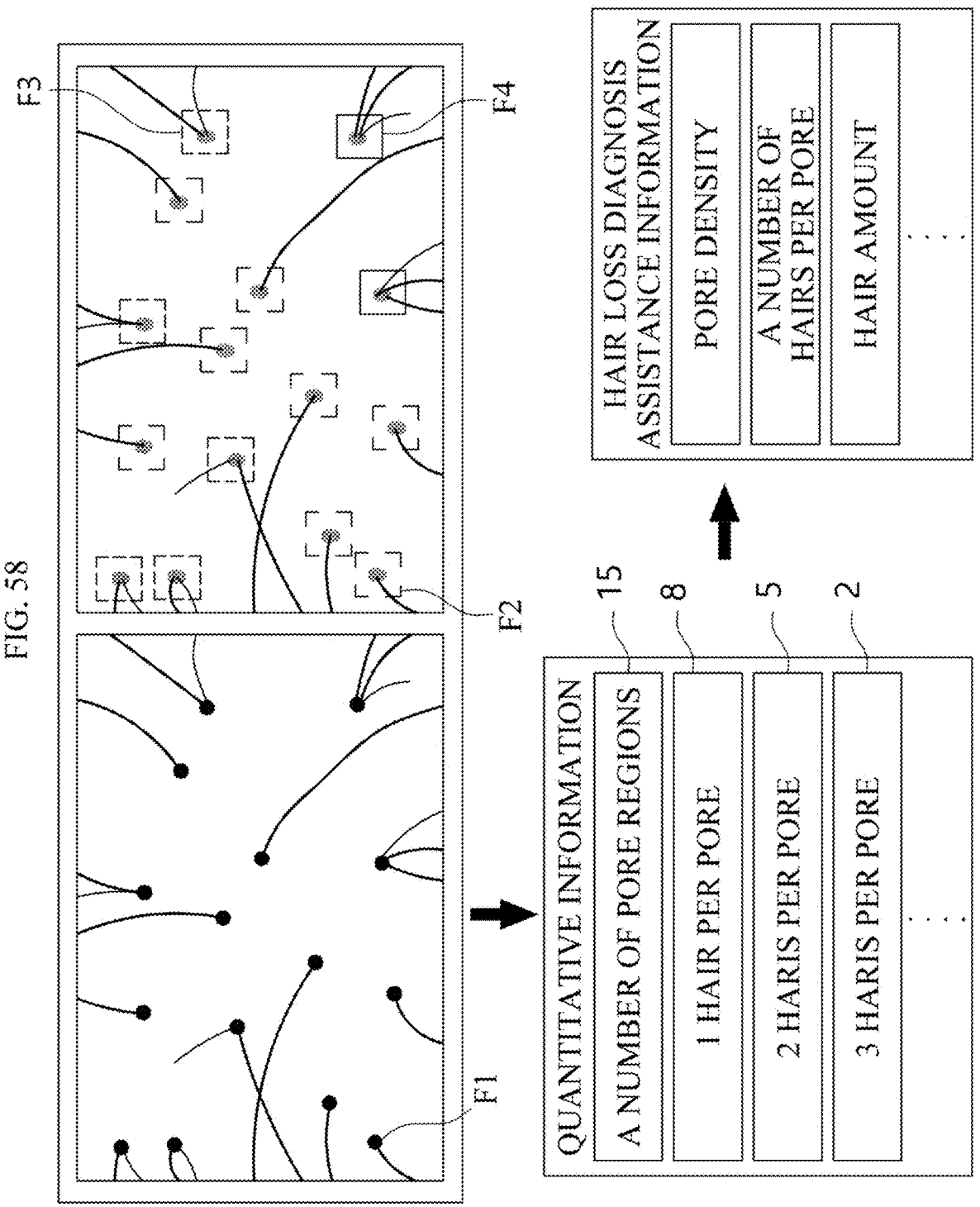
FIG. 58 is a diagram illustrating an aspect of calculating hair loss diagnosis assistance information according to an embodiment of the present application.

Hereinafter, aspects of calculating hair loss diagnosis assistance information according to an embodiment of the present application will be described in detail with reference to FIG. 58. The hair loss diagnosis assistance information may be calculated based on the pore region final information.

For example, the hair loss diagnosis assistance information may be calculated based on quantitative information obtained based on the pore region final information. Here, the quantitative information may include any information that may be calculated and numerated based on the pore region final information. For example, the quantitative information may include first quantitative information related to the total number of pore regions included in the target image, second quantitative information related to the number of pore regions having one hair, third quantitative information related to the number of pore regions having two hairs, and fourth quantitative information related to the number of pore regions having three hairs.

The first quantitative information may be calculated based on first information F1 related to the pore region among the pore region final information related to the target image. Specifically, the first quantitative information related to the total number of pore regions included in the target image may be calculated based on the first information F1 included in the target image. For example, in the target image of FIG. 58, a total of 15 pore regions are detected, and based on this, the server 3000 may calculate first quantitative information indicating that a total of 15 pore regions are obtained from the target image.

The second quantitative information may be calculated based on second information F2 related to the pore region having one hair among the pore region final information related to the target image. For example, the second quantitative information may be calculated based on second information F2 related to the pore region having one hair included in the target image. For example, the second quantitative information may be obtained based on the "number" of the second information F2 related to the pore region having one hair. In the target image of FIG. 58, a total of 8 pore regions having one hair are detected, and based on this, the server 3000 may calculate second quantitative information indicating that a total of 8 pore regions having one hair are obtained from the target image.

The third quantitative information may be calculated based on second information F3 related to the pore region having two hairs among the pore region final information related to the target image. For example, the third quantitative information may be calculated based on second information F3 related to the pore region having two hairs included in the target image. For example, the third quantitative information may be obtained based on the "number" of the information F3 related to the pore region having two hairs. For example, in the target image of FIG. 58, a total of 5 pore regions having two hairs are detected, and based on this, the server 3000 may calculate third quantitative information indicating that a total of 5 pore regions having two hairs are obtained from the target image.

The fourth quantitative information may be calculated based on second information F4 related to the pore region having three hairs among the pore region final information related to the target image. For example, the fourth quantitative information may be calculated based on the second information F4 related to the pore region having the three hair counts included in the target image. For example, the fourth quantitative information may be calculated based on the "number" of the information F4 related to the pore region having the three hair counts. For example, in the target image of FIG. 58, a total of two pore regions having a total of three hair counts have been detected, and based on the detected total of two pore regions, the server 3000 may calculate the fourth quantitative information indicating that two pore regions having a total of three hair counts have been acquired from the target image.

The hair loss diagnosis assistance information may include any type of information that may be used for diagnosing hair loss. For example, the hair loss diagnosis assistance information may include information related to pore density, hair count per pore, hair amount, temperature, odor, humidity, sensitivity, keratin amount, etc.

The hair loss diagnosis assistance information may be calculated based on the pore region final information. Specifically, the hair loss diagnosis assistance information may be calculated based on quantitative information including first quantitative information, second quantitative information, third quantitative information, and/or fourth quantitative information calculated from the pore region final information.

For example, the pore density may be calculated based on the first quantitative information related to the number of pore regions calculated based on the first information F1. Additionally, the server 3000 may further acquire information on the area of the target image. In this case, the server 3000 may be implemented to calculate the pore density (e.g., the number of pores per unit area) based on the area of the target image and the first quantitative information. For example, the server 3000 may calculate the hair loss diagnosis assistance information indicating that the pore density is 15/cm2 based on the first quantitative information indicating that the total area of the target image is A cm2 and the number of pore regions included in the target image is 15.

For example, the hair amount may be calculated based on quantitative information (e.g., the second quantitative information, the third quantitative information, and the fourth quantitative information) calculated from the second information (e.g., F2, F3, F4) related to the number of hairs per unit pore region. For example, referring to FIG. 58, the server 3000 may calculate the hair loss diagnosis assistance information related to the amount of hairs indicating that a total of 24 hairs are included in the target image based on the second quantitative information indicating that the number of pore regions having one hair is 8, the third quantitative information indicating that the number of pore regions having two hairs is 5, and the fourth quantitative information indicating that the number of pore regions having three hairs is 2.

For example, the number of hairs per pore may be calculated based on the first quantitative information related to the number of pore regions and the hair loss diagnosis assistance information related to the amount of hairs. For example, referring to FIG. 58, the server 3000 may calculate the hair loss diagnosis assistance information indicating that the number of hairs per pore of 1.6/number of pores based on the first quantitative information indicating that the number of hairs is 24 and the number of total pore regions is 15.

However, the above-described hair loss diagnosis assistance information is merely an example, and may be implemented to acquire any appropriate type of hair loss diagnosis assistance information. Further, the above-described method of calculating the hair loss diagnosis assistance information is merely an example, and it is also understood that a pore density, a hair amount, a number of hairs per pore, and/or any hair loss diagnosis assistance information may be calculated by any suitable method.

Hereinafter, an operation of calculating a hair loss progression indicator according to an embodiment of the present application will be described in detail with reference to FIGS. 59 to 61. The present embodiment may be performed by the server 3000. Alternatively, the present embodiment may be performed by the scalp measuring device 1000 or the electronic device 2000.

Figure 59:
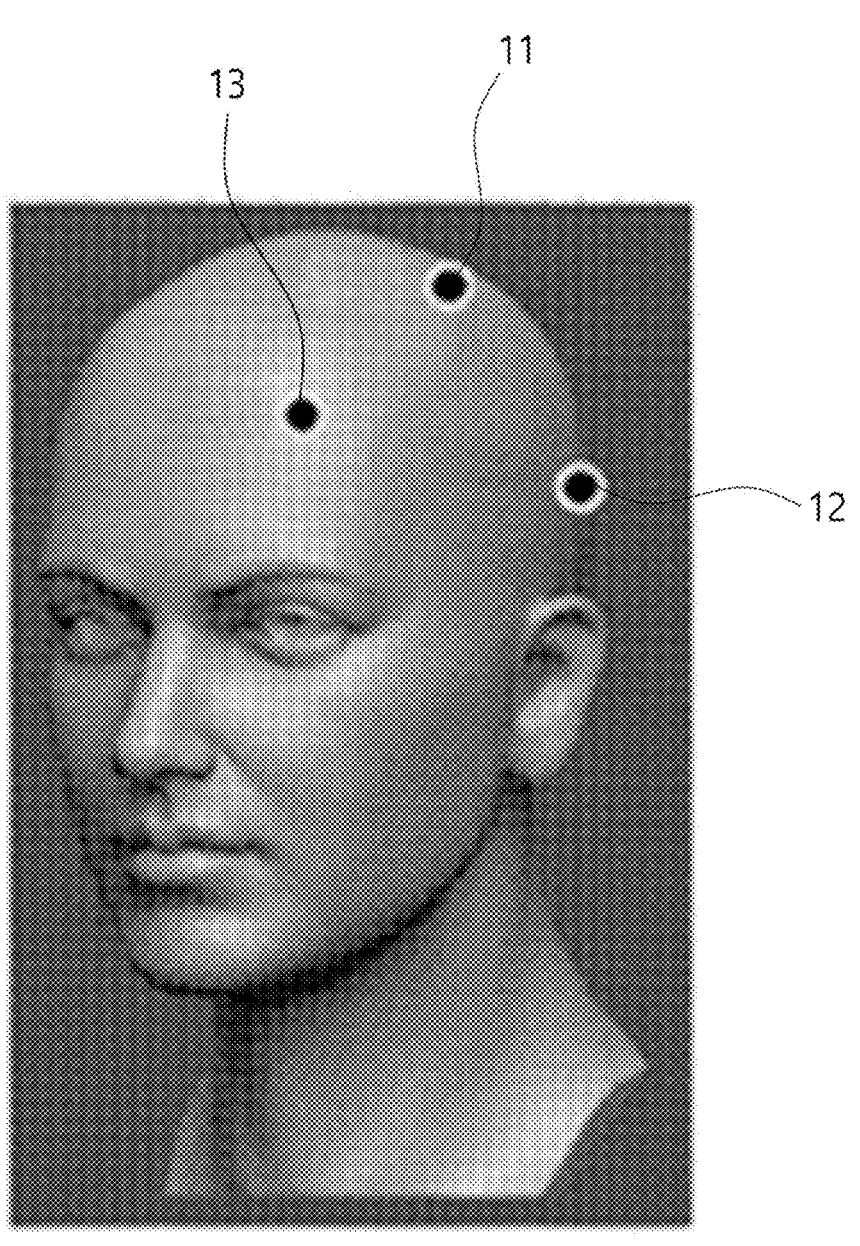
FIG. 59 is a diagram for describing a scalp area.
Figure 60:
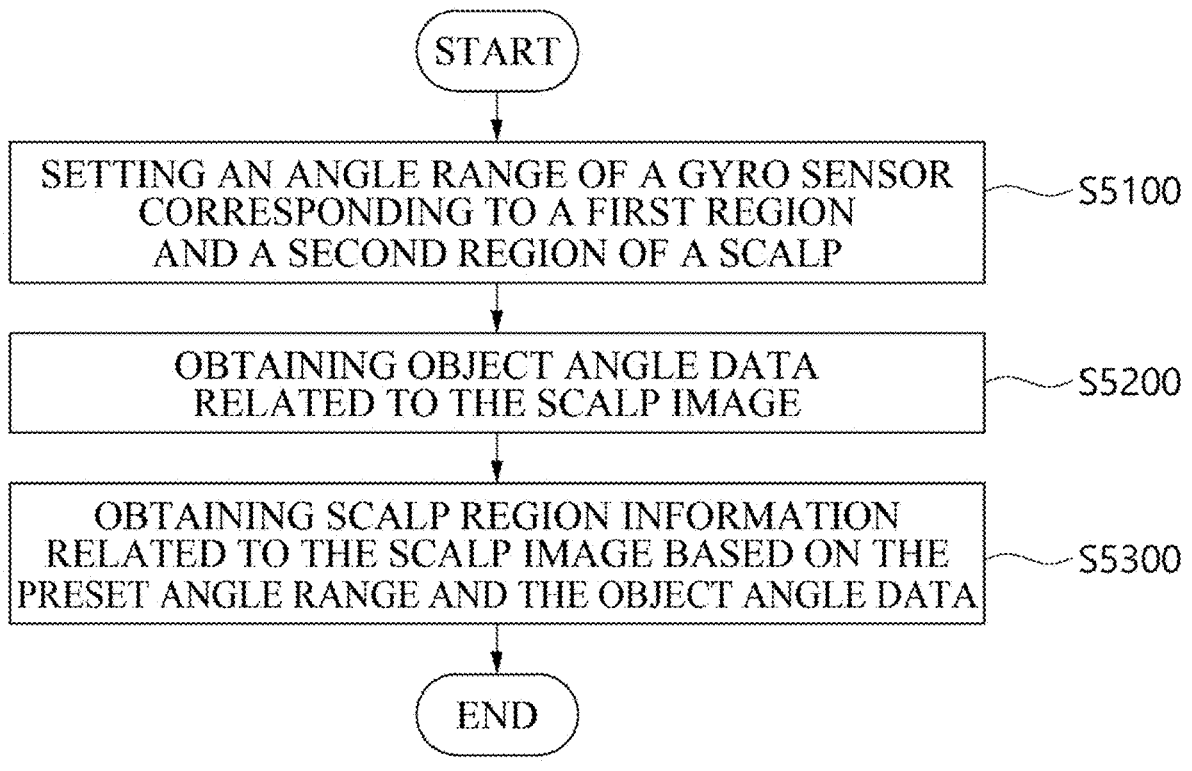
FIG. 60 is a flowchart illustrating a method of acquiring area information related to a scalp image to calculate a hair loss progression indicator according to an embodiment of the present application.

FIG. 59 is a diagram for describing a scalp region. In general, hair loss occurs in a first portion 11 (e.g., a parietal region) of the scalp or in a second portion 12 of the scalp relatively high. On the other hand, hair loss occurs in a third portion 13 (e.g., a posterior head region) of the scalp relatively low. Therefore, comparing the hair loss diagnosis assistance information on the first and second portions 11 and 12 (hereinafter, referred to as a hair loss region) of the scalp with the hair loss diagnosis assistance information on the third portion 13 (hereinafter, referred to as a health region) of the scalp may mean that the user may provide information on the degree of hair loss progress.

In order to calculate the hair loss progression indicator by comparing the hair loss diagnosis assistance information on the hair loss region and the health region, it is necessary to obtain information on whether the scalp image to be analyzed is a scalp image related to the hair loss region or a scalp image related to the health region. According to the present embodiment, in order to identify whether the scalp image to be analyzed is a scalp image related to the hair loss region or a scalp image related to the health region, the angle data obtained from the gyro sensor 1104 of the scalp measuring device 1000 may be used. More specifically, the angle range of the gyro sensor 1104 corresponding to the case of photographing a specific region of the scalp may be preset, and the region information related to the scalp image may be obtained based on whether the angle data corresponding to the obtained scalp image belongs to the preset angle range. For example, the first angle range may be preset in the hair loss region, and the second angle range may be preset in the health region. In this case, when the angle data obtained from the gyro sensor 1104 belongs to the first angle range, the server 3000 may identify that the scalp image is an image obtained by photographing the hair loss region. On the other hand, when the angle data obtained from the gyro sensor 1104 belongs to the second angle range, the server 3000 may identify that the scalp image is an image obtained by photographing the health region.

Hereinafter, a method of obtaining region information related to a scalp image for calculating a hair loss progression indicator according to an embodiment of the present application will be described in detail with reference to FIG. 60.

According to an embodiment of the present disclosure, a method of obtaining region information related to a scalp image may include setting an angle range of a gyro sensor corresponding to a first region and a second region of a scalp (S5100), obtaining a scalp image and object angle data related to the scalp image (S5200) and obtaining scalp region information related to the scalp image based on the preset angle range and the object angle data (S5300).

In the step S5100 of setting an angle range of the gyro sensor corresponding to the first region and the second region, respectively, a first angle range of the gyro sensor corresponding to the first region (e.g., a health region) and a second angle range of the gyro sensor corresponding to the second region (e.g., a hair loss region) may be preset.

For example, the user may be guided to photograph the first region (e.g., a health region) and the second region (e.g., a hair loss region) using the scalp measuring device 1000. Accordingly, the user may request photographing of the first region and the second region through the input unit 1400, respectively. In this case, the scalp measuring device 1000 may acquire one or more angle data for the first region and one or more angle data for the second region, respectively, through the gyro sensor 1104, in response to a user input. In this case, the scalp measuring device 1000 may preset a first angle range corresponding to the first region based on the one or more angle data for the first region. In addition, the scalp measuring device 1000 may preset a second angle range corresponding to the second region based on the one or more angle data for the second region.

However, the above description is only an example, and an angle range related to a scalp region may be predetermined by any suitable method.

In the step S5200 of acquiring object angle data related to a scalp image, object angle data related to the scalp image acquired through the gyro sensor 1104 may be acquired. Here, the scalp image may mean a selected object image as described above with reference to FIGS. 37 to 47. In addition, the object angle data means angle data of the gyro sensor 1104 related to the scalp image.

The scalp image may be acquired together with the object angle data. For example, the object angle data may be structured as metadata in the scalp image, and the scalp image and the object angle data may be acquired together.

Alternatively, the scalp image may be acquired separately from the object angle data. For example, when the scalp image is acquired separately from the object angle data, the object angle data may be identified as being related to the scalp image using an identification factor.

In the step S5300 of acquiring region information related to the scalp image, region information related to the scalp image may be acquired based on the preset angle range and the object angle data.

For example, a first angle range may be preset for the first region (e.g., a health region). Here, when the object angle data of the acquired scalp image belongs to the first angle range, the server 3000 may acquire information indicating that the scalp image is a scalp image related to the first region (e.g., a health region). In other words, when the object angle data of the scalp image belongs to the first angle range, the server 3000 may identify that the scalp image is a scalp image acquired by photographing the first region (e.g., a health region).

Similarly, a second angle range different from the first angle range may be preset for the second region (e.g., a hair loss region). Here, when the object angle data of the acquired scalp image belongs to the second angle range, the server 3000 may acquire information indicating that the scalp image is a scalp image related to the second region (e.g., a hair loss region). In other words, when the target angle data of the scalp image belongs to the second angle range, the server 3000 may identify that the scalp image is a scalp image acquired by photographing the second region (e.g., the hair loss region).

The region information related to the scalp image may be used to calculate the hair loss progression indicator to be described below. Hereinafter, a method of calculating the hair loss progression indicator according to an embodiment of the present application will be described in detail with reference to FIG. 61.

The method of calculating the hair loss progression indicator according to an embodiment of the present application may include acquiring a first target image related to the first region and a second target image related to the second region (S6100), acquiring first hair loss diagnosis assistance information related to the first target image (S6200), acquiring second hair loss diagnosis assistance information related to the second target image (S6300), and calculating the hair loss progression indicator based on the first hair loss diagnosis assistance information and the second hair loss diagnosis assistance information (S6400).

In the step of acquiring the first target image related to the first region and the second target image related to the second region (S6100), the first target image and the second target image may be acquired. The first target image and the second target image may be a target image selected from a plurality of scalp images from the scalp measuring device 1000 or the electronic device 2000, as described above with reference to FIGS. 37 to 47.

Meanwhile, as described with reference to FIG. 60, the first target image may be identified as a scalp image related to the first region (e.g., a health region). Similarly, the second target image may be identified as a scalp image related to the second region (e.g., a hair loss region).

In the step of acquiring the first hair loss diagnosis assistance information related to the first target image (S6200), the first hair loss diagnosis assistance information may be calculated based on the first target image, as described above with reference to FIGS. 48 to 58. For example, the server 3000 may acquire initial pore region information related to the first target image using a trained neural network model, correct pore region initial information to acquire final pore region information, and calculate the first hair loss diagnosis assistance information for the first region based on the final pore region information.

Similarly, in the step of acquiring the second hair loss diagnosis assistance information related to the second target image (S6300), the second hair loss diagnosis assistance information may be calculated based on the second target image, as described above with reference to FIGS. 48 to 58. For example, the server 3000 may acquire initial pore region information related to the second target image using a neural network model, correct pore region initial information to acquire final pore region information, and calculate the second hair loss diagnosis assistance information for the second region based on the final pore region information.

In the step of calculating the hair loss progression indicator based on the first hair loss diagnosis assistance information and the second hair loss diagnosis assistance information (S6400), the hair loss progression indicator may be calculated based on the first hair loss diagnosis assistance information related to the first region (e.g., a health region) and the second hair loss diagnosis assistance information related to the second region (e.g., a hair loss region). For example, the first hair loss diagnosis assistance information may include information on a first pore density, a first hair amount, and/or a number of hairs per first pore related to the first region (e.g., a health region). In addition, the second hair loss diagnosis assistance information may include information on the second pore density, the second hair amount, and/or the number of hairs per second pore related to the second region (e.g., the hair removal region).

In this case, the hair loss progression indicator may be calculated based on the same type of information included in the first hair loss diagnosis assistance information and the second hair loss diagnosis assistance information. For example, when the first pore density has a value of a 1-1 and the second pore density has a value of a 2-1, the hair loss progression indicator may be calculated based on the value of the 1-1 and the value of the 2-1. As another example, when the first hair amount has a value of 1-2 and the second hair amount has a value of 2-2, the hair loss progression indicator may be calculated based on the value of 1-2 and the value of 2-2. As another example, when the number of hairs per first pore has a value of 1 to 3, and the second amount of hairs has a value of 2 to 3, the hair loss progression indicator may be calculated based on the values of 1 to 3 and 2 to 3.

Alternatively, when the hair loss diagnosis assistance information includes a plurality of types of information, a hair loss progression indicator may be calculated by assigning a weight of each information. For example, a first weight may be given to the hair loss diagnosis assistance information related to the pore density, a second weight may be given to the hair loss diagnosis assistance information related to the amount of hair, and a third weight may be given to the hair loss diagnosis assistance information related to the number of hairs per pore, and a hair loss progression indicator may be calculated.

However, the above-described contents of the hair loss progression indicator are merely exemplary, and any suitable type of hair loss progression indicator may be calculated by any suitable method.

Meanwhile, according to an embodiment of the present application, the server 3000 may calculate hair loss assist diagnosis information (hair loss progression indicator) related to the scalp state based on sensing data including temperature data, humidity data, odor data, etc of the scalp.

Specifically, the server 3000 may calculate information related to a scalp state related to a scalp keratin amount and/or sensitivity of the scalp, based on a temperature, a moisture amount, and an odor of the scalp of the user acquired from the sensing data received from the scalp measuring device 1000.

In addition, according to an embodiment of the present disclosure, the server 3000 may determine a care solution suitable for the user's scalp state by using sensing data including temperature data, humidity data, odor data, etc of the scalp and a result of determining the user's scalp state. Here, the care solution may include a scalp management product such as shampoo most suitable for the scalp state of the user, environmental data, etc.

Specifically, the server 3000 may determine a score for a plurality of components based on a correlation between at least one of a temperature, a moisture content, and an odor of the user's scalp acquired from the sensing data received from the scalp measuring device 1000 and a plurality of components constituting each of the plurality of scalp management products.

The server 3000 may be implemented to calculate a score for each of the plurality of scalp management products based on the score, and may determine a care solution by selecting one or more products from among the plurality of scalp management products according to the calculated score.

Hereinafter, aspects of outputting hair loss diagnosis assistance information and/or hair loss progression indicator to a user according to an embodiment of the present application will be described in detail with reference to FIGS. 62 to 63.

Figure 63:
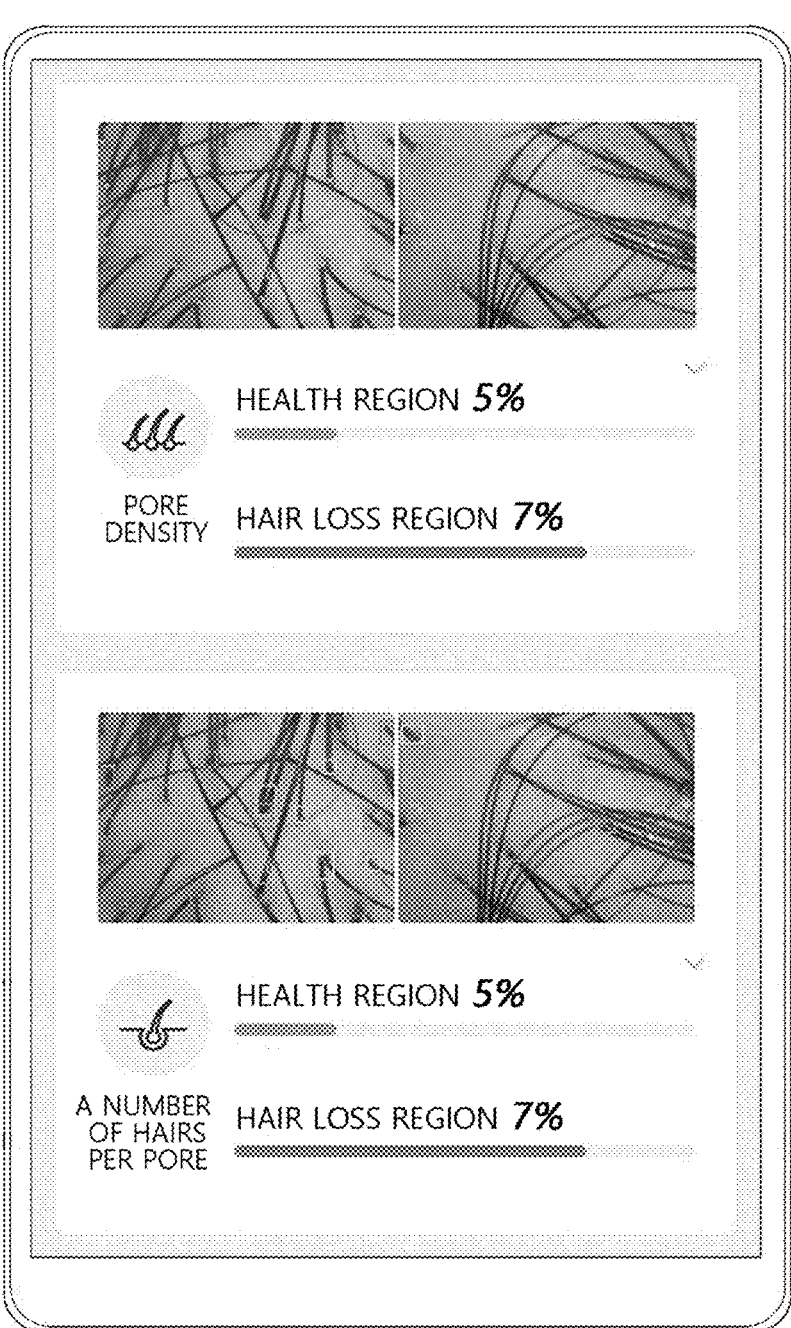
FIG. 63 is a diagram illustrating an aspect of outputting a hair loss progression indicator to a user according to an embodiment of the present application.

The hair loss diagnosis assistance information and/or the hair loss progression indicator illustrated in FIGS. 62 to 63 may be provided to the user through the output unit 2400 of the electronic device 2000. However, this is only an example, and the hair loss diagnosis assistance information and/or hair loss progression indicator shown in FIGS. 62 to 63 may be provided to the user through the output unit 1500 of the scalp measuring device 1000. Hereinafter, the electronic device 2000 outputs hair loss diagnosis assistance information and/or hair loss progression indicator. However, this is for convenience of explanation only and is not limited thereto.

The electronic device 2000 may obtain a scalp image (e.g., a target image), hair loss diagnosis assistance information, and/or hair loss progression indicator from the server 3000, and may output the hair loss diagnosis assistance information and/or the hair loss progression indicator to the user through the output unit 2400.

FIG. 62 is a diagram illustrating an aspect of outputting hair loss diagnosis assistance information to a user according to an embodiment of the present application. The hair loss diagnosis assistance information may be output together with a scalp image (e.g., a target image) and final information (e.g., F1, F2, F3, F4) of a pore region. For example, hair loss diagnosis assistance information (e.g., 15/cm2) related to pore density may be output together with a scalp image in which final information (e.g., first information F1) of a pore region is displayed. As another example, hair loss diagnosis assistance information (e.g., 1.67/pore) related to the number of hairs per pore may be output together with a scalp image displaying second information (F2 to F4) related to the pore region related to the number of hairs.

Further, the hair loss diagnosis assistance information may be output in a manner of comparing the average hair loss diagnosis assistance information of other users. For example, the hair loss diagnosis assistance information may be compared with the average hair loss diagnosis assistance information of other users and a state of the hair loss diagnosis assistance information of the user may be visually output. In this case, the hair loss diagnosis assistance information may be output together with information on the percentile of the hair loss diagnosis assistance information of the user.

In addition, the hair loss diagnosis assistance information may be output together with information on the diagnosis date. Through this, the user may be provided with hair loss diagnosis assistance information while intuitively checking his or her scalp state.

However, the above description is merely an example, and it is understood that hair loss diagnosis assistance information may be provided to the user in any suitable manner or in any suitable form.

FIG. 63 is a diagram illustrating an aspect of outputting a hair loss progression indicator to a user according to an embodiment of the present application.

The hair loss progression indicator may be output in a manner in which first hair loss diagnosis assistance information related to the first region (e.g., a health region) and second hair loss diagnosis assistance information related to the second region (e.g., a hair loss region) are compared. For example, quantitative information (e.g., percentile information (5%)) regarding pore density related to the first region (e.g., health region) and quantitative information (e.g., percentile information (7%)) regarding pore density related to the second region (e.g., hair loss region) may be output. As another example, quantitative information (e.g., percentile information (5%)) regarding the number of hairs per pore related to the first region (e.g., health region) and quantitative information (e.g., percentile information (7%)) regarding the number of hairs per pore related to the second region (e.g., hair loss region) may be output.

The hair loss progression indicator may be output together with a first target image related to the first area (e.g., a health area) and a second target image related to the second area (e.g., a hair loss area). For example, when the hair loss progression indicator related to the pore density is output, the first target image and the second target image may be output together with the pore region final information (e.g., the first information F1) displayed. For example, when the hair loss progression indicator related to the number of hairs per pore is output, the first target image and the second target image may be output together with the pore region related to the number of hairs (F2 to F4). Accordingly, the user may intuitively check his or her scalp state, particularly, which state the hair loss area is compared with the health area.

However, the above description is merely exemplary, and it is to be understood that the hair loss indicator information may be provided to the user in any suitable manner or in any suitable form.

According to the scalp image analysis system according to an embodiment of the present application, the analysis target image may be preferentially selected by the scalp measuring device 1000 or the electronic device 2000. Accordingly, inefficient operations such as requiring analysis on a plurality of scalp images to calculate the hair loss diagnosis assistance information may be prevented. Accordingly, according to the scalp image analysis system according to an embodiment of the present application, speed and efficiency of data processing in calculating the hair loss diagnosis assistance information may be increased.

According to the scalp image analysis system according to an embodiment of the present application, the target image may be automatically selected using a neural network model without simply dependent on the user's vision. In addition, according to the scalp image analysis system according to an embodiment of the present application, an operation of correcting the pore region information or comparing the corrected pore region information with a manually captured scalp image may be further performed in order to select an optimal target image. Accordingly, according to the scalp image analysis system according to an embodiment of the present application, the target image based on the calculation of the hair loss diagnosis assistance information may be selected as the optimal state. In addition, according to the scalp image analysis system according to an embodiment of the present application, accuracy and reliability of the hair loss diagnosis assistance information may be increased because the hair loss diagnosis assistance information is obtained based on the optimal target image.

According to the scalp image analysis system according to an embodiment of the present application, the pore region final information based on the calculation of the hair loss diagnosis assistance information is obtained using the trained neural network model. Accordingly, the pore region final information may be automatically obtained through the trained neural network model.

According to the scalp image analysis system according to an embodiment of the present application, quantitative numerical information such as the pore density, the number of hairs per pore and/or the amount of hairs may be provided to the user as the hair loss diagnosis assistance information. In addition, information related to the hair loss progression indicator may also be provided to the user. Accordingly, the user may receive significant quantitative information capable of checking the state of the scalp of the user.

According to the scalp image analysis system according to an embodiment of the present application, various sensing data such as temperature data, humidity data, odor data, etc., related to the scalp as well as the scalp image may be acquired, and the type of the scalp may be analyzed based on the sensing data. In addition, a suitable product may be automatically provided to the user based on the type of the scalp. Accordingly, the user may receive information on the type of the scalp of the user and information on a scalp care product suitable for the scalp type of the user.

The scalp image analysis method, scalp image analysis device, and scalp image analysis system disclosed in the present application may be used to analyze the scalp image.

In particular, the scalp image analysis method, scalp image analysis device, and scalp image analysis system disclosed in the present application may be applied to all fields providing assistance information information on the type of the scalp and the disease related to the scalp. For example, the scalp image analysis method, scalp image analysis device, and scalp image analysis system may be used in a health diagnosis field where the assistance information for diagnosing the scalp type is calculated or information related to the scalp disease is provided.

However, the scalp image analysis method, scalp image analysis device, and scalp image analysis system disclosed in the present application may be applied to not only the scalp image but also all images. For example, a method of selecting a target image for more accurate image analysis may be applied to not only the scalp image but also all image analysis fields.

The features, structures, and effects described in the above embodiments are included in at least one embodiment of the present invention, and are not necessarily limited to only one embodiment. Further, the features, structures, and effects illustrated in each embodiment may be combined or modified in other embodiments by those skilled in the art to which the embodiments belong. Accordingly, the contents related to the combination and the modification should be interpreted as being included in the scope of the present invention.

In addition, although the above description has been focused on embodiments, the present invention is not limited to the present invention only by way of example, and those skilled in the art to which the present invention belong is recognized that various modifications and applications not illustrated above may be made without departing from the essential characteristics of the embodiments. That is, each component specifically shown in the embodiments may be modified and implemented. In addition, the differences related to the modifications and the applications should be interpreted as being included in the scope of the present invention defined in the appended claims.

What is claimed is:

1. A method of selecting images for analysis to provide hair loss diagnosis assistance information, the method comprising:

obtaining a plurality of scalp images including a first scalp image and a second scalp image;

obtaining pore region information included in each scalp image;

based on the pore region information of the first scalp image, obtaining first quantitative information related to the number of pore regions included in the first scalp image;

based on the pore region information of the second scalp image, obtaining second quantitative information related to the number of pore regions included in the second scalp image; and selecting a target image by comparing the first quantitative information and the second quantitative information, wherein obtaining pore region information, further comprising:

obtaining initial pore region information related to the pore region included in the scalp image; and obtaining the pore region information by correcting the initial pore region information, wherein the correcting the initial pore region information, further comprising:

obtaining first location information and second location information related to the pore region included in the initial pore region information;

verifying the validity of the first location information and the second location information based on whether the separation distance between the first location information and the second location information is within a predetermined distance; and determining at least one of first location information and the second location information to be invalid if the separation distance between the first location information and the second location information is within a predetermined distance;

determining the first location information and the second location information to be valid if the separation distance between the first location information and the second location information is not within the predetermined distance;

determining a pore region corresponding to the location information determined to be valid as the pore region information when it is determined that at least one of the first location information and the second location information is invalid.

2. The method of claim 1, wherein selecting the target image, further comprising:

selecting a valid scalp image based on a result of comparing the first quantitative information and the second quantitative information;

obtaining a manually captured scalp image;

obtaining third quantitative information related to the number of pore regions included in the manually captured scalp image; and determining the target image based on quantitative information related to the valid scalp image and the third quantitative information related to the manually captured scalp image.

3. The method of claim 2, wherein determining the target image, further comprising:

determining an image having a greater value of quantitative information as the target image by comparing the quantitative information related to the valid scalp image and the third quantitative information related to the manually captured scalp image.

4. The method of claim 1, wherein obtaining pore region information is performed by an artificial neural network configured to obtain the pore region information based on the scalp image.

5. The method of claim 1, wherein the correcting the initial pore region information, further comprising:

obtaining first information related to the pore region included in the scalp image;

obtaining second information related to the hair region included in the scalp image; and correcting the initial pore region information based on whether the first information and the second information included in the common region range of the scalp image correspond to each other.

6. A scalp measuring device for obtaining scalp images comprising:

a camera configured to capture a plurality of scalp images; and an at least one processor configured to select images for analysis to provide hair loss diagnosis assistance information based on the plurality of scalp images;

wherein the at least one processor is configured to:

obtain the plurality of scalp images including a first scalp image and a second scalp image;

obtain pore region information included in each scalp image;

based on the pore region information of the first scalp image, obtain first quantitative information related to the number of pore regions included in the first scalp image;

based on the pore region information of the second scalp image, obtain second quantitative information related to the number of pore regions included in the second scalp image; and select a target image by comparing the first quantitative information and the second quantitative information, wherein the at least one processor is configured to obtain initial pore region information related to the pore region included in the scalp image; and obtain the pore region information by correcting the initial pore region information, wherein the at least one processor is configured to:

obtain first location information and second location information related to the pore region included in the initial pore region information;

verify the validity of the first location information and the second location information based on whether the separation distance between the first location information and the second location information is within a predetermined distance; and determining at least one of first location information and the second location information to be invalid if the separation distance between the first location information and the second location information is within a predetermined distance;

determining the first location information and the second location information to be valid if the separation distance between the first location information and the second location information is not within the predetermined distance;

determine a pore region corresponding to the location information determined to be valid as the pore region information when it is determined that at least one of the first location information and the second location information is invalid.

7. The scalp measuring device of claim 6, wherein the at least one processor is configured to select the target image by performing the steps below:

selecting a valid scalp image based on a result of comparing the first quantitative information and the second quantitative information;

obtaining a manually captured scalp image;

obtaining third quantitative information related to the number of pore regions included in the manually captured scalp image; and determining the target image based on quantitative information related to the valid scalp image and the third quantitative information related to the manually captured scalp image.

8. The scalp measuring device of claim 7, wherein the at least one processor is configured to determine an image having a greater value of quantitative information as the target image by comparing the quantitative information related to the valid scalp image and the third quantitative information related to the manually captured scalp image.

9. The scalp measuring device of claim 6, wherein the at least one processor is configured to obtain pore region information based on an artificial neural network configured to obtain the pore region information based on the scalp image.

10. The scalp measuring device of claim 6, wherein the at least one processor is configured to:

obtain first information related to the pore region included in the scalp image;

obtain second information related to the hair region included in the scalp image; and correct the initial pore region information based on whether the first information and the second information included in the common region range of the scalp image correspond to each other.

* * * * *